US012779052B2

(12) United States Patent
Vandendriessche et al.

(10) Patent No.: US 12,779,052 B2
(45) Date of Patent: Nov. 3, 2026

(54) COMBINATION OF NUCLEIC ACID REGULATORY ELEMENTS AND METHODS AND USES THEREOF

(71) Applicant: VRIJE UNIVERSITEIT BRUSSEL, Brussels (BE)

(72) Inventors: Thierry Vandendriessche, Brussels (BE); Lay Khim Chuah, Bierbeek (BE)

(73) Assignee: Vrije Universiteit Brussel, Brussels (BE)

( * ) Notice: Subject to any disclaimer, the term of this patent is extended or adjusted under 35 U.S.C. 154(b) by 1061 days.

(21) Appl. No.: 17/904,095

(22) PCT Filed: Feb. 18, 2021

(86) PCT No.: PCT/EP2021/053939

§ 371 (c)(1),
(2) Date: Aug. 11, 2022

(87) PCT Pub. No.: WO2021/165350

PCT Pub. Date: Aug. 26, 2021

(65) Prior Publication Data

US 2023/0089121 A1 Mar. 23, 2023

(30) Foreign Application Priority Data

Feb. 18, 2020 (EP) .................................... 20158064

(51) Int. Cl.
*A61K 48/00* (2006.01)
*A61K 38/17* (2006.01)
(Continued)

(52) U.S. Cl.
CPC ........ *A61K 48/0058* (2013.01); *A61K 38/177* (2013.01); *A61K 38/47* (2013.01);
(Continued)

(58) Field of Classification Search
CPC ..... A61K 48/0058; A61P 21/00; C12N 15/86; C12N 2750/14143; C12N 2820/007; C12N 2830/008; C12N 2830/42
See application file for complete search history.

(56) References Cited

U.S. PATENT DOCUMENTS

2012/0282695 A1* 11/2012 Blain ................. C07K 14/4716 435/375
2019/0032079 A1* 1/2019 McDonald ........... C12N 9/0071

FOREIGN PATENT DOCUMENTS

WO WO 2015/110449 A1 7/2015
WO WO 2018/178067 A1 10/2018
WO WO 2019/153009 A1 8/2019

OTHER PUBLICATIONS

Chuah et al., Molecular Therapy, vol. 22, Issue 9, Sep. 2014, pp. 1605-1613 (Year: 2014).*

(Continued)

*Primary Examiner* — Catherine Konopka
*Assistant Examiner* — Shabana S Meyering
(74) *Attorney, Agent, or Firm* — Knobbe, Martens, Olson & Bear LLP

(57) ABSTRACT

Disclosed herein are nucleic acid sequences that function as skeletal muscle- and diaphragm muscle-specific cis-regulatory elements (CREs). The disclosed CREs are operably linked to heterologous promoters to enhance muscle-specific expression of genes. Also provided are expression cassettes and vectors comprising the disclosed cis-regulatory elements in combination with known promoters, as well as methods of using such constructs for directing gene expression in skeletal muscle and diaphragm tissue. The disclosed elements and constructs are useful in gene therapy applications, including muscle-directed gene therapy.

13 Claims, 14 Drawing Sheets

Specification includes a Sequence Listing.

(51) Int. Cl.
*A61K 38/47* (2006.01)
*A61P 21/00* (2006.01)
*C12N 9/24* (2006.01)
*C12N 15/86* (2006.01)

(52) U.S. Cl.
CPC ............ *A61P 21/00* (2018.01); *C12N 9/2402* (2013.01); *C12N 15/86* (2013.01); *C12Y 302/0102* (2013.01); *C12N 2750/14143* (2013.01); *C12N 2820/007* (2013.01); *C12N 2830/008* (2013.01)

(56) References Cited

OTHER PUBLICATIONS

Bellotti et al., "Molecular Approaches for the Treatment of Pompe Disease", Molecular Neurobiology, Humana Press, US, vol. 57, No. 2, Nov. 12, 2019.
International Search Report and Written Opinion issued in PCT/EP2021/053939, mailed Jun. 9, 2021.

* cited by examiner

Fig. 1A

1) AAVss-SPc5-12-MVM-hGAAco-pA

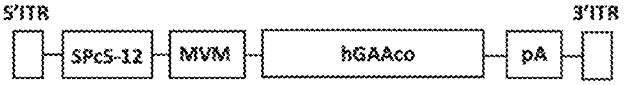

2) AAVss-DphCRE02-CSkSH1-SPc5-12-MVM-hGAAco-pA

Dph-CRE02 (SEQ ID NO: 1)

GACAGGTGCGGTTCCCGGAGCGCAGGCGCACACATGCACCCACCGGCGAACGCGGTGACCCTCGCCCCACCCCATCCCCTCCGGCGGGC
AACTGGGTCGGGTCAGGAGGGGCAAACCCGCTAGGGAGACACTCCATATACGGCCCGGCCCGCGTTACCTGGGACCGGGCCAACCCGC
TCCTTCTTTGGTCAACGCAGGGGACCCGGGCGGGGGCCCAGGCCGCGAACCGGCCGAGGGAGGGGGCTCTAGTGCCCAACACCCAAAT
ATGGCTCGAGAAGGGCAGCGACATTCCTGCGGGGTGGCGCGGAGGGAATGCCCGCGGGCTATATAAAACCTGAGCAGAGGGACAAGC
GGCCACCGCAGCGGACAGCGCCAAGTGAAGCCTCGCTTCCCCTCCGCGGCGACCAGGGCCCGAGCCGAGAGTAGCAGTTGTAGCTACC
CGCCCAGGTAGG

CSk-SH1 (SEQ ID NO: 2)

GTTCTCCTCTATAAATACCCGCTCTGGTATTTGGGGTTGGCAGCTGTTGCTGCCAGGGAGATGGTTGGGTTGACATGCGGCTCCTGACAA
AACACAAACCCCTGGTGTGTGTGGGCGTGGGTGGTGTGAGTAGGGGGATGAATCAGGGAGGGGGCGGGGGACCCAGGGGGCAGGAG
CCACACAAAGTCTGTGCGGGGGTGGGAGCGCACATAGCAATTGGAAACTGAAAGCTTATCAGACCCTTTCTGGAAATCAGCCCACTGTT
TATAAACTTGAGGCCCCACCCTCGACAGTACCGGGGAGGAAGAGGGCCTGCACTAGTCCAGAGGGAAACTGAGGCTCAGGGCTAGCTC
GCCCATAGACATACATGGCAGGCAGGCT

Dph-CRE02-CSKSH1 (SEQ ID NO: 3)

GACAGGTGCGGTTCCCGGAGCGCAGGCGCACACATGCACCCACCGGCGAACGCGGTGACCCTCGCCCCACCCCATCCCCTCCGGCGGGC
AACTGGGTCGGGTCAGGAGGGGCAAACCCGCTAGGGAGACACTCCATATACGGCCCGGCCCGCGTTACCTGGGACCGGGCCAACCCGC
TCCTTCTTTGGTCAACGCAGGGGACCCGGGCGGGGGCCCAGGCCGCGAACCGGCCGAGGGAGGGGGCTCTAGTGCCCAACACCCAAAT
ATGGCTCGAGAAGGGCAGCGACATTCCTGCGGGGTGGCGCGGAGGGAATGCCCGCGGGCTATATAAAACCTGAGCAGAGGGACAAGC
GGCCACCGCAGCGGACAGCGCCAAGTGAAGCCTCGCTTCCCCTCCGCGGCGACCAGGGCCCGAGCCGAGAGTAGCAGTTGTAGCTACC
CGCCCAGGTAGGGGCGCGCCACGCGT*GTTCTCCTCTATAAATACCCGCTCTGGTATTTGGGGTTGGCAGCTGTTGCTGCCAGGGAGAT
GGTTGGGTTGACATGCGGCTCCTGACAAAACACAAACCCCTGGTGTGTGTGGGCGTGGGTGGTGTGAGTAGGGGGATGAATCAGGGA
GGGGGCGGGGGACCCAGGGGGCAGGAGCCACACAAAGTCTGTGCGGGGGTGGGAGCGCACATAGCAATTGGAAACTGAAAGCTTATC
AGACCCTTTCTGGAAATCAGCCCACTGTTTATAAACTTGAGGCCCCACCCTCGACAGTACCGGGGAGGAAGAGGGCCTGCACTAGTCCA
GAGGGAAACTGAGGCTCAGGGCTAGCTCGCCCATAGACATACATGGCAGGCAGGCT

**the bold and underlined nucleotide sequence of SEQ ID NO: 3 indicates the nucleotide linker between Dph-CRE02 (SEQ ID NO: 1) and CSk-SH1 (SEQ ID NO: 2).*

Plasmid AAVss-Dph-CRE02-CSkSH1-SPc5-12-MVM-hGAAco-SynthpA (SEQ ID NO: 9)

ACATGTCCTGCAGGCAGCTGCGCGCTCGCTCGCTCACTGAGGCCGCCCGGGCAAAGCCCGGGCGTCGGGCGACCTTTGGTCGCCCGGCC
TCAGTGAGCGAGCGAGCGCGCAGAGAGGGAGTGGCCAACTCCATCACTAGGGGTTCCTGCGGCCGCACGCGTACCGGTGACAGGTGC
GGTTCCCGGAGCGCAGGCGCACACATGCACCCACCGGCGAACGCGGTGACCCTCGCCCCACCCCATCCCCTCCGGCGGGCAACTGGGTC
GGGTCAGGAGGGGCAAACCCGCTAGGGAGACACTCCATATACGGCCCGGCCCGCGTTACCTGGGACCGGGCCAACCCGCTCCTTCTTTG
GTCAACGCAGGGGACCCGGGCGGGGGCCCAGGCCGCGAACCGGCCGAGGGAGGGGGCTCTAGTGCCCAACACCCAAATATGGCTCGA

Fig. 1B

GAAGGGCAGCGACATTCCTGCGGGGTGGCGCGGAGGGAATGCCCGCGGGCTATATAAAACCTGAGCAGAGGGACAAGCGGCCACCGC
AGCGGACAGCGCCAAGTGAAGCCTCGCTTCCCCTCCGCGGCGACCAGGGCCCGAGCCGAGAGTAGCAGTTGTAGCTACCCGCCCAGGT
AGGGGCGCGCCACGCGTGTTCTCCTCTATAAATACCCGCTCTGGTATTTGGGGTTGGCAGCTGTTGCTGCCAGGGAGATGGTTGGGTTG
ACATGCGGCTCCTGACAAAACACAAACCCCTGGTGTGTGTGGGCGTGGGTGGTGTGAGTAGGGGGATGAATCAGGGAGGGGGCGGGG
GACCCAGGGGGCAGGAGCCACACAAAGTCTGTGCGGGGGTGGGAGCGCACATAGCAATTGGAAACTGAAAGCTTATCAGACCCTTTCT
GGAAATCAGCCCACTGTTTATAAACTTGAGGCCCCACCCTCGACAGTACCGGGGAGGAAGAGGGCCTGCACTAGTCCAGAGGGAAACT
GAGGCTCAGGGCTAGCTCGCCCATAGACATACATGGCAGGCAGGCTGGTACCCAACCCGTTACGTGGCCACCGCCTTCGGCACCATCCT
CACGACACCCAAATATGGCGACGGGTGAGGAATGGTGGGGAGTTATTTTTAGAGCGGTGAGGAAGGTGGGCAGGCAGCAGGTGTTGG
CGCTCTAAAAATAACTCCCGGGAGTTATTTTTAGAGCGGAGGAATGGTGGACACCCAAATATGGCGACGGTTCCTCACCCGTCGCCATAT
TTGGGTGTCCGCCCTCGGCCGGGGCCGCATTCCTGGGGGCCGGGCGGTGCTCCCGCCCGCCTCGATAAAAGGCTCCGGGGCCGGCGGC
GGCCCACGAGCTACCCGGAGGAGCGGGAGGCGCCAAGCTCTAGATCTAGAACTAGTAAGAGGTAAGGGTTTAAGGGATGGTTGGTTG
GTGGGGTATTAATGTTTAATTACCTGGAGCACCTGCCTGAAATCACTTTTTTTCAGGTTGGCGTACGGCCACCATGGGCGTCAGACATCCT
CCATGTTCTCACAGACTGCTGGCCGTGTGTGCTCTGGTGTCTCTTGCTACAGCTGCCCTGCTGGGACATATCCTGCTGCACGATTTTCTGC
TGGTGCCCAGAGAGCTGTCTGGCAGCTCTCCTGTGCTGGAAGAAACACACCCTGCACATCAGCAGGGCGCCTCTAGACCTGGACCTAGA
GATGCTCAAGCCCATCCTGGCAGACCTAGAGCCGTGCCTACACAGTGTGACGTGCCACCTAACAGCAGATTCGACTGCGCCCCTGACAA
GGCCATCACACAAGAGCAGTGTGAAGCCAGAGGCTGCTGCTACATTCCTGCCAAACAAGGACTGCAGGGCGCTCAGATGGGACAGCCT
TGGTGCTTCTTCCCACCATCTTACCCCAGCTACAAGCTGGAAAACCTGAGCAGCAGCGAGATGGGCTACACCGCCACACTGACCAGAACC
ACACCTACATTCTTCCCAAAGGACATCCTGACACTGCGGCTGGACGTGATGATGGAAACCGAGAACCGGCTGCACTTCACCATCAAGGAC
CCCGCCAATAGAAGATACGAGGTGCCCCTGGAAACCCCTCACGTGCACTCTAGAGCCCCATCTCCACTGTACAGCGTGGAATTCAGCGAG
GAACCCTTTGGCGTGATCGTGCGGAGACAGCTGGATGGCAGAGTGCTGCTGAATACCACAGTGGCCCCTCTGTTCTTCGCCGACCAGTTT
CTGCAGCTGAGCACAAGCCTGCCTAGCCAGTATATCACAGGCCTGGCCGAACACCTGTCTCCACTGATGCTGAGCACCAGCTGGACCAG
AATCACCCTGTGGAACAGAGATCTGGCCCCTACACCTGGCGCCAATCTGTACGGCTCTCACCCTTTTTATCTGGCCCTGGAAGATGGCGG
AAGCGCCCACGGTGTCTTTCTGCTGAACAGCAACGCCATGGACGTGGTGCTGCAACCATCTCCTGCTCTGTCTTGGAGAAGCACCGGCG
GCATCCTGGACGTGTACATCTTTCTGGGACCCGAGCCTAAGAGCGTGGTGCAGCAGTATCTGGATGTCGTGGGCTACCCCTTCATGCCTC
CTTATTGGGGCCTGGGCTTCCACCTGTGTAGATGGGGATACAGCTCCACCGCCATCACCAGACAGGTGGTGGAAAACATGACCCGGGCT
CACTTCCCACTGGATGTGCAGTGGAACGACCTGGACTACATGGACTCCAGACGGGACTTCACCTTTAACAAGGACGGCTTCAGAGACTTC
CCCGCCATGGTGCAAGAACTGCATCAAGGCGGCAGACGGTACATGATGATCGTGGATCCTGCCATCTCTTCTAGCGGCCCTGCCGGAAG
CTACAGACCTTATGATGAGGGCCTGAGAAGAGGCGTGTTCATCACCAATGAGACAGGCCAGCCTCTGATCGGCAAAGTGTGGCCTGGA
AGCACCGCCTTTCCAGACTTCACCAATCCAACCGCTCTGGCTTGGTGGGAAGATATGGTGGCCGAGTTCCACGATCAGGTGCCCTTCGAT
GGCATGTGGATCGACATGAACGAGCCCAGCAACTTCATCAGGGGCAGCGAGGATGGCTGCCCCAACAACGAACTGGAAAATCCTCCTTA
CGTGCCAGGCGTTGTCGGAGGAACACTGCAGGCCGCCACAATTTGTGCCAGCAGCCATCAGTTTCTGAGCACCCACTACAACCTGCACA
ACCTGTACGGCCTGACCGAGGCCATTGCCTCTCATAGAGCCCTGGTTAAGGCCAGAGGCACCCGGCCTTTTGTGATCAGCAGAAGCACA
TTTGCCGGCCACGGCAGATATGCCGGACATTGGACAGGGGACGTTTGGTCTAGTTGGGAGCAGCTGGCCTCTAGCGTGCCCGAGATCCT
GCAGTTTAATCTGCTGGGAGTGCCCCTCGTGGGAGCCGATGTTTGTGGATTTCTGGGCAACACCTCCGAGGAACTGTGCGTCAGATGGA
CACAGCTGGGCGCCTTCTATCCCTTCATGAGAAACCACAACAGCCTGCTGAGCCTGCCTCAAGAGCCTTACAGCTTTAGCGAACCCGCAC
AGCAGGCCATGAGAAAGGCCCTGACTCTGAGATACGCTCTGCTGCCCCACCTGTACACCCTGTTTCATCAAGCTCATGTGGCCGGCGAGA
CAGTGGCCAGACCACTGTTTCTGGAATTCCCCAAGGACAGCAGCACCTGGACAGTGGATCATCAGCTGCTCTGGGGAGAAGCCCTGCTC
ATTACACCTGTGCTGCAGGCTGGCAAGGCCGAAGTGACAGGATACTTTCCCCTCGGCACTTGGTACGACCTGCAGACAGTTCCTGTGGA
AGCTCTGGGATCTCTGCCTCCACCTCCTGCTGCTCCTAGAGAGCCTGCCATTCACTCTGAAGGCCAGTGGGTTACACTGCCCGCTCCACTG
GACACCATCAATGTGCACCTGAGAGCCGGCTACATCATCCCTCTGCAAGGCCCTGGACTGACCACAACCGAAAGCAGACAGCAGCCAAT
GGCTCTGGCCGTGGCTCTGACAAAAGGCGGAGAAGCTAGAGGCGAACTGTTCTGGGATGACGGCGAGAGCCTGGAAGTGCTGGAACG
GGGAGCCTACACACAAGTGATCTTTCTCGCCCGGAACAACACCATCGTGAACGAACTCGTCAGAGTGACCAGTGAAGGTGCCGGACTGC
AGCTCCAGAAAGTGACAGTGCTTGGAGTGGCCACAGCACCCCAGCAGGTTTTGTCTAATGGCGTGCCCGTGTCCAACTTCACATACAGCC
CTGACACCAAGGTGCTGGACATCTGTGTGTCTCTGCTGATGGGCGAGCAGTTCCTGGTGTCCTGGTGTTGACCTAGGAATAAAAGATCTT
TATTTTCATTAGATCTGTGTGTTGGTTTTTTGTGTGACCCGTCTGATTTTGTAGGTAACCACGTGCGGACCGAGCGGCCGCAGGAACCCCT
AGTGATGGAGTTGGCCACTCCCTCTCTGCGCGCTCGCTCGCTCACTGAGGCCGGGCGACCAAAGGTCGCCCGACGCCCGGGCTTTGCCC
GGGCGGCCTCAGTGAGCGAGCGAGCGCGCAGCTGCCTGCAGGGGCGCCTGATGCGGTATTTTCTCCTTACGCATCTGTGCGGTATTTCA
CACCGCATACGTCAAAGCAACCATAGTACGCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGATTTGGGTGATGGTTCACGTAGTGGGCCATC
GCCCTGATAGACGGTTTTTCGCCCTTTGACGTTGGAGTCCACGTTCTTTAATAGTGGACTCTTGTTCCAAACTGGAACAACACTCAACCCT
ATCTCGGGCTATTCTTTTGATTTATAAGGGATTTTGCCGATTTCGGCCTATTGGTTAAAAAATGAGCTGATTTAACAAAAATTTAACGCGA

Fig. 1C

ATTTTAACAAAATATTAACGTTTACAATTTTATGGTGCACTCTCAGTACAATCTGCTCTGATGCCGCATAGTTAAGCCAGCCCCGACACCC
GCCAACACCCGCTGACGCGCCCTGACGGGCTTGTCTGCTCCCGGCATCCGCTTACAGACAAGCTGTGACCGTCTCCGGGAGCTGCATGTG
TCAGAGGTTTTCACCGTCATCACCGAAACGCGCGAGACGAAAGGGCCTCGTGATACGCCTATTTTTATAGGTTAATGTCATGATAATAAT
GGTTTCTTAGACGTCAGGTGGCACTTTTCGGGGAAATGTGCGCGGAACCCCTATTTGTTTATTTTTCTAAATACATTCAAATATGTATCCG
CTCATGAGACAATAACCCTGATAAATGCTTCAATAATATTGAAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCATACACTATTCTCAGAATGACTTGGTTGAGTA
CTCACCAGTCACAGAAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGGATAAAGTTGCAGGACCACTTCTGCGCTCGG
CCCTTCCGGCTGGCTGGTTTATTGCTGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATAGACAGATCGCTGAGATAGGTGCCTC
ACTGATTAAGCATTGGTAACTGTCAGACCAAGTTTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCACTGAGCGTCAGACCCCGTAGAAAAGATCAAAGG
ATCTTCTTGAGATCCTTTTTTTCTGCGCGTAATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACTGTCCTTCTAGTGTAGCCGTAGTTAGGCCAC
CACTTCAAGAACTCTGTAGCACCGCCTACATACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGGCGGAGCCTATGGAAAAACGCCAGCAACGCGGCCTTTTTACGGTTC
CTGGCCTTTTGCTGGCCTTTTGCTC

Plasmid AAVss-SPc5-12-MVM-hGAAco-SynthpA (SEQ ID NO: 10)

ACATGTCCTGCAGGCAGCTGCGCGCTCGCTCGCTCACTGAGGCCGCCCGGGCAAAGCCCGGGCGTCGGGCGACCTTTGGTCGCCCGGCC
TCAGTGAGCGAGCGAGCGCGCAGAGAGGGAGTGGCCAACTCCATCACTAGGGGTTCCTGCGGCCGCACGCGTACCGGGTACCCAACCC
GTTACGTGGCCACCGCCTTCGGCACCATCCTCACGACACCCAAATATGGCGACGGGTGAGGAATGGTGGGGAGTTATTTTTAGAGCGGT
GAGGAAGGTGGGCAGGCAGCAGGTGTTGGCGCTCTAAAAATAACTCCCGGGAGTTATTTTTAGAGCGGAGGAATGGTGGACACCCAAA
TATGGCGACGGTTCCTCACCCGTCGCCATATTTGGGTGTCCGCCCTCGGCCGGGGCCGCATTCCTGGGGGCCGGGCGGTGCTCCCGCCC
GCCTCGATAAAAGGCTCCGGGGCCGGCGGCGGCCCACGAGCTACCCGGAGGAGCGGGAGGCGCCAAGCTCTAGATCTAGAACTAGTA
AGAGGTAAGGGTTTAAGGGATGGTTGGTTGGTGGGGTATTAATGTTTAATTACCTGGAGCACCTGCCTGAAATCACTTTTTTTCAGGTTG
GCGTACGGCCACCATGGGCGTCAGACATCCTCCATGTTCTCACAGACTGCTGGCCGTGTGTGCTCTGGTGTCTCTTGCTACAGCTGCCCT
GCTGGGACATATCCTGCTGCACGATTTTCTGCTGGTGCCCAGAGAGCTGTCTGGCAGCTCTCCTGTGCTGGAAGAAACACACCCTGCACA
TCAGCAGGGCGCCTCTAGACCTGGACCTAGAGATGCTCAAGCCCATCCTGGCAGACCTAGAGCCGTGCCTACACAGTGTGACGTGCCAC
CTAACAGCAGATTCGACTGCGCCCCTGACAAGGCCATCACACAAGAGCAGTGTGAAGCCAGAGGCTGCTGCTACATTCCTGCCAAACAA
GGACTGCAGGGCGCTCAGATGGGACAGCCTTGGTGCTTCTTCCCACCATCTTACCCCAGCTACAAGCTGGAAAACCTGAGCAGCAGCGA
GATGGGCTACACCGCCACACTGACCAGAACCACACCTACATTCTTCCCAAAGGACATCCTGACACTGCGGCTGGACGTGATGATGGAAA
CCGAGAACCGGCTGCACTTCACCATCAAGGACCCCGCCAATAGAAGATACGAGGTGCCCCTGGAAACCCCTCACGTGCACTCTAGAGCC
CCATCTCCACTGTACAGCGTGGAATTCAGCGAGGAACCCTTTGGCGTGATCGTGCGGAGACAGCTGGATGGCAGAGTGCTGCTGAATAC
CACAGTGGCCCCTCTGTTCTTCGCCGACCAGTTTCTGCAGCTGAGCACAAGCCTGCCTAGCCAGTATATCACAGGCCTGGCCGAACACCT
GTCTCCACTGATGCTGAGCACCAGCTGGACCAGAATCACCCTGTGGAACAGAGATCTGGCCCCTACACCTGGCGCCAATCTGTACGGCTC
TCACCCTTTTTATCTGGCCCTGGAAGATGGCGGAAGCGCCCACGGTGTCTTTCTGCTGAACAGCAACGCCATGGACGTGGTGCTGCAACC
ATCTCCTGCTCTGTCTTGGAGAAGCACCGGCGGCATCCTGGACGTGTACATCTTTCTGGGACCCGAGCCTAAGAGCGTGGTGCAGCAGT
ATCTGGATGTCGTGGGCTACCCCTTCATGCCTCCTTATTGGGGCCTGGGCTTCCACCTGTGTAGATGGGGATACAGCTCCACCGCCATCAC
CAGACAGGTGGTGGAAAACATGACCCGGGCTCACTTCCCACTGGATGTGCAGTGGAACGACCTGGACTACATGGACTCCAGACGGGAC
TTCACCTTTAACAAGGACGGCTTCAGAGACTTCCCCGCCATGGTGCAAGAACTGCATCAAGGCGGCAGACGGTACATGATGATCGTGGA
TCCTGCCATCTCTTCTAGCGGCCCTGCCGGAAGCTACAGACCTTATGATGAGGGCCTGAGAAGAGGCGTGTTCATCACCAATGAGACAG
GCCAGCCTCTGATCGGCAAAGTGTGGCCTGGAAGCACCGCCTTTCCAGACTTCACCAATCCAACCGCTCTGGCTTGGTGGGAAGATATG
GTGGCCGAGTTCCACGATCAGGTGCCCTTCGATGGCATGTGGATCGACATGAACGAGCCCAGCAACTTCATCAGGGGCAGCGAGGATG
GCTGCCCCAACAACGAACTGGAAAATCCTCCTTACGTGCCAGGCGTTGTCGGAGGAACACTGCAGGCCGCCACAATTTGTGCCAGCAGC

Fig. 1D

CATCAGTTTCTGAGCACCCACTACAACCTGCACAACCTGTACGGCCTGACCGAGGCCATTGCCTCTCATAGAGCCCTGGTTAAGGCCAGA
GGCACCCGGCCTTTTGTGATCAGCAGAAGCACATTTGCCGGCCACGGCAGATATGCCGGACATTGGACAGGGGACGTTTGGTCTAGTTG
GGAGCAGCTGGCCTCTAGCGTGCCCGAGATCCTGCAGTTTAATCTGCTGGGAGTGCCCCTCGTGGGAGCCGATGTTTGTGGATTTCTGG
GCAACACCTCCGAGGAACTGTGCGTCAGATGGACACAGCTGGGCGCCTTCTATCCCTTCATGAGAAACCACAACAGCCTGCTGAGCCTG
CCTCAAGAGCCTTACAGCTTTAGCGAACCCGCACAGCAGGCCATGAGAAAGGCCCTGACTCTGAGATACGCTCTGCTGCCCCACCTGTAC
ACCCTGTTTCATCAAGCTCATGTGGCCGGCGAGACAGTGGCCAGACCACTGTTTCTGGAATTCCCCAAGGACAGCAGCACCTGGACAGT
GGATCATCAGCTGCTCTGGGGAGAAGCCCTGCTCATTACACCTGTGCTGCAGGCTGGCAAGGCCGAAGTGACAGGATACTTTCCCCTCG
GCACTTGGTACGACCTGCAGACAGTTCCTGTGGAAGCTCTGGGATCTCTGCCTCCACCTCCTGCTGCTCCTAGAGAGCCTGCCATTCACTC
TGAAGGCCAGTGGGTTACACTGCCCGCTCCACTGGACACCATCAATGTGCACCTGAGAGCCGGCTACATCATCCCTCTGCAAGGCCCTGG
ACTGACCACAACCGAAAGCAGACAGCAGCCAATGGCTCTGGCCGTGGCTCTGACAAAAGGCGGAGAAGCTAGAGGCGAACTGTTCTGG
GATGACGGCGAGAGCCTGGAAGTGCTGGAACGGGGAGCCTACACACAAGTGATCTTTCTCGCCCGGAACAACACCATCGTGAACGAAC
TCGTCAGAGTGACCAGTGAAGGTGCCGGACTGCAGCTCCAGAAAGTGACAGTGCTTGGAGTGGCCACAGCACCCCAGCAGGTTTTGTCT
AATGGCGTGCCCGTGTCCAACTTCACATACAGCCCTGACACCAAGGTGCTGGACATCTGTGTGTCTCTGCTGATGGGCGAGCAGTTCCTG
GTGTCCTGGTGTTGACCTAGGAATAAAAGATCTTTATTTTCATTAGATCTGTGTGTTGGTTTTTTGTGTGACCCGTCTGATTTTGTAGGTAA
CCACGTGCGGACCGAGCGGCCGCAGGAACCCCTAGTGATGGAGTTGGCCACTCCCTCTCTGCGCGCTCGCTCGCTCACTGAGGCCGGGC
GACCAAAGGTCGCCCGACGCCCGGGCTTTGCCCGGGCGGCCTCAGTGAGCGAGCGAGCGCGCAGCTGCCTGCAGGGGCGCCTGATGC
GGTATTTTCTCCTTACGCATCTGTGCGGTATTTCACACCGCATACGTCAAAGCAACCATAGTACGCGCCCTGTAGCGGCGCATTAAGCGC
GGCGGGTGTGGTGGTTACGCGCAGCGTGACCGCTACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGATTTAGTGCTTTACGGCACCTCGACCCCAAAAAAC
TTGATTTGGGTGATGGTTCACGTAGTGGGCCATCGCCCTGATAGACGGTTTTTCGCCCTTTGACGTTGGAGTCCACGTTCTTTAATAGTGG
ACTCTTGTTCCAAACTGGAACAACACTCAACCCTATCTCGGGCTATTCTTTTGATTTATAAGGGATTTTGCCGATTTCGGCCTATTGGTTAA
AAAATGAGCTGATTTAACAAAAATTTAACGCGAATTTTAACAAAATATTAACGTTTACAATTTTATGGTGCACTCTCAGTACAATCTGCTCT
GATGCCGCATAGTTAAGCCAGCCCCGACACCCGCCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGTCATCACCGAAACGCGCGAGACGAAAGGGCCTCGTGATACG
CCTATTTTTATAGGTTAATGTCATGATAATAATGGTTTCTTAGACGTCAGGTGGCACTTTTCGGGGAAATGTGCGCGGAACCCCTATTTGT
TTATTTTTCTAAATACATTCAAATATGTATCCGCTCATGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGTAAGATCCTTGAGAGTTTTCGCCCCGAAGA
ACGTTTTCCAATGATGAGCACTTTTAAAGTTCTGCTATGTGGCGCGGTATTATCCCGTATTGACGCCGGGCAAGAGCAACTCGGTCGCCG
CATACACTATTCTCAGAATGACTTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGGAGCTAACCGCTTTTTTGCACAA
CATGGGGGATCATGTAACTCGCCTTGATCGTTGGGAACCGGAGCTGAATGAAGCCATACCAAACGACGAGCGTGACACCACGATGCCTG
TAGCAATGGCAACAACGTTGCGCAAACTATTAACTGGCGAACTACTTACTCTAGCTTCCCGGCAACAATTAATAGACTGGATGGAGGCGG
ATAAAGTTGCAGGACCACTTCTGCGCTCGGCCCTTCCGGCTGGCTGGTTTATTGCTGATAAATCTGGAGCCGGTGAGCGTGGGTCTCGCG
GTATCATTGCAGCACTGGGGCCAGATGGTAAGCCCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGACCAAGTTTACTCATATATACTTTAGATTGATTTAA
AACTTCATTTTTAATTTAAAAGGATCTAGGTGAAGATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTGGCTTCAGCAGAGCGCAGATACCAAATACTG
TCCTTCTAGTGTAGCCGTAGTTAGGCCACCACTTCAAGAACTCTGTAGCACCGCCTACATACCTCGCTCTGCTAATCCTGTTACCAGTGGCT
GCTGCCAGTGGCGATAAGTCGTGTCTTACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCGTGAGCTATGAGAAAGCGCCACGCTTCCC
GAAGGGAGAAAGGCGGACAGGTATCCGGTAAGCGGCAGGGTCGGAACAGGAGAGCGCACGAGGGAGCTTCCAGGGGGAAACGCCTG
GTATCTTTATAGTCCTGTCGGGTTTCGCCACCTCTGACTTGAGCGTCGATTTTTGTGATGCTCGTCAGGGGGGCGGAGCCTATGGAAAAA
CGCCAGCAACGCGGCCTTTTTACGGTTCCTGGCCTTTTGCTGGCCTTTTGCTC plasmid AAVss-Dph-CRE02-CSkSH1-SPc5-12-MVM-hGAA-SynthpA (SEQ ID NO: 11)

ACATGTCCTGCAGGCAGCTGCGCGCTCGCTCGCTCACTGAGGCCGCCCGGGCAAAGCCCGGGCGTCGGGCGACCTTTGGTCGCCCGGCC
TCAGTGAGCGAGCGAGCGCGCAGAGAGGGAGTGGCCAACTCCATCACTAGGGGTTCCTGCGGCCGCACGCGTACCGGTGACAGGTGC
GGTTCCCGGAGCGCAGGCGCACACATGCACCCACCGGCGAACGCGGTGACCCTCGCCCCACCCCATCCCCTCCGGCGGGCAACTGGGTC

Fig. 1E

GGGTCAGGAGGGGCAAACCCGCTAGGGAGACACTCCATATACGGCCCGGCCCGCGTTACCTGGGACCGGGCCAACCCGCTCCTTCTTTG
GTCAACGCAGGGGACCCGGGCGGGGGCCCAGGCCGCGAACCGGCCGAGGGAGGGGGCTCTAGTGCCCAACACCCAAATATGGCTCGA
GAAGGGCAGCGACATTCCTGCGGGGTGGCGCGGAGGGAATGCCCGCGGGCTATATAAAACCTGAGCAGAGGGACAAGCGGCCACCGC
AGCGGACAGCGCCAAGTGAAGCCTCGCTTCCCCTCCGCGGCGACCAGGGCCCGAGCCGAGAGTAGCAGTTGTAGCTACCCGCCCAGGT
AGGGGCGCGCCACGCGTGTTCTCCTCTATAAATACCCGCTCTGGTATTTGGGGTTGGCAGCTGTTGCTGCCAGGGAGATGGTTGGGTTG
ACATGCGGCTCCTGACAAAACACAAACCCCTGGTGTGTGTGGGCGTGGGTGGTGTGAGTAGGGGGATGAATCAGGGAGGGGGCGGGG
GACCCAGGGGGCAGGAGCCACACAAAGTCTGTGCGGGGGTGGGAGCGCACATAGCAATTGGAAACTGAAAGCTTATCAGACCCTTTCT
GGAAATCAGCCCACTGTTTATAAACTTGAGGCCCCACCCTCGACAGTACCGGGGAGGAAGAGGGCCTGCACTAGTCCAGAGGGAAACT
GAGGCTCAGGGCTAGCTCGCCCATAGACATACATGGCAGGCAGGCTGGTACCCAACCCGTTACGTGGCCACCGCCTTCGGCACCATCCT
CACGACACCCAAATATGGCGACGGGTGAGGAATGGTGGGGAGTTATTTTTAGAGCGGTGAGGAAGGTGGGCAGGCAGCAGGTGTTGG
CGCTCTAAAAATAACTCCCGGGAGTTATTTTTAGAGCGGAGGAATGGTGGACACCCAAATATGGCGACGGTTCCTCACCCGTCGCCATAT
TTGGGTGTCCGCCCTCGGCCGGGGCCGCATTCCTGGGGGCCGGGCGGTGCTCCCGCCCGCCTCGATAAAAGGCTCCGGGGCCGGCGGC
GGCCCACGAGCTACCCGGAGGAGCGGGAGGCGCCAAGCTCTAGATCTAGAACTAGTAAGAGGTAAGGGTTTAAGGGATGGTTGGTTG
GTGGGGTATTAATGTTTAATTACCTGGAGCACCTGCCTGAAATCACTTTTTTTCAGGTTGGCGTACGGCCACCATGGGAGTGAGGCACCC
GCCCTGCTCCCACCGGCTCCTGGCCGTCTGCGCCCTCGTGTCCTTGGCAACCGCTGCACTCCTGGGGCACATCCTACTCCATGATTTCCTG
CTGGTTCCCCGAGAGCTGAGTGGCTCCTCCCCAGTCCTGGAGGAGACTCACCCAGCTCACCAGCAGGGAGCCAGCAGACCAGGGCCCCG
GGATGCCCAGGCACACCCCGGCCGTCCCAGAGCAGTGCCCACACAGTGCGACGTCCCCCCCAACAGCCGCTTCGATTGCGCCCCTGACA
AGGCCATCACCCAGGAACAGTGCGAGGCCCGCGGCTGTTGCTACATCCCTGCAAAGCAGGGGCTGCAGGGAGCCCAGATGGGGCAGCC
CTGGTGCTTCTTCCCACCCAGCTACCCCAGCTACAAGCTGGAGAACCTGAGCTCCTCTGAAATGGGCTACACGGCCACCCTGACCCGTAC
CACCCCCACCTTCTTCCCCAAGGACATCCTGACCCTGCGGCTGGACGTGATGATGGAGACTGAGAACCGCCTCCACTTCACGATCAAAGA
TCCAGCTAACAGGCGCTACGAGGTGCCCTTGGAGACCCCGCATGTCCACAGCCGGGCACCGTCCCCACTCTACAGCGTGGAGTTCTCCG
AGGAGCCCTTCGGGGTGATCGTGCGCCGGCAGCTGGACGGCCGCGTGCTGCTGAACACGACGGTGGCGCCCCTGTTCTTTGCGGACCA
GTTCCTTCAGCTGTCCACCTCGCTGCCCTCGCAGTATATCACAGGCCTCGCCGAGCACCTCAGTCCCCTGATGCTCAGCACCAGCTGGACC
AGGATCACCCTGTGGAACCGGGACCTTGCGCCCACGCCCGGTGCGAACCTCTACGGGTCTCACCCTTTCTACCTGGCGCTGGAGGACGG
CGGGTCGGCACACGGGGTGTTCCTGCTAAACAGCAATGCCATGGATGTGGTCCTGCAGCCGAGCCCTGCCCTTAGCTGGAGGTCGACAG
GTGGGATCCTGGATGTCTACATCTTCCTGGGCCCAGAGCCCAAGAGCGTGGTGCAGCAGTACCTGGACGTTGTGGGATACCCGTTCATG
CCGCCATACTGGGGCCTGGGCTTCCACCTGTGCCGCTGGGGCTACTCCTCCACCGCTATCACCCGCCAGGTGGTGGAGAACATGACCAG
GGCCCACTTCCCCCTGGACGTCCAGTGGAACGACCTGGACTACATGGACTCCCGGAGGGACTTCACGTTCAACAAGGATGGCTTCCGGG
ACTTCCCGGCCATGGTGCAGGAGCTGCACCAGGGCGGCCGGCGCTACATGATGATCGTGGATCCTGCCATCAGCAGCTCGGGCCCTGCC
GGGAGCTACAGGCCCTACGACGAGGGTCTGCGGAGGGGGGTTTTCATCACCAACGAGACCGGCCAGCCGCTGATTGGGAAGGTATGG
CCCGGGTCCACTGCCTTCCCCGACTTCACCAACCCCACAGCCCTGGCCTGGTGGGAGGACATGGTGGCTGAGTTCCATGACCAGGTGCCC
TTCGACGGCATGTGGATTGACATGAACGAGCCTTCCAACTTCATCAGGGGCTCTGAGGACGGCTGCCCCAACAATGAGCTGGAGAACCC
ACCCTACGTGCCTGGGGTGGTTGGGGGGACCCTCCAGGCGGCCACCATCTGTGCCTCCAGCCACCAGTTTCTCTCCACACACTACAACCT
GCACAACCTCTACGGCCTGACCGAAGCCATCGCCTCCCACAGGGCGCTGGTGAAGGCTCGGGGGACACGCCCATTTGTGATCTCCCGCT
CGACCTTTGCTGGCCACGGCCGATACGCCGGCCACTGGACGGGGGACGTGTGGAGCTCCTGGGAGCAGCTCGCCTCCTCCGTGCCAGA
AATCCTGCAGTTTAACCTGCTGGGGGTGCCTCTGGTCGGGGCCGACGTCTGCGGCTTCCTGGGCAACACCTCAGAGGAGCTGTGTGTGC
GCTGGACCCAGCTGGGGGCCTTCTACCCCTTCATGCGGAACCACAACAGCCTGCTCAGTCTGCCCCAGGAGCCGTACAGCTTCAGCGAG
CCGGCCCAGCAGGCCATGAGGAAGGCCCTCACCCTGCGCTACGCACTCCTCCCCCACCTCTACACACTGTTCCACCAGGCCCACGTCGCG
GGGGAGACCGTGGCCCGGCCCCTCTTCCTGGAGTTCCCCAAGGACTCTAGCACCTGGACTGTGGACCACCAGCTCCTGTGGGGGGAGGC
CCTGCTCATCACCCCAGTGCTCCAGGCCGGGAAGGCCGAAGTGACTGGCTACTTCCCCTTGGGCACATGGTACGACCTGCAGACGGTGC
CAGTAGAGGCCCTTGGCAGCCTCCCACCCCCACCTGCAGCTCCCCGTGAGCCAGCCATCCACAGCGAGGGGCAGTGGGTGACGCTGCCG
GCCCCCCTGGACACCATCAACGTCCACCTCCGGGCTGGGTACATCATCCCCCTGCAGGGCCCTGGCCTCACAACCACAGAGTCCCGCCAG
CAGCCCATGGCCCTGGCTGTGGCCCTGACCAAGGGTGGGGAGGCCCGAGGGGAGCTGTTCTGGGACGATGGAGAGAGCCTGGAAGTG
CTGGAGCGAGGGGCCTACACACAGGTCATCTTCCTGGCCAGGAATAACACGATCGTGAATGAGCTGGTACGTGTGACCAGTGAGGGAG
CTGGCCTGCAGCTGCAGAAGGTGACTGTCCTGGGCGTGGCCACGGCGCCCCAGCAGGTCCTCTCCAACGGTGTCCCTGTCTCCAACTTCA
CCTACAGCCCCGACACCAAGGTCCTGGACATCTGTGTCTCGCTGTTGATGGGAGAGCAGTTTCTCGTCAGCTGGTGTTAGCCTAGGAATA
AAAGATCTTTATTTTCATTAGATCTGTGTGTTGGTTTTTTGTGTGACCCGTCTGATTTTGTAGGTAACCACGTGCGGACCGAGCGGCCGCA
GGAACCCCTAGTGATGGAGTTGGCCACTCCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGGGGCGCCTGATGCGGTATTTTCTCCTTACGCATCTGTGC
GGTATTTCACACCGCATACGTCAAAGCAACCATAGTACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCTTTCTCGCCACGTTCGCCGGCTTTCCCCGTCAAGCT
CTAAATCGGGGGCTCCCTTTAGGGTTCCGATTTAGTGCTTTACGGCACCTCGACCCCAAAAAACTTGATTTGGGTGATGGTTCACGTAGT
GGGCCATCGCCCTGATAGACGGTTTTTCGCCCTTTGACGTTGGAGTCCACGTTCTTTAATAGTGGACTCTTGTTCCAAACTGGAACAACAC
TCAACCCTATCTCGGGCTATTCTTTTGATTTATAAGGGATTTTGCCGATTTCGGCCTATTGGTTAAAAAATGAGCTGATTTAACAAAAATTT
AACGCGAATTTTAACAAAATATTAACGTTTACAATTTTATGGTGCACTCTCAGTACAATCTGCTCTGATGCCGCATAGTTAAGCCAGCCCC
GACACCCGCCAACACCCGCTGACGCGCCCTGACGGGCTTGTCTGCTCCCGGCATCCGCTTACAGACAAGCTGTGACCGTCTCCGGGAGCT
GCATGTGTCAGAGGTTTTCACCGTCATCACCGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTATTTGTTTATTTTTCTAAATACATTCAAATAT
GTATCCGCTCATGAGACAATAACCCTGATAAATGCTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGAAAGTAAAAGATGCTGAAGATCAGTTGGGTGCAC

Fig. 1F

GAGTGGGTTACATCGAACTGGATCTCAACAGCGGTAAGATCCTTGAGAGTTTTCGCCCCGAAGAACGTTTTCCAATGATGAGCACTTTTA
AAGTTCTGCTATGTGGCGCGGTATTATCCCGTATTGACGCCGGGCAAGAGCAACTCGGTCGCCGCATACACTATTCTCAGAATGACTTGG
TTGAGTACTCACCAGTCACAGAAAAGCATCTTACGGATGGCATGACAGTAAGAGAATTATGCAGTGCTGCCATAACCATGAGTGATAAC
ACTGCGGCCAACTTACTTCTGACAACGATCGGAGGACCGAAGGAGCTAACCGCTTTTTTGCACAACATGGGGGATCATGTAACTCGCCTT
GATCGTTGGGAACCGGAGCTGAATGAAGCCATACCAAACGACGAGCGTGACACCACGATGCCTGTAGCAATGGCAACAACGTTGCGCA
AACTATTAACTGGCGAACTACTTACTCTAGCTTCCCGGCAACAATTAATAGACTGGATGGAGGCGGATAAAGTTGCAGGACCACTTCTGC
GCTCGGCCCTTCCGGCTGGCTGGTTTATTGCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGATGAACGAAATAGACAGATCGCTGAGATAGG
TGCCTCACTGATTAAGCATTGGTAACTGTCAGACCAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATACCAAATACTGTCCTTCTAGTGTAGCCGTAGTTA
GGCCACCACTTCAAGAACTCTGTAGCACCGCCTACATACCTCGCTCTGCTAATCCTGTTACCAGTGGCTGCTGCCAGTGGCGATAAGTCGT
GTCTTACCGGGTTGGACTCAAGACGATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGGGCGGAGCCTATGGAAAAACGCCAGCAACGCGGCCTTTTTA
CGGTTCCTGGCCTTTTGCTGGCCTTTTGCTC plasmid AAVss-SPc5-12-MVM-hGAAwt-SynthpA (SEQ ID NO: 12)

ACATGTCCTGCAGGCAGCTGCGCGCTCGCTCGCTCACTGAGGCCGCCCGGGCAAAGCCCGGGCGTCGGGCGACCTTTGGTCGCCCGGCC
TCAGTGAGCGAGCGAGCGCGCAGAGAGGGAGTGGCCAACTCCATCACTAGGGGTTCCTGCGGCCGCACGCGTACCGGTTGGCCACCGC
CTTCGGCACCATCCTCACGACACCCAAATATGGCGACGGGTGAGGAATGGTGGGGAGTTATTTTTAGAGCGGTGAGGAAGGTGGGCAG
GCAGCAGGTGTTGGCGCTCTAAAAATAACTCCCGGGAGTTATTTTTAGAGCGGAGGAATGGTGGACACCCAAATATGGCGACGGTTCCT
CACCCGTCGCCATATTTGGGTGTCCGCCCTCGGCCGGGGCCGCATTCCTGGGGGCCGGGCGGTGCTCCCGCCCGCCTCGATAAAAGGCT
CCGGGGCCGGCGGCGGCCCACGAGCTACCCGGAGGAGCGGGAGGCGCCAAGCTCTAGATCTAGAACTAGTAAGAGGTAAGGGTTTAA
GGGATGGTTGGTTGGTGGGGTATTAATGTTTAATTACCTGGAGCACCTGCCTGAAATCACTTTTTTTCAGGTTGGCGTACGGCCACCATG
GGAGTGAGGCACCCGCCCTGCTCCCACCGGCTCCTGGCCGTCTGCGCCCTCGTGTCCTTGGCAACCGCTGCACTCCTGGGGCACATCCTA
CTCCATGATTTCCTGCTGGTTCCCCGAGAGCTGAGTGGCTCCTCCCCAGTCCTGGAGGAGACTCACCCAGCTCACCAGCAGGGAGCCAGC
AGACCAGGGCCCCGGGATGCCCAGGCACACCCCGGCCGTCCCAGAGCAGTGCCCACACAGTGCGACGTCCCCCCCAACAGCCGCTTCGA
TTGCGCCCCTGACAAGGCCATCACCCAGGAACAGTGCGAGGCCCGCGGCTGTTGCTACATCCCTGCAAAGCAGGGGCTGCAGGGAGCC
CAGATGGGGCAGCCCTGGTGCTTCTTCCCACCCAGCTACCCCAGCTACAAGCTGGAGAACCTGAGCTCCTCTGAAATGGGCTACACGGCC
ACCCTGACCCGTACCACCCCCACCTTCTTCCCCAAGGACATCCTGACCCTGCGGCTGGACGTGATGATGGAGACTGAGAACCGCCTCCAC
TTCACGATCAAAGATCCAGCTAACAGGCGCTACGAGGTGCCCTTGGAGACCCCGCATGTCCACAGCCGGGCACCGTCCCCACTCTACAGC
GTGGAGTTCTCCGAGGAGCCCTTCGGGGTGATCGTGCGCCGGCAGCTGGACGGCCGCGTGCTGCTGAACACGACGGTGGCGCCCCTGT
TCTTTGCGGACCAGTTCCTTCAGCTGTCCACCTCGCTGCCCTCGCAGTATATCACAGGCCTCGCCGAGCACCTCAGTCCCCTGATGCTCAG
CACCAGCTGGACCAGGATCACCCTGTGGAACCGGGACCTTGCGCCCACGCCCGGTGCGAACCTCTACGGGTCTCACCCTTTCTACCTGGC
GCTGGAGGACGGCGGGTCGGCACACGGGGTGTTCCTGCTAAACAGCAATGCCATGGATGTGGTCCTGCAGCCGAGCCCTGCCCTTAGCT
GGAGGTCGACAGGTGGGATCCTGGATGTCTACATCTTCCTGGGCCCAGAGCCCAAGAGCGTGGTGCAGCAGTACCTGGACGTTGTGGG
ATACCCGTTCATGCCGCCATACTGGGGCCTGGGCTTCCACCTGTGCCGCTGGGGCTACTCCTCCACCGCTATCACCCGCCAGGTGGTGGA
GAACATGACCAGGGCCCACTTCCCCCTGGACGTCCAGTGGAACGACCTGGACTACATGGACTCCCGGAGGGACTTCACGTTCAACAAGG
ATGGCTTCCGGGACTTCCCGGCCATGGTGCAGGAGCTGCACCAGGGCGGCCGGCGCTACATGATGATCGTGGATCCTGCCATCAGCAGC
TCGGGCCCTGCCGGGAGCTACAGGCCCTACGACGAGGGTCTGCGGAGGGGGGTTTTCATCACCAACGAGACCGGCCAGCCGCTGATTG
GGAAGGTATGGCCCGGGTCCACTGCCTTCCCCGACTTCACCAACCCCACAGCCCTGGCCTGGTGGGAGGACATGGTGGCTGAGTTCCAT
GACCAGGTGCCCTTCGACGGCATGTGGATTGACATGAACGAGCCTTCCAACTTCATCAGGGGCTCTGAGGACGGCTGCCCCAACAATGA
GCTGGAGAACCCACCCTACGTGCCTGGGGTGGTTGGGGGGACCCTCCAGGCGGCCACCATCTGTGCCTCCAGCCACCAGTTTCTCTCCAC
ACACTACAACCTGCACAACCTCTACGGCCTGACCGAAGCCATCGCCTCCCACAGGGCGCTGGTGAAGGCTCGGGGGACACGCCCATTTG
TGATCTCCCGCTCGACCTTTGCTGGCCACGGCCGATACGCCGGCCACTGGACGGGGGACGTGTGGAGCTCCTGGGAGCAGCTCGCCTCC
TCCGTGCCAGAAATCCTGCAGTTTAACCTGCTGGGGGTGCCTCTGGTCGGGGCCGACGTCTGCGGCTTCCTGGGCAACACCTCAGAGGA
GCTGTGTGTGCGCTGGACCCAGCTGGGGGCCTTCTACCCCTTCATGCGGAACCACAACAGCCTGCTCAGTCTGCCCCAGGAGCCGTACA
GCTTCAGCGAGCCGGCCCAGCAGGCCATGAGGAAGGCCCTCACCCTGCGCTACGCACTCCTCCCCCACCTCTACACACTGTTCCACCAGG
CCCACGTCGCGGGGGAGACCGTGGCCCGGCCCCTCTTCCTGGAGTTCCCCAAGGACTCTAGCACCTGGACTGTGGACCACCAGCTCCTGT
GGGGGGAGGCCCTGCTCATCACCCCAGTGCTCCAGGCCGGGAAGGCCGAAGTGACTGGCTACTTCCCCTTGGGCACATGGTACGACCTG

Fig. 1G

CAGACGGTGCCAGTAGAGGCCCTTGGCAGCCTCCCACCCCCACCTGCAGCTCCCCGTGAGCCAGCCATCCACAGCGAGGGGCAGTGGGT
GACGCTGCCGGCCCCCCTGGACACCATCAACGTCCACCTCCGGGCTGGGTACATCATCCCCCTGCAGGGCCCTGGCCTCACAACCACAGA
GTCCCGCCAGCAGCCCATGGCCCTGGCTGTGGCCCTGACCAAGGGTGGGGAGGCCCGAGGGGAGCTGTTCTGGGACGATGGAGAGAG
CCTGGAAGTGCTGGAGCGAGGGGCCTACACACAGGTCATCTTCCTGGCCAGGAATAACACGATCGTGAATGAGCTGGTACGTGTGACC
AGTGAGGGAGCTGGCCTGCAGCTGCAGAAGGTGACTGTCCTGGGCGTGGCCACGGCGCCCCAGCAGGTCCTCTCCAACGGTGTCCCTG
TCTCCAACTTCACCTACAGCCCCGACACCAAGGTCCTGGACATCTGTGTCTCGCTGTTGATGGGAGAGCAGTTTCTCGTCAGCTGGTGTTA
GCCTAGGAATAAAAGATCTTTATTTTCATTAGATCTGTGTGTTGGTTTTTTGTGTGACCCGTCTGATTTTGTAGGTAACCACGTGCGGACC
GAGCGGCCGCAGGAACCCCTAGTGATGGAGTTGGCCACTCCCTCTCTGCGCGCTCGCTCGCTCACTGAGGCCGGGCGACCAAAGGTCGC
CCGACGCCCGGGCTTTGCCCGGGCGGCCTCAGTGAGCGAGCGAGCGCGCAGCTGCCTGCAGGGGCGCCTGATGCGGTATTTTCTCCTTA
CGCATCTGTGCGGTATTTCACACCGCATACGTCAAAGCAACCATAGTACGCGCCCTGTAGCGGCGCATTAAGCGCGGCGGGTGTGGTGG
TTACGCGCAGCGTGACCGCTACACTTGCCAGCGCCCTAGCGCCCGCTCCTTTCGCTTTCTTCCCTTCCTTTCTCGCCACGTTCGCCGGCTTT
CCCCGTCAAGCTCTAAATCGGGGGCTCCCTTTAGGGTTCCGATTTAGTGCTTTACGGCACCTCGACCCCAAAAAACTTGATTTGGGTGATG
GTTCACGTAGTGGGCCATCGCCCTGATAGACGGTTTTTCGCCCTTTGACGTTGGAGTCCACGTTCTTTAATAGTGGACTCTTGTTCCAAAC
TGGAACAACACTCAACCCTATCTCGGGCTATTCTTTTGATTTATAAGGGATTTTGCCGATTTCGGCCTATTGGTTAAAAAATGAGCTGATTT
AACAAAAATTTAACGCGAATTTTAACAAAATATTAACGTTTACAATTTTATGGTGCACTCTCAGTACAATCTGCTCTGATGCCGCATAGTTA
AGCCAGCCCCGACACCCGCCAACACCCGCTGACGCGCCCTGACGGGCTTGTCTGCTCCCGGCATCCGCTTACAGACAAGCTGTGACCGTC
TCCGGGAGCTGCATGTGTCAGAGGTTTTCACCGTCATCACCGAAACGCGCGAGACGAAAGGGCCTCGTGATACGCCTATTTTTATAGGTT
AATGTCATGATAATAATGGTTTCTTAGACGTCAGGTGGCACTTTTCGGGGAAATGTGCGCGGAACCCCTATTTGTTTATTTTTCTAAATAC
ATTCAAATATGTATCCGCTCATGAGACAATAACCCTGATAAATGCTTCAATAATATTGAAAAAGGAAGAGTATGAGTATTCAACATTTCCG
TGTCGCCCTTATTCCCTTTTTTGCGGCATTTTGCCTTCCTGTTTTTGCTCACCCAGAAACGCTGGTGAAAGTAAAAGATGCTGAAGATCAGT
TGGGTGCACGAGTGGGTTACATCGAACTGGATCTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTATTGACGCCGGGCAAGAGCAACTCGGTCGCCGCATACACTATTCTCAG
AATGACTTGGTTGAGTACTCACCAGTCACAGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAACCGCTTTTTTGCACAACATGGGGGATCATG
TAACTCGCCTTGATCGTTGGGAACCGGAGCTGAATGAAGCCATACCAAACGACGAGCGTGACACCACGATGCCTGTAGCAATGGCAACA
ACGTTGCGCAAACTATTAACTGGCGAACTACTTACTCTAGCTTCCCGGCAACAATTAATAGACTGGATGGAGGCGGATAAAGTTGCAGG
ACCACTTCTGCGCTCGGCCCTTCCGGCTGGCTGGTTTATTGCTGATAAATCTGGAGCCGGTGAGCGTGGGTCTCGCGGTATCATTGCAGC
ACTGGGGCCAGATGGTAAGCCCTCCCGTATCGTAGTTATCTACACGACGGGGAGTCAGGCAACTATGGATGAACGAAATAGACAGATCG
CTGAGATAGGTGCCTCACTGATTAAGCATTGGTAACTGTCAGACCAAGTTTACTCATATATACTTTAGATTGATTTAAAACTTCATTTTTAA
TTTAAAAGGATCTAGGTGAAGATCCTTTTTGATAATCTCATGACCAAAATCCCTTAACGTGAGTTTTCGTTCCACTGAGCGTCAGACCCCG
TAGAAAAGATCAAAGGATCTTCTTGAGATCCTTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGCGCAGATACCAAATACTGTCCTTCTAGTGTAG
CCGTAGTTAGGCCACCACTTCAAGAACTCTGTAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCTATGAGAAAGCGCCACGCTTCCCGAAGGGAGAAAG
GCGGACAGGTATCCGGTAAGCGGCAGGGTCGGAACAGGAGAGCGCACGAGGGAGCTTCCAGGGGGAAACGCCTGGTATCTTTATAGT
CCTGTCGGGTTTCGCCACCTCTGACTTGAGCGTCGATTTTTGTGATGCTCGTCAGGGGGGCGGAGCCTATGGAAAAACGCCAGCAACGC
GGCCTTTTTACGGTTCCTGGCCTTTTGCTGGCCTTTTGCTC

Fig. 7
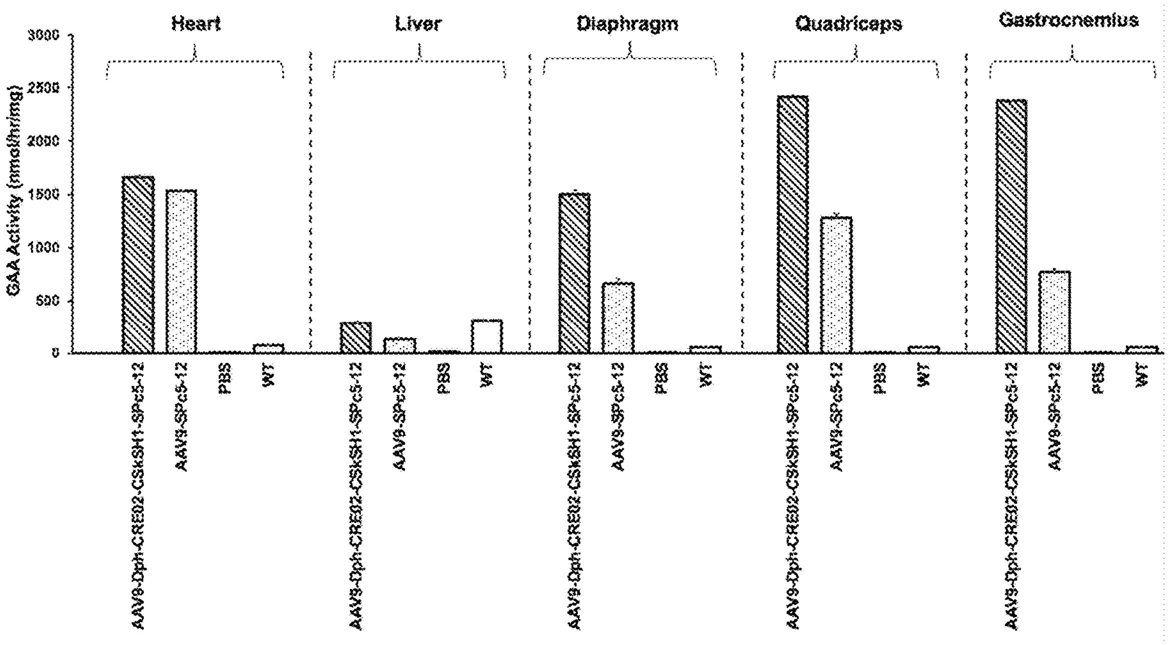
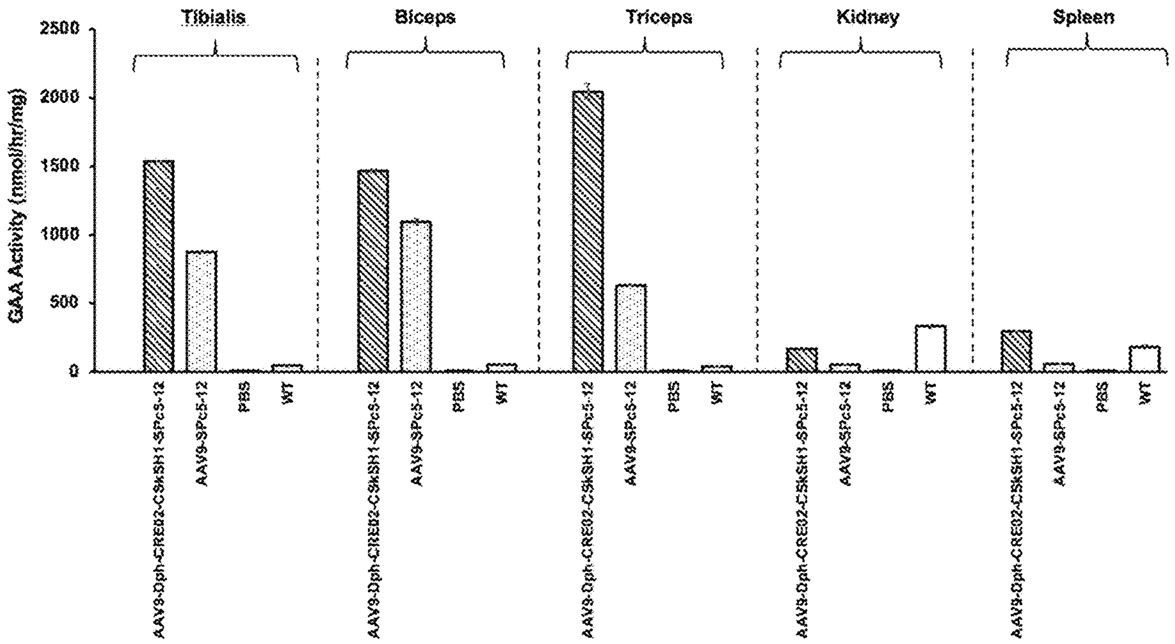

COMBINATION OF NUCLEIC ACID REGULATORY ELEMENTS AND METHODS AND USES THEREOF

CROSS-REFERENCE TO RELATED APPLICATIONS

This application is the U.S. National Phase under 35 U.S.C. § 371 of International Application No. PCT/EP2021/053939, filed Feb. 18, 2021, which claims priority to European Patent Application No. 20158064.4, filed Feb. 18, 2020, the entire content of which is incorporated herein by reference.

SEQUENCE LISTING STATEMENT

The present application contains a Sequence Listing, being submitted via Patent Center on even date herewith. The Sequence Listing is submitted in a file entitled "DECLE69.020APC_SEQLISTING.txt," which was created on Aug. 11, 2022, and is approximately 65 bytes in size. This Sequence Listing is hereby incorporated by reference.

FIELD

The present invention relates to a combination of nucleic acid regulatory elements that is able to enhance muscle-specific expression of genes, more particularly, to enhance expression of genes in diaphragm, skeletal muscle, heart tissue and smooth muscle, preferably in diaphragm, skeletal muscle and heart tissue. The invention further encompasses methods employing this combination of regulatory elements and the use thereof. Also encompassed by the invention are expression cassettes, vectors and pharmaceutical compositions comprising this combination of regulatory elements. The present invention is particularly useful for applications using gene therapy, more particularly muscle-directed gene therapy, even more particularly gene therapy directed to diaphragm, skeletal muscle, heart tissue and smooth muscle, and even more particularly gene therapy directed to diaphragm, skeletal muscle and heart tissue.

BACKGROUND

Muscle is an attractive target for gene therapy. Gene delivery to muscle can be used to augment expression of muscle structural proteins, such as dystrophin and sarcoglycans, or secreted proteins, such as follistatin e.g. to treat muscular dystrophy. In addition, muscle can be used as a therapeutic platform to express non-muscle secretory/regulatory pathway proteins for diabetes, atherosclerosis, hemophilia, cancer, etc. Also hereditary disorders that are due to a gene defect that impairs the function of skeletal muscle, heart and/or diaphragm, such as lysosomal storage disorders like Pompe disease, Fabry disease and Danon disease may benefit from muscle-specific gene therapy.

Pompe disease (also referred to as glycogen storage disorder type II or GSD II) mainly affects skeletal muscle, diaphragm and heart. GSD II results in deficiency of the lysosomal enzyme (acid) α-glucosidase (GAA) that leads to a lysosomal storage defect. In GSD II patients, glycogen cannot be broken down effectively into glucose. The accumulation of glycogen in GSD II patients causes myopathy with progressive muscle weakness. Without medical intervention, patients suffering from the most severe form of GSD II die because of respiratory failure within the first year of life. Alpha glucosidase enzyme replacement therapy (ERT) using recombinant human GAA (rhGAA ERT) is the only approved treatment for Pompe disease. Alpha glucosidase has provided irrefutable clinical benefits, but has not been an optimal treatment primarily due to poor drug targeting of ERT to skeletal muscles. Hence, developing an effective clinical therapy which is muscle-specific for Pompe disease represents an urgent unmet medical need.

Gene therapy provides an unprecedented opportunity to simultaneously treat dysfunction and degeneration of the muscle (including e.g. skeletal muscle, heart, diaphragm and smooth muscle), thanks to its ability to deliver therapeutic genes to the affected tissues in order to obtain a lasting therapeutic response. Despite its promise, the drawback is that relatively high virus vector dose is required to achieve a desirable therapeutic effect, thus impeding possible clinical translation. More particularly, gene therapy to the muscle is relatively inefficient due to limitations in gene delivery and gene expression. Moreover, immune responses specific for the therapeutic gene product curtail the efficiency of gene therapy applications directed towards muscle cells and tissues.

The challenges that hamper clinical translation and preclude the development of an effective cure for Pompe disease by gene therapy also relate to: (i) insufficient expression of the therapeutic transgene in the affected muscle cells and tissues; and (ii) the potential toxicity and untoward immune responses due to very high doses of conventional vectors needed to reach the main muscle groups (i.e. skeletal muscle, heart and diaphragm) affected by this life-threatening disease to effectively treat the different clinical manifestations of this diseases including myopathy with progressive muscle weakness.

Efforts to deliver transgenes to muscle cells and tissues have focused on vectors derived from adenoviruses, retroviruses, lentiviruses, and adeno-associated viruses (AAV), and plasmids. The adeno-associated viral (AAV) vector is by far the most promising gene delivery vehicle for muscle-directed gene therapy. AAV's natural tropism to muscle cells, their long-term persistent transgene expression, their multiple serotypes, as well as their minimal immune response have made AAV vectors well suited for muscle-directed gene therapy. AAV vector can be delivered into skeletal muscle, diaphragm, cardiac muscle and smooth muscle by means of local, regional, and systemic administrations.

Nevertheless, there remain concerns regarding the efficacy and safety of some gene delivery approaches. The major limiting factors are: insufficient and/or transient transgene expression levels, and inappropriate expression of the transgene in unwanted cell types. In particular, it has been shown that inadvertent transgene expression in antigen-presenting cells (APCs), increases the risk of untoward immune responses against the gene-modified cells and/or the therapeutic transgene product that consequently curtails long-term gene expression.

Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take into account the importance of including evolutionary conserved regulatory motifs into the expression modules, which is particularly relevant for clinical translation.

A computational approach depending upon a modified distance difference matrix (DDM)—multidimensional scaling (MDS) strategy (De Bleser et al. 2007. Genome Biol 8, R83) has proven to be useful for the in silico identification of clusters of evolutionary conserved transcription factor binding site (TFBS) motifs associated with robust tissue-specific expression in liver (WO 2009/130208) and heart (WO2011/051450). Furthermore, novel and robust human cis-regulatory elements (CREs) were obtained via genome-wide data-mining and yielded robust specific transgene expression levels in diaphragm or heart and skeletal muscle while avoiding expression in non-target tissues (WO 2015/110449 A1 and WO 2018/178067 A1).

However, just expressing the therapeutic protein in the muscle, heart or diaphragm using these CREs may not be sufficient, particularly since there is a need to further diminish the vector doses to levels that do not provoke any unwanted toxicity, such as the well-documented liver toxicity that occurred in most if not all of the gene therapy trials that were based on high vector dose that were systemically administered to the patients.

Thus, there remains a need in the art for safe and efficient gene delivery to muscle. For example, it is imperative to further improve the efficacy and safety of tissue-targeted gene therapy applications for Pompe disease, ideally by developing more robust gene therapy vectors that allow for high and widespread diaphragm, heart and skeletal muscle-specific expression of the GAA transgene at lower and thus safer vector doses.

SUMMARY OF THE INVENTION

To address the challenges with current gene therapy applications, present inventors developed a novel combination of transcriptional cis-regulatory modules or elements (CREs) that confers unexpectedly high expression in muscle, particularly skeletal muscle, heart, diaphragm and/or smooth muscle, even more particularly skeletal muscle, heart and/or diaphragm. More particularly, present inventors designed expression vectors comprising a specific combination of CREs that target human diaphragm (Dph-CRE) or cardiac and skeletal muscle (also referred to herein as CSk-CRE or CSk-SH-CRE or CSk-SH or CskSH or CSKSH; SK, Sk or sk are interchangeable; the presence of hyphens between CSk, SH and/or CRE is optional), preferably in conjunction with a potent muscle-specific promotor. As shown in the experimental section, the inventors found that the use of a new nucleic acid regulatory element comprising a combination of (i) a diaphragm-specific nucleic acid regulatory element comprising a sequence having at least 80% identity to the sequence defined by SEQ ID NO: 1 (such as Dph-CRE02 previously identified in international patent application WO 2018/178067), or a functional fragment thereof, and (ii) a cardiac and skeletal muscle-specific nucleic acid regulatory element comprising a sequence having at least 80% identity to the sequence defined by SEQ ID NO: 2 (such as CskSH1 previously identified in international patent application WO 2015/110449), or a functional fragment thereof allows a robust multiple tissue specific gene expression of a target gene (e.g. GAA), in muscle, particularly in skeletal muscle, heart, diaphragm and smooth muscle, more particularly in skeletal muscle, heart and diaphragm. This approach hence, allows for the use of lower and thus safer vector doses, while maximizing therapeutic efficacy.

The invention therefore provides the following aspects:

Aspect 1. A nucleic acid regulatory element for enhancing muscle-specific gene expression comprising, consisting essentially of, or consisting of (i) a diaphragm-specific nucleic acid regulatory element comprising, consisting essentially of, or consisting of a sequence having at least 95% identity to the sequence defined by SEQ ID NO: 1 (e.g. Dph-CRE02), or a functional fragment thereof, and (ii) a cardiac and skeletal muscle-specific nucleic acid regulatory element comprising, consisting essentially of, or consisting of a sequence having at least 95% identity to the sequence defined by SEQ ID NO: 2 (e.g. CSk-SH1), or a functional fragment thereof.

Aspect 2. The nucleic acid regulatory element according to aspect 1, comprising, consisting essentially of, or consisting of the nucleotide sequence as set forth in SEQ ID NO: 3.

Aspect 3. A nucleic acid expression cassette comprising the nucleic acid regulatory element according to aspect 1 or 2 operably linked to a promoter.

Aspect 4. The nucleic acid expression cassette according to aspect 3, wherein the nucleic acid regulatory element is operably linked to a promoter and a transgene.

Aspect 5. The nucleic acid expression cassette according to aspect 3 or 4, wherein the promoter is a muscle-specific promoter, preferably a muscle-specific promoter selected from the group consisting of the desmin (DES) promoter; the synthetic SPc5-12 promoter (SPc5-12); the alpha-actin1 promoter (ACTA1); the Creatine kinase, muscle (CKM) promoter; the Four and a half LIM domains protein 1 (FHL1) promoter; the alpha 2 actinin (ACTN2) promoter; the filamin-C (FLNC) promoter; the sarcoplasmic/endoplasmic reticulum calcium ATPase 1 (ATP2A1) promoter; the Troponin I Type 1 (TNNI1) promoter; the Troponin I Type 2 (TNNI2) promoter; the Troponin T Type 3 (TNNT3) promoter; the myosin-1 (MYH1) promoter; the phosphorylatable, fast skeletal muscle myosin light chain (MYLPF) promoter; the Tropomyosin 1 (TPM1) promoter; the Tropomyosin 2 (TPM2) promoter; the alpha-3 chain tropomyosin (TPM3) promoter; the ankyrin repeat domain-containing protein 2 (ANKRD2) promoter; the myosin heavy-chain (MHC) promoter; the myosin light-chain (MLC) promoter; the muscle creatine kinase (MCK) promoter; the Myosin, Light Chain 1 (MYL1) promoter; the Myosin, Light Chain 2 (MYL2) promoter; the Myoglobin (MB) promoter; the Troponin T type 2, cardiac type (TNNT2) promoter; the Troponin C Type 2 (fast) (TNNC2) promoter; the Troponin C Type 1 (TNNC1) promoter; the Titin-Cap (TCAP) promoter; the Myosin, Heavy Chain 7 (MYH7) promoter; the Aldolase A (ALDOA) promoter; the dMCK promoter; the tMCK promoter; the MHCK7 promoter; the Troponin T Type 1 (TNNT1) promoter; the myosin-2 (MYH2) promoter; the sarcolipin (SLN) promoter; the myosin binding protein C1 (MYBPC1) promoter; the enolase (EN03) promoter; the alpha myosin heavy chain promoter (αMHC) promoter; the carbonic anhydrase 3 (CA3) promoter; the myosin heavy chain 11 (Myh11) promoter; the transgelin (Tagln) promoter and the actin alpha 2 smooth muscle (Acta2) promoter.

Aspect 6. The nucleic acid expression cassette according to any one of aspects 3 to 5, wherein the promoter is the SPc5-12 promoter, preferably the Spc5-12 promoter as defined by SEQ ID NO: 4.

Aspect 7. The nucleic acid expression cassette according to any one of aspects 3 to 5, wherein the promoter is the desmin promoter, preferably the desmin promoter as defined by SEQ ID NO: 22.

Aspect 8. The nucleic acid expression cassette according to any one of aspects 3 to 5, wherein the promoter is the MHCK7 promoter, preferably the MHCK7 promoter as defined by SEQ ID NO: 23.

Aspect 9. The nucleic acid expression cassette according to any one of aspects 3 to 8, wherein the transgene encodes a therapeutic protein.

Aspect 10. The nucleic acid expression cassette according to any one of aspects 3 to 9, wherein the transgene is codon-optimized.

Aspect 11. The nucleic acid expression cassette according to any one of aspects 3 to 10, wherein the transgene encodes a lysosomal protein, preferably a lysosomal protein selected from the group consisting of acid α-glucosidase (GAA), α-galactosidase A and LAMP2, preferably human GAA as defined by SEQ ID NO: 5, more preferably the codon-optimised human GAA (hGAAco) as defined by SEQ ID NO: 6.

Aspect 12. The nucleic acid expression cassette according to any one of aspects 3 to 11, further comprising an intron, preferably the Minute Virus of Mouse (MVM) intron as defined by SEQ ID NO: 7.

Aspect 13. The nucleic acid expression cassette according to any one of aspects 3 to 12, further comprising a polyadenylation signal, preferably a synthetic polyadenylation signal as defined by SEQ ID NO: 8.

Aspect 14. A vector comprising the nucleic acid expression cassette according to any one of aspects 3 to 13.

Aspect 15. The vector according to aspect 14, which is a viral vector, preferably an adeno-associated viral (AAV) vector, more preferably an AAV9 or AAV8 vector.

Aspect 16. The vector according to aspect 14 or 15, comprising (i) a diaphragm-specific nucleic acid regulatory element comprising a sequence having at least 95% identity to the sequence defined by SEQ ID NO: 1 (e.g. Dph-CRE02), or a functional fragment thereof; (ii) a cardiac and skeletal muscle-specific nucleic acid regulatory element comprising a sequence having at least 95% identity to the sequence defined by SEQ ID NO: 2 (e.g. CSk-SH1), or a functional fragment thereof; (iii) the MVM intron as defined by SEQ ID NO: 7; (iv) the SPc5-12 promoter as defined by SEQ ID NO: 4; (v) the human GAA transgene as defined by SEQ ID NO: 5 or the codon-optimised variant thereof as defined by SEQ ID NO: 6; and (vi) the synthetic poly A site as defined by SEQ ID NO: 8, preferably wherein the vector comprises, consists essentially of or consists of a sequence as defined by SEQ ID NO: 9 or SEQ ID NO: 11, preferably SEQ ID NO: 9.

Aspect 17. A pharmaceutical composition comprising the nucleic acid expression cassette according to any one of aspects 3 to 13, or the vector according to any one of aspects 14 to 16, and a pharmaceutically acceptable carrier.

Aspect 18. The nucleic acid expression cassette according to any one of aspects 3 to 13, the vector according to any one of aspects 14 to 16, or the pharmaceutical composition according to aspect 17, for use in medicine.

Aspect 19. The nucleic acid expression cassette according to any one of aspects 3 to 13, the vector according to any one of aspects 14 to 16, or the pharmaceutical composition according to aspect 17, for use in gene therapy, preferably muscle-directed gene therapy. For example, the gene therapy may be for a disease or disorder selected from lysosomal storage diseases (e.g. Fabry disease) including glycogen storage disorders (e.g. Pompe disease glycogen storage disorder (GSD) type II, Danon disease, glycogen storage disorder (GSD) type IIb, GSD III or GSD 3 (also known as Cori's disease or Forbes' disease), GSD IV or GSD4 (also known as Andersen disease), GSD V or GSD5 (also known as McArdle disease), GSD VII or GSD7 (also known as Tarui's disease), GSD X or GSD10, GSD XII or GSD 12 (also known as Aldolase A deficiency), GSD XIII or GSD13, GSD XV or GSD15) and mucopolysaccharidosis disorders (e.g. Hunter syndrome, Sanfilippo syndrome, mucopolyssacharidose (MPS) I, MPS II, MPS III, MPS IIIA, MPS IIIB, MPS IIIC, MPS IV, MPS VI, MPS VII, MPS IX); mitochondrial disorders (e.g. Barth syndrome); channelopathy (e.g. Brugada syndrome); metabolic disorders; myotubular myopathy (MTM); muscular dystrophy (e.g. Duchenne muscular dystrophy (DMD), Becker muscular dystrophy (BMD)); myotonic dystrophy; Myotonic Muscular Dystrophy (DM); Miyoshi myopathy; Fukuyama type congenital; dysferlinopathies; neuromuscular disease; motor neuron diseases (MND) (e.g. Charcot-Marie-Tooth disease (CMT), spinal muscular atrophy (SMA) or amyotrophic lateral sclerosis (ALS)); Emery-Dreifuss muscular dystrophy; facioscapulohumeral muscular dystrophy (FSHD); congenital muscular dystrophies; congenital myopathies; limb girdle muscular dystrophy (e.g. Limb Girdle Muscular Dystrophy type 2E (LGMD2E), Limb Girdle Muscular Dystrophy type 2D (LGMD2D), Limb Girdle Muscular Dystrophy type 2C (LGMD2C), Limb Girdle Muscular Dystrophy type 2B (LGMD2B), Limb Girdle Muscular Dystrophy type 2L (LGMD2L), Limb Girdle Muscular Dystrophy type 2A (LGMD2A)); metabolic myopathies; muscle inflammatory diseases; myasthenia; mitochondrial myopathies; anomalies of ionic channels; nuclear envelop diseases; cardiomyopathies; cardiac hypertrophy; heart failure; distal myopathies; hemophilia (e.g. hemophilia A and B); diabetes; cardiovascular diseases; and heart diseases Aspect 20: the nucleic acid regulatory element, the nucleic acid expression cassette, the vector, or the pharmaceutical composition for use according to aspect 19, wherein the gene therapy is for treating muscle-related disorders in general, alleviating the symptoms of myopathies in general and/or restoring the function of muscle cells in general.

Aspect 21: the nucleic acid regulatory element, the nucleic acid expression cassette, the vector, or the pharmaceutical composition for use according to aspect 19, wherein the gene therapy is for treating cardiovascular diseases. Non-limiting examples of cardiovascular diseases include atherosclerosis; arteriosclerosis; coronary heart disease; coronary artery disease; peripheral arterial disease; congenital heart disease; congestive heart failure; heart failure (also known as cardiac insufficiency); myocardial infarction (also known as heart attack); cardiac ischemia; acute coronary syndrome; unstable angina; stable angina; cardiomyopathy; hypertrophic cardiomyopathy; dilated cardiomyopathy; restrictive cardiomyopathy; primary cardiomyopathies caused by genetic mutations such as Brugada syndrome, Pompe disease, Danon disease and Fabry disease; cardiac amyloidosis (also known as stiff heart syndrome); myocarditis (also known as inflammatory cardiomyopathy); valvular heart disease; valvular stenosis; valvular insufficiency; endocarditis; rheumatic heart disease; pericarditis (i.e. a disease caused by an inflammation and/or infection of the pericardium); cardiac tamponade (also known as pericardial tamponade); cardiac arrhythmia; hypertension; hypotension; vessel stenosis; valve stenosis; or restenosis).

Aspect 22: A nucleic acid regulatory element according to aspect 1 or 2, a nucleic acid expression cassette according to any one of aspects 3 to 13, wherein the transgene encodes a lysosomal protein, preferably a lysosomal protein selected from the group consisting of acid α-glucosidase (GAA), α-galactosidase A and LAMP2; a vector according to aspect 14 or 15 comprising said nucleic acid expression cassette; or a pharmaceutical composition according to aspect 17 comprising said nucleic acid expression cassette or said vector, for use in the treatment of a lysosomal storage disease, preferably a lysosomal storage disease selected from the group consisting of Pompe disease, Fabry disease and Danon disease.

Aspect 23: A nucleic acid regulatory element according to aspect 1 or 2, a nucleic acid expression cassette according to any one of aspects 3 to 13, wherein the transgene encodes human GAA as defined by SEQ ID NO: 5, more preferably the codon-optimised human GAA (hGAAco) as defined by SEQ ID NO: 6, a vector according to any one of aspects 14 to 16, or a pharmaceutical composition according to aspect 16 for use in the treatment of Pompe disease.

Aspect 24. Use, preferably an in vitro or ex vivo use, of the nucleic acid regulatory element according to aspect 1 or 2, the nucleic acid expression cassette according to any one of aspects 3 to 13, or the vector according to any one of aspects 14 to 16 for enhancing gene expression in muscle, preferably for enhancing gene expression in diaphragm, skeletal muscle, heart tissue and smooth muscle, more preferably for enhancing gene expression in diaphragm, skeletal muscle and heart tissue.

Aspect 25. A method, preferably an in vitro or ex vivo method, for expressing a transgene product in muscle cells, preferably in diaphragm, skeletal muscle, heart cells and smooth muscle cells, more preferably in diaphragm, skeletal muscle, and heart cells, comprising:

introducing the nucleic acid expression cassette according to any one of aspects 3 to 13, or the vector according to any one of aspects 14 to 16, into said cells; and expressing the transgene product in the muscle cells.

BRIEF DESCRIPTION OF DRAWINGS

FIGS. 1A-1G: Collectively illustrate AAVss-Dph-CRE02-CSk-SH1-SPc5-12-MVM-hGAAco-pA (SEQ ID NO: 9) and AAVss-SPc5-12-MVM-hGAAco-pA (SEQ ID NO: 10) vector designs and sequences.

FIG. 7: GAA activity in GAA KO-mice injected with AAVss-Dph-CRE02-CSkSH1-SPc5 MVM-hGAAco-pA (SEQ ID NO: 9) ("AAV9-Dph-CRE02-CSkSH1-SPc5-12"), AAVss-SPc5 MVM-hGAAco-pA (SEQ ID NO: 10) ("AAV9-SPc5-12"), PBS and non-injected WT GAA+/+ mice.

DESCRIPTION

Figure 2:
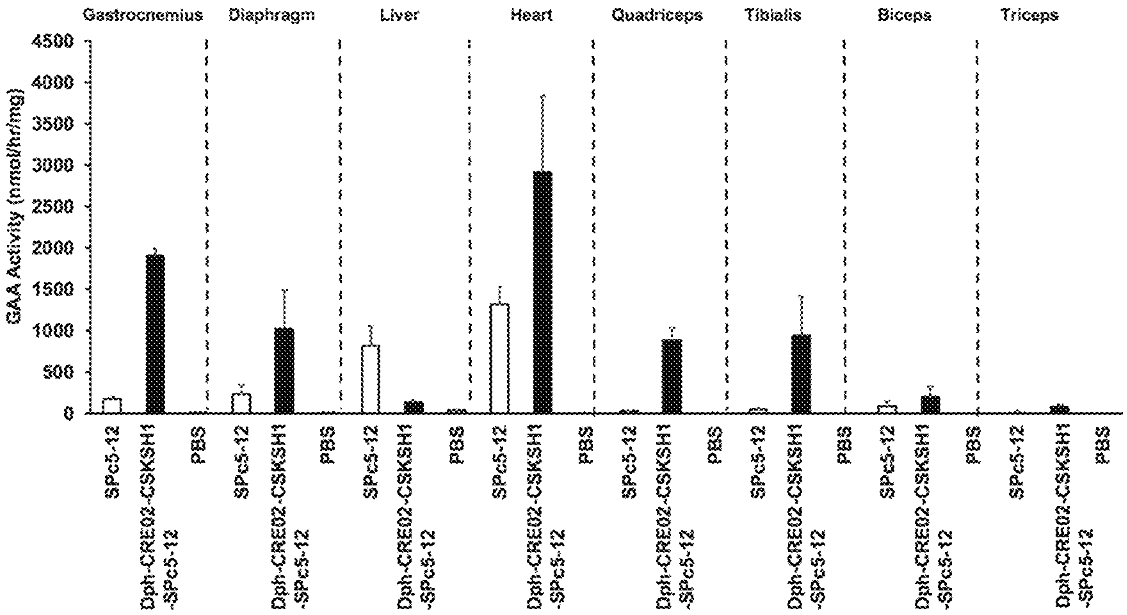
FIG. 2: GAA activity in GAA KO-mice injected with AAVss-Dph-CRE02-CSkSH1-SPc5-12-MVM-hGAAco-pA (SEQ ID NO: 9) ("Dph-CRE02-CSKSH1-SPc5-12"), AAVss-SPc5-12-MVM-hGAAco-pA (SEQ ID NO: 10) ("SPc5-12") or PBS

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass consisting of and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any or etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

For general methods relating to the invention, reference is made inter alia to well-known textbooks, including, e.g., "Molecular Cloning: A Laboratory Manual, 4$^{th}$ Ed." (Green and Sambrook, 2012, Cold Spring Harbor Laboratory Press), "Current Protocols in Molecular Biology" (Ausubel et al., 1987).

The inventors found to that the use of a novel nucleic acid regulatory element comprising a combination of (i) a diaphragm-specific nucleic acid regulatory element comprising a sequence having at least 80%, preferably a least 95%, more preferably 100%, sequence identity to the sequence defined by SEQ ID NO: 1 (such as Dph-CRE02 previously identified in international patent application WO 2018/178067 also denoted herein as "Dph-CRE-02" or "DphCRE02" or "DphCRE02" or "CRE02" or "CRE-02"), or a functional fragment thereof, and (ii) a cardiac and skeletal muscle-specific nucleic acid regulatory element comprising a sequence having at least 80%, preferably at least 95%, more preferably 100%, sequence identity to the sequence defined by SEQ ID NO: 2 (such as CskSH1 previously identified in international patent application WO 2015/110449, also denoted herein as "CSk-SH1" or "CSkSH1" or "Csk-SH1" or "CskSH1" or "CSK-SH1" or "CSKSH1"; "SK", "Sk" or "sk" are interchangeable; the presence of a hyphen between "CSk" and "SH1" is optional), or a functional fragment thereof allows a robust multiple tissue-specific gene expression of a target gene (e.g. GAA), in muscle, particularly in skeletal muscle, heart and/or diaphragm. More particularly, the inventors designed an AAV vector that expresses human codon-optimized GAA cDNA (hGAAco) as defined by SEQ ID NO: 6 using a combination of a diaphragm-specific nucleic acid regulatory element defined by SEQ ID NO: 1 and a cardiac and skeletal muscle-specific nucleic acid regulatory element as defined by SEQ ID NO: 2 in conjunction with muscle-specific promotor SPc5-12 as defined by SEQ ID NO: 4 as a gene therapy strategy for Pompe disease. This novel vector was validated in vivo in a clinically relevant mouse model of Pompe disease (i.e. GAA-deficient mice) yielding unexpectedly high and tissue-specific hGAAco activity in muscle, particularly in heart, skeletal muscle, diaphragm and smooth muscle, more particularly in heart, skeletal muscle and diaphragm. Furthermore, the increased hGAAco activity correlates with a reduction in glycogen accumulation, which demonstrates a phenotypic correction in the Pompe mice.

Accordingly, disclosed herein is a synthetic nucleic acid regulatory element for enhancing muscle-specific gene expression comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of (i) a diaphragm-specific nucleic acid regulatory element comprising, consisting essentially of, or consisting of a sequence as defined by SEQ ID NO: 1; a sequence having at least 80%, preferably at least 85%, more preferably at least 90%, even more preferably at least 95%, such as 95%, 96%, 97%, 98%, or 99%, identity to the sequence defined by SEQ ID NO: 1; or a functional fragment of a sequence as defined by SEQ ID NO: 1, and (ii) a cardiac and skeletal muscle-specific nucleic acid regulatory element comprising consisting essentially of, or consisting of a sequence as defined by SEQ ID NO: 2; a sequence having at least 80%, preferably at least 85%, more preferably at least 90%, even more preferably at least 95%, such as 95%, 96%, 97%, 98%, or 99%, identity to the sequence defined by SEQ ID NO: 2; or a functional fragment of a sequence as defined by SEQ ID NO: 2, also referred to herein as "Dph-CSk nucleic acid regulatory element" or "Dph-CSk-CRE".

A "nucleic acid regulatory element" or "regulatory element", also called "CRE" (cis-regulatory element), "CRM" (cis-regulatory module), or "SH" as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a muscle-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate or even within the gene or open reading frame itself. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory elements hence have a sequence which is only a small part of the naturally occurring genomic sequence and hence is not naturally occurring as such, but is isolated therefrom.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for E2A, HNH1, NF1, C/EBP, LRF, MyoD, SREBP; STAT-1, EGR1, EGR2, EGR3, EGR4, TBP, MEF-2A, NFYA, SIN3A, TCF12, PHF8, IRF1, EZH2, SUZ12, TBP, FOLR2A, REST, TEAD4, RBBP5, MSX-1, SRF and SIN3A. Transcription factor binding sites may be found in databases such as Transfac®. For example, also disclosed herein is a nucleic acid regulatory element (CSk-SH1) for enhancing cardiac and skeletal muscle-specific gene expression comprising binding sites for E2A, HNH1, NF1, C/EBP, LRF, MyoD, SREBP, STAT-1, EGR1, EGR2, EGR3, EGR4, TBP or MEF-2A and combinations thereof, such as E2A, HNH1, NF1, C/EBP, LRF, MyoD, SREBP; STAT-1, EGR1, EGR2, EGR3, EGR4, TBP and MEF-2A. For example, also disclosed herein is a nucleic acid regulatory element (Dph-CRE02) for enhancing diaphragm and skeletal muscle-specific gene expression comprising binding sites for NFYA, SIN3A, TCF12, PHF8, IRF1, EZH2, SUZ12, TBP, FOLR2A, REST, TEAD4, RBBP5, MSX-1 or SRF, and combinations thereof, such as NFYA, SIN3A, TCF12, PHF8, IRF1, EZH2, SUZ12, TBP, FOLR2A, REST, TEAD4, RBBP5, MSX-1 and SRF.

In some embodiments, these nucleic acid regulatory elements comprise at least two, such as 2, 3, 4, or more copies of any one or more of the recited TFBSs. As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 80%, preferably at least 90%, more preferably at least 95%, such as 95%, 96%, 97%, 98% or 99%, sequence identity.

The term "functional fragment" as used in the application with respect to the nucleic acid regulatory elements disclosed herein refers to fragments of said regulatory element sequences that retain the capability of regulating muscle-specific expression, i.e. they can still confer tissue specificity and they are capable of regulating expression of a (trans) gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, at least 400 or at least 450 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived. Functional fragments as defined herein preferably have at least 50%, at least 60%, at least 70%, at least 80%, at least 90%, at least 95% or about 100% of the nucleic acids regulatory capacities of the regulatory element wherefrom they are derived.

"Smooth muscle-specific expression" as used in the application, refers to the preferential or predominant expression of a (trans)gene (as RNA and/or polypeptide) in the smooth muscle cells, as compared to other (i.e. non-smooth muscle) cells or tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within the smooth muscle cells. According to a particular embodiment, smooth muscle specific expression entails that there is less than 50%, less than 40%, less than 30%, less than 20%, less than 10%, less than 5%, less than 2% or even less than 1% "leakage" of expressed gene product to other organs or tissue than muscle, such as for example lung, liver, brain, kidney and/or spleen.

"Diaphragm-specific expression" as used in the application, refers to the preferential or predominant expression of a (trans)gene (as RNA and/or polypeptide) in diaphragm, as compared to other (i.e. non-diaphragm) cells or tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm. According to a particular embodiment, diaphragm specific expression entails that there is less than 50%, less than 40%, less than 30%, less than 20%, less than 10%, less than 5%, less than 2% or even less than 1% "leakage" of expressed gene product to other organs or tissue than muscle, such as for example lung, liver, brain, kidney and/or spleen.

"Diaphragm and skeletal muscle-specific expression" as used in the application, refers to the preferential or predominant expression of a (trans)gene (as RNA and/or polypeptide) in diaphragm and skeletal muscle cells or diaphragm or skeletal muscle tissue, as compared to other (i.e. non-diaphragm or skeletal muscle) cells or tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm and/or skeletal muscle cells or tissue. According to a particular embodiment, diaphragm and skeletal muscle specific expression entails that there is less than 50%, less than 40%, less than 30%, less than 20%, less than 10%, less than 5%, less than 2% or even less than 1% "leakage" of expressed gene product to other organs or tissue than muscle, such as for example lung, liver, brain, kidney and/or spleen.

As used herein "diaphragm, skeletal muscle and cardiac-specific expression" or "diaphragm, skeletal muscle and heart-specific expression" refers to the preferential or predominant expression of a (trans)gene in diaphragm, heart, skeletal muscle cells or tissue and in particular heart muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm, skeletal muscle cells and heart tissue. Thus, according to particular embodiments, less than 50%, less than 40%, less than 30%, less than 20%, less than 10%, less than 5%, less than 2% or even less than 1% of the (trans)gene expression occurs in an organ or tissue other than diaphragm, heart and skeletal muscle, such as for example lung, liver, brain, kidney and/or spleen.

As used herein "diaphragm, skeletal muscle, smooth muscle and cardiac-specific expression" or "diaphragm, skeletal muscle, smooth muscle and heart-specific expression" refers to the preferential or predominant expression of a (trans)gene in diaphragm, heart, smooth muscle cells, skeletal muscle cells or tissue and in particular heart muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm, skeletal muscle cells, smooth muscle cells and heart tissue. Thus, according to particular embodiments, less than 50%, less than 40%, less than 30%, less than 20%, less than 10%, less than 5%, less than 2% or even less than 1% of the (trans)gene expression occurs in an organ or tissue other than diaphragm, heart, smooth muscle and skeletal muscle, such as for example lung, liver, brain, kidney and/or spleen.

As used herein "muscle-specific expression" refers to the preferential or predominant expression of a (trans)gene in muscle cells or tissue. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within muscle cells. Thus, according to particular embodiments, less than 50%, less than 40%, less than 30% or even less than 20% of the (trans)gene expression occurs in an organ or tissue other than muscle tissue. The same applies mutatis mutandis for myocyte-specific and muscle stem/progenitor cell-specific, satellite cell-specific or myoblast-specific expression, which may be considered as a particular form of muscle-specific expression. Throughout the application, where muscle-specific is mentioned in the context of expression, myocyte-specific and muscle stem/progenitor cell-specific, satellite cell-specific or myoblast-specific expression are also explicitly envisaged. Similarly, where cardiac and skeletal muscle-specific expression is used in the application, cardiomyocyte and skeletal myocyte-specific expression and cardiac myoblast, cardiac stem/progenitor cell-specific and skeletal myoblast-specific expression is also explicitly envisaged. Similarly, where skeletal muscle-specific expression is used in the application, skeletal myocyte-specific and skeletal myoblast-specific expression is also explicitly envisaged.

As used herein, the term "muscle" refers to all types of muscles known in the art including muscles of the diaphragm, skeletal muscle, heart muscle, cardiac muscle and/or smooth muscle.

As used herein, the terms "heart muscle" or "cardiac muscle" refer to the autonomically regulated, striated muscle type found in the heart.

As used herein, the term "skeletal muscle" refers to the voluntarily controlled, striated muscle type that is attached to the skeleton. Non-limiting examples of skeletal muscle include the biceps, the triceps, the quadriceps, the tibialis interior, and the gastrocnemius muscle.

The term "myocyte" as used herein, refers to a cell that has been differentiated from a progenitor muscle stem/progenitor cell, satellite cell or myoblast such that it is capable of expressing muscle-specific phenotype under appropriate conditions. Terminally differentiated myocytes fuse with one another to form myotubes, a major constituent of muscle fibers. The term "myocyte" also refers to myocytes that are de-differentiated. The term includes cells in vivo and cells cultured ex vivo regardless of whether such cells are primary or passaged.

The term “muscle stem/progenitor cell”, “satellite cell” or “myoblast” as used herein, refers to an embryonic cell in the mesoderm that differentiates to give rise to a muscle cell or myocyte. The term includes cells in vivo and cells cultured ex vivo regardless of whether such cells are primary or passaged.

In case the regulatory element is provided as a single stranded nucleic acid, e.g. when using a single-stranded AAV vector, the complement strand is considered equivalent to the disclosed sequences. Hence, also disclosed herein is a Dph-CSk nucleic acid regulatory element for enhancing muscle-specific gene expression comprising, consisting essentially of, or consisting of the complement of (i) a diaphragm-specific nucleic acid regulatory element comprising a sequence as defined by SEQ ID NO: 1; a sequence having at least 80%, preferably at least 85%, more preferably at least 90%, even more preferably at least 95%, such as 95%, 96%, 97%, 98%, or 99%, identity to the sequence defined by SEQ ID NO: 1; or a functional fragment of a sequence as defined by SEQ ID NO: 1; and (ii) a cardiac and skeletal muscle-specific nucleic acid regulatory element comprising a sequence as defined by SEQ ID NO: 2; a sequence having at least 80%, preferably at least 85%, more preferably at least 90%, even more preferably at least 95%, such as 95%, 96%, 97%, 98%, or 99%, identity to the sequence defined by SEQ ID NO: 2; or a functional fragment of a sequence as defined by SEQ ID NO: 2.

Preferably the Dph-CSk regulatory element as described herein is fully functional while being only of limited length. This allows its use in vectors or nucleic acid expression cassettes without unduly restricting their payload capacity.

In particular embodiments, the Dph-CSk nucleic acid regulatory element comprising, consisting essentially of, or consisting of (i) a sequence as defined by SEQ ID NO: 1, also referred to herein as “Dph-CRE02”; and (ii) a sequence as defined by SEQ ID NO: 2, also referred to herein as “CSk-SH1”.

The Dph-CSk nucleic acid regulatory element as described herein may be produced by any methods known in the art, such as any synthetic DNA synthesis or cloning (e.g. recombinant DNA technology) method known in the art.

Furthermore, the diaphragm-specific nucleic acid regulatory element as described herein and the cardiac and skeletal muscle-specific nucleic acid regulatory element as described herein can be combined in any order in the Dph-CSk nucleic acid regulatory element as described herein. The cardiac and skeletal muscle-specific nucleic acid regulatory element may be located 3' or 5' of the diaphragm-specific nucleic acid regulatory element.

In particular embodiments, the cardiac and skeletal muscle-specific nucleic acid regulatory element comprising a sequence as defined by SEQ ID NO: 2; a sequence having at least 80%, preferably at least 85%, more preferably at least 90%, even more preferably at least 95%, such as 95%, 96%, 97%, 98%, or 99%, identity to the sequence defined by SEQ ID NO: 2; or a functional fragment of a sequence as defined by SEQ ID NO: 2 is located 3' of the diaphragm-specific nucleic acid regulatory element comprising a sequence as defined by SEQ ID NO: 1; a sequence having at least 80%, preferably at least 85%, more preferably at least 90%, even more preferably at least 95%, such as 95%, 96%, 97%, 98%, or 99%, identity to the sequence defined by SEQ ID NO: 1; or a functional fragment of a sequence as defined by SEQ ID NO: 1.

The cardiac and skeletal muscle-specific nucleic acid regulatory element may be directly located 3' or 5' of the diaphragm-specific nucleic acid regulatory element (i.e. in tandem). Alternatively, a nucleotide linker comprising one or more nucleotides may be located in between the cardiac and skeletal muscle-specific nucleic acid regulatory element and the diaphragm-specific nucleic acid regulatory element.

Accordingly, in particular embodiments, the Dph-CSk nucleic acid regulatory element for enhancing muscle-specific gene expression as described herein comprises a nucleotide linker consisting of at least one, such as 1, 2, 3, 4, 5, 6, 7, 8, 9, 10, 11, 12, 13, 14, 15, at least 10, at least 20, at least 30, at least 40, or at least 50, preferably at least 10, nucleotides located between the diaphragm-specific nucleic acid regulatory element as described herein and the cardiac and skeletal muscle-specific nucleic acid regulatory element as described herein. Preferably, the nucleotide linker consists of a sequence of from 5 to 30, from 5 to 25, from 5 to 20, or from 10 to 20, nucleotides, preferably from 10 to 20 nucleotides. More preferably, the nucleotide linker comprises, consists essentially of or consists of a sequence as defined in SEQ ID NO: 13 (i.e. 5'-GGCGCGCCACGCGT-3').

As used herein, the term “linker” refers to a connecting element that serves to link other elements. In particular embodiments, the linker is a covalent linker, achieving a covalent bond. The terms “covalent” or “covalent bond” refer to a chemical bond that involves the sharing of one or more electron pairs between two atoms. For many molecules, the sharing of electrons allows each atom to attain the equivalent of a full outer electron shell, corresponding to a stable electronic configuration. Covalent bonds include different types of interactions, including σ-bonds, π-bonds, metal-to-metal bonds, agostic interactions, bent bonds and three-center two-electron bonds.

In particular embodiments, the Dph-CSk nucleic acid regulatory element as described herein comprises, consists essentially of or consists of a sequence as defined by SEQ ID NO: 3.

In particular embodiments, no nucleotide linker is introduced between the diaphragm-specific nucleic acid regulatory element as described herein and the cardiac and skeletal muscle-specific nucleic acid regulatory element as described herein. Hence, in preferred embodiments, the diaphragm-specific nucleic acid regulatory element as described herein and the cardiac and skeletal muscle-specific nucleic acid regulatory element as described herein are directly aligning (i.e. in tandem).

The Dph-CSk nucleic acid regulatory element as described herein may be used in a nucleic acid expression cassette. Accordingly, disclosed herein is the use of the Dph-CSk as described herein in a nucleic acid expression cassette.

Further disclosed herein is a nucleic acid expression cassette comprising a Dph-CSk nucleic acid regulatory element as described herein, operably linked to a promoter. In particular embodiments, the nucleic acid expression cassette does not contain a transgene. Such nucleic acid expression cassette may be used to drive expression of an endogenous gene. In preferred embodiments, the nucleic acid expression cassette comprises a Dph-CSk nucleic acid regulatory element as described herein, operably linked to a promoter and a transgene.

As used herein, the term “nucleic acid expression cassette” refers to nucleic acid molecules that include one or more transcriptional control elements (such as, but not limited to promoters, enhancers and/or regulatory elements, polyadenylation sequences, and introns) that direct (trans) gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term "operably linked" as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one Dph-CSk nucleic acid regulatory element as described herein. In alternative embodiments, the nucleic acid expression cassette comprises two or more, such as, e.g., 2, 3, 4, 5, 6, 7, 8, 9, or 10, Dph-CSk nucleic acid regulatory elements as described herein, i.e. they are combined modularly to enhance their regulatory (and/or enhancing) effect.

As used in the application, the term "promoter" refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e g enhancers or silencers, or regulatory elements). The promoter may either be tissue-specific or ubiquitously expressed. It may be a promoter of a cellular gene or a viral gene. Promoter can be polymerase II promoters. Alternatively, polymerase III (pol III) promoters (e.g. U6) or chimeric pol III promoters can be considered (e.g. to express non-coding RNAs). Synthetic muscle promoters can also be considered.

In the context of the present application, a promoter is typically operably linked to a Dph-CSk regulatory element as taught herein to regulate transcription of a (trans)gene. When a Dph-CSk regulatory element as described herein is operably linked to both a promoter and a transgene, the regulatory element can (1) confer a significant degree of muscle-specific, preferably diaphragm, cardiac muscle, smooth muscle and skeletal muscle-specific, more preferably diaphragm, cardiac and skeletal muscle-specific, expression in vivo (and/or in vitro in cell lines derived from muscle cells or tissue, preferably cardiac, diaphragm, smooth muscle and skeletal muscle cells or tissue, more preferably cardiac, diaphragm, and skeletal muscle cells or tissue) of the transgene, and/or (2) can increase the level of expression of the transgene in muscle, preferably in diaphragm, cardiac muscle, smooth muscle and skeletal muscle, more preferably in diaphragm, cardiac and skeletal muscle (and/or in vitro in cell lines derived from muscle cells or tissue, preferably cardiac, diaphragm, smooth muscle and skeletal muscle cells or tissue, more preferably cardiac, diaphragm, and skeletal muscle cells or tissue).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus (e.g. cytomegalovirus (CMV)), any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

The enrichment in muscle-specific TFBS in the nucleic acid regulatory elements disclosed herein in principle allows the regulatory elements to direct muscle-specific expression even from a promoter that itself is not muscle-specific (e.g. CAG promoter, CMV promoter). Hence, the regulatory elements disclosed herein can be used in nucleic acid expression cassettes in conjunction with any promoter, in particular the promoter may either be tissue-specific, e.g. muscle-specific, or ubiquitously expressed. Non-limiting examples of ubiquitously expressed promoters include polymerase II (pol II) promoters, polymerase III (pol III) promoters (e.g. U6) and chimeric pol III promoters. Preferably, the nucleic acid expression cassettes disclosed herein comprise a muscle-specific promoter, in particular a diaphragm, smooth muscle, heart, and/or skeletal muscle-specific promoter, more particularly a diaphragm, heart, and/or skeletal muscle-specific promoter, in order to increase muscle-specificity, in particular diaphragm, smooth muscle, heart, and/or skeletal muscle-specificity, more particularly diaphragm, heart, and/or skeletal muscle-specificity, and/or reduce leakage of expression in other tissues. Non-limiting examples of muscle-specific promoters include the desmin (DES) promoter, the synthetic SPc-5-12 promoter (SPc5-12), the alpha-actin1 promoter (ACTA1), the Creatine kinase, muscle (CKM) promoter, the Four and a half LIM domains protein 1 (FHL1) promoter, the alpha 2 actinin (ACTN2) promoter, the filamin-C (FLNC) promoter, the sarcoplasmic/endoplasmic reticulum calcium ATPase 1 (ATP2A1) promoter, the troponin I type 1 (TNNI1) promoter, the troponin I type 2 (TNNI2) promoter, the Troponin T Type 3 (TNNT3) promoter, the myosin-1 (MYH1) promoter, the phosphorylatable, fast skeletal muscle myosin light chain (MYLPF) promoter, the tropomyosin 2 (TPM2) promoter, the alpha-3 chain tropomyosin (TPM3) promoter, the ankyrin repeat domain-containing protein 2 (ANKRD2) promoter the myosin heavy-chain (MHC) promoter, the myosin light-chain (MLC) promoter, the muscle creatine kinase (MCK) promoter, the myosin light chain 2 (MYL2) promoter, the Myoglobin (MB) promoter, the Titin-Cap (TCAP) promoter, the Myosin, Heavy Chain 7 (MYH7) promoter, the Aldolase A (ALDOA) promoter, the Tropomyosin 1 (TPM1) promoter, the Troponin T type 2, cardiac type (TNNT2) promoter, the Troponin C Type 2 (fast) (TNNC2) promoter, the Troponin C Type 1 (TNNC1) promoter, the myosin light chain 1 (MYL1) promoter, the Troponin T Type 1 (TNNT1) promoter, the myosin-2 (MYH2) promoter, the sarcolipin (SLN) promoter, the myosin binding protein C1 (MYBPC1) promoter, the enolase (EN03) promoter, the alpha myosin heavy chain promoter (αMHC), the carbonic anhydrase 3 (CA3) promoter, the myosin heavy chain 11 (Myh11) promoter, the transgelin (Tagln) (also known as SM22α promoter), the actin alpha 2, smooth muscle (Acta2) promoter, and the synthetic muscle promoters as described in Li et al. (1999, Nat Biotechnol. 17:241-245), such as the SPc5-12 promoter, the dMCK promoter and the tMCK promoter consisting of respectively, a double or triple tandem of the MCK enhancer to the MCK basal promoter as described in Wang et al. (2008, Gene Ther, 15:1489-1499), or a synthetic skeletal and cardiac muscle-specific promoter MHCK7 as described in Salva et al. (2007. Mol Ther 15: 320-9).

In particularly preferred embodiments, the promoter is a mammalian promoter, in particular a murine or human promoter.

In particularly preferred embodiments, the promoter is a muscle-specific promoter selected from the group consisting of: the SPc5-12 promoter, the DES promoter and the MHCK7 promoter.

In particularly preferred embodiments, the promoter is the promoter is the SPc5-12 promoter, the desmin promoter or the MHCK7 promoter, preferably the SPc5-12 promoter as defined by SEQ ID NO: 4, the desmin promoter as defined by SEQ ID NO: 22 or the MHCK7 promoter as defined by SEQ ID NO: 23.

In even more preferred embodiments, the promoter is the SPc5-12 promoter, more preferably the SPc5-12 promoter as defined by SEQ ID NO: 4.

To minimize the length of the nucleic acid expression cassette, the regulatory elements may be linked to minimal promoters, or shortened versions of the promoters described herein. A "minimal promoter" (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion.

The term "transgene" as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), non-coding RNA (ncRNA), long non-coding RNA (lncRNA), guide RNA (gRNA), catalytic RNA, antisense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular a mammal or human, in which it is introduced, e.g. in cases where the nucleic acid expression cassette is used for gene therapy).

The transgene may be a full-length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By "mutant form" is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein may encode members of the CRISPR/Cas system, such as Cas and/or one or more gRNAs.

The transgene that may be contained in the nucleic acid expression cassettes described herein typically encodes a gene product such as RNA or a polypeptide (protein).

In embodiments, the transgene encodes a therapeutic or immunogenic protein, preferably a therapeutic protein.

The therapeutic protein may be a secretable protein, such as a secretable protein that is absent or defective as a result of a single gene disorder, or a non-secreted protein.

In particular embodiments, the therapeutic protein is a secretable protein, preferably a secretable therapeutic protein, such as acid α-glucosidase (GAA), α-galactosidase A, follistatin, clotting factors, such as factor VIII or factor IX, insulin, erythropoietin, lipoprotein lipase, antibodies or nanobodies, growth factors, angiogenic factors, cytokines, chemokines, plasma factors etc.

In particular embodiments, the therapeutic protein is a non-secreted protein, such as metabolic enzymes (e.g. tafazzin), lysosomal proteins, nuclear proteins, etc.

In particular embodiments, the therapeutic protein is a structural protein. Non-limiting examples of structural proteins, in particular structural therapeutic proteins, include myotubularin, dysferlin, microdystrophin 1, dystrophin and sarcoglycans.

A non-exhaustive and non-limiting list of transgenes envisaged in the application includes transgenes encoding: angiogenic factors for therapeutic angiogenesis (e.g. VEGF, PlGF, or guidance molecules such as ephrins, semaphorins, Slits and netrins or their cognate receptors); clotting factors (e.g. factor VIII or factor IX); insulin; lipoprotein lipase; plasma factors; cytokines, chemokines and/or growth factors (e.g. erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF)); proteins involved in calcium handling (e.g. SERCA: Sarco/Endoplasmic Reticulum Ca2+-ATPase, phospholamban, calsequestrin, sodium-calcium exchanger, L-type calcium's channel, and ryanodine receptors); calcineurin; microdystrophin (MD); follistatin (FST); myotubularin 1 (MTM1); dysferlin; dystrophin; metabolic enzymes; nuclear proteins; mitochondrial proteins (e.g. tafazzin); lysosomal proteins (e.g. acid α-glucosidase (GAA) (as a secreted or native form), α-galactosidase A or Lysosome-associated membrane protein 2 (LAMP2)); ion channels (e.g. SCNSA); enzymes involved in glycogen metabolism (e.g. Glycogen synthase (GYS2), Glycogen debranching enzyme (AGL), Glycogen branching enzyme (GBE1), Muscle glycogen phosphorylase (PYGM), Muscle phosphofructokinase (PKFM), Phosphoglycerate mutase (PGAM2), Aldolase A (ALDOA), β-enolase (ENO3) or Glycogenin-1 (GYG1)); enzymes deficient in mucopolysaccharidosis (e.g. α-L-iduronidase, Iduronate sulfatase, Heparan sulfamidase, N-acetylglucosaminidase, Heparan-α-glucosaminide N-acetyltransferase, N-acetylglucosamine 6-sulfatase, Galactose-6-sulfate sulfatase, β-galactosidase, N-acetylgalactosamine-4-sulfatase, β-glucuronidase or Hyaluronidase); sarcoglycan (e.g. alpha-sarcoglycan, beta-sarcoglycan and gamma-sarcoglycan); anoctamin 5; calpain 3; antibodies; nanobodies; anti-viral dominant-negative proteins; and fragments, subunits or mutants thereof.

In further particular embodiments, the transgene is selected from the group consisting of a transgene encoding acid α-glucosidase or GAA (e.g. as a secreted or native form), a transgene encoding α-galactosidase A, a transgene encoding LAMP2, a transgene encoding microdystrophin, a transgene encoding follistatin (FST), a transgene encoding myotubularin 1 (MTM1), a transgene encoding sarcoglycan (SG) and a transgene encoding tafazzin.

In further particular embodiments, the transgene encodes a lysosomal protein, preferably a lysosomal protein selected from the group consisting of acid α-glucosidase (e.g. as a secreted or native form), α-galactosidase A and LAMP2.

In more particular embodiments, the transgene encodes GAA such as defined in SEQ ID NO: 5, or a codon-optimized variant thereof such as defined in SEQ ID NO: 6.

In further particular embodiments, the transgene encodes a non-lysosomal protein, preferably selected from the group consisting of microdystrophin, follistatin (FST), myotubularin 1 (MTM1), sarcoglycan (SG) and tafazzin.

The transgene may also be a reporter gene, i.e. the transgene encodes a reporter such as a luciferase enzyme.

The transgene may also encode an immunogenic protein. Non-limiting examples of immunogenic proteins include epitopes and antigens derived from a pathogen.

As used herein, the term "immunogenic" refers to a substance or composition capable of eliciting an immune response. In particular embodiments, the nucleic acid expression cassettes as taught herein may comprise more than one, such as two, three, four, or five, transgenes.

Other sequences may be incorporated in the nucleic acid expression cassette as taught herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette as taught herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron.

Preferably, the intron is MVM intron, more preferably an MVM intron as defined in SEQ ID NO: 7.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit □-globin (mRBG) gene, and the synthetic polyA s(SPA) site as described in Levitt et al. (1989, Genes Dev 3:1019-1025).

In particular embodiments, the polyadenylation signal is a synthetic polyadenylation signal or a Simian Virus 40 (SV40) polyadenylation signal, more preferably the polyadenylation signal is a synthetic polyadenylation signal as defined by SEQ ID NO: 8.

In particular embodiments, the nucleic acid expression cassette comprises (i) a diaphragm-specific nucleic acid regulatory element comprising a sequence having at least 80%, preferably at least 95%, identity to the sequence defined by SEQ ID NO: 1, or a functional fragment thereof;

(ii) a cardiac and skeletal muscle-specific nucleic acid regulatory element comprising a sequence having at least 80%, preferably at least 95%, identity to the sequence defined by SEQ ID NO: 2, or a functional fragment thereof; optionally wherein a nucleotide linker is present between said diaphragm-specific nucleic acid regulatory element and said cardiac and skeletal muscle-specific nucleic acid regulatory element;

(iii) a muscle-specific promoter, preferably an SPc5-12 promoter, more preferably the SPc5-12 promoter as defined by SEQ ID NO: 4;

(iv) a transgene, preferably a transgene encoding GAA such as defined in SEQ ID NO: 5, or a codon-optimized variant thereof such as defined in SEQ ID NO: 6;

(v) optionally an MVM intron, preferably the MVM intron as defined by SEQ ID NO: 7; and (vi) optionally a synthetic polyadenylation signal, preferably a synthetic polyadenylation signal as defined by SEQ ID NO: 8.

In particular embodiments, the nucleic acid expression cassette comprises (i) a Dph-CSk nucleic acid regulatory element comprising a sequence as defined by SEQ ID NO: 3, (ii) an SPc5-12 promoter, preferably the SPc5-12 promoter as defined by SEQ ID NO: 4;

(iii) a transgene, preferably a transgene encoding GAA such as defined in SEQ ID NO: 5, or a codon-optimized variant thereof such as defined in SEQ ID NO: 6;

(iv) optionally an MVM intron, preferably the MVM intron as defined by SEQ ID NO: 7; and (v) optionally a synthetic polyadenylation signal, preferably a synthetic polyadenylation signal as defined by SEQ ID NO: 8.

The Dph-CSk nucleic acid regulatory element and the nucleic acid expression cassette as taught herein may be used as such, or typically, they may be part of a nucleic acid vector. Accordingly, further disclosed herein is the use of a Dph-CSk nucleic acid regulatory element as described herein or a nucleic acid expression cassette as described herein in a vector, in particular a nucleic acid vector.

Also disclosed herein is a vector comprising a Dph-CSk nucleic acid regulatory element as taught herein. In further embodiments, the vector comprises a nucleic acid expression cassette as taught herein.

The term "vector" as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term "vector" may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably an AAV vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), and also the use of single-stranded AAV vectors (ssAAV) are also encompassed herein.

The vector may be an AAV vector of which the AAV capsid belongs to one of the naturally occurring AAV serotypes (e.g. AAV1, AAV2, AAV3, AAV4, AAV5, AAV6, AAV7, AAV8, AAV9, AAV10, AAV rh74) or of which the AAV capsid is engineered to direct the vector specifically to muscle cells. For example, the vector may be a AAVpol vector as described in Tulalamba W et al. (Tulalamba W, et al. Distinct transduction of muscle tissue in mice after systemic delivery of AAVpol vectors. Gene Ther. (2019) https://doi.org/10.1038/s41434-019-0106-3. AAV serotype 9 (AAV9) and AAV serotype 8 (AAV8) are well suited to achieve efficient transduction in cardiac and skeletal muscle. Accordingly, in particularly preferred embodiments, the vector is an AAV9 or AAV8 vector, preferably a self-complementary AAV9 vector (scAAV9) or a single-stranded AAV8 vector (ssAAV8).

Production of AAV vector particles can e.g. be achieved by transient transfection of suspension-adapted mammalian HEK293 cells, as described (Chahal et al. Production of adeno-associated virus (AAV) serotypes by transient transfection of HEK293 cell suspension cultures for gene delivery, Journal of Virological Methods. 196: 163-173 (2014); Grieger et al., Production of recombinant adeno-associated virus vectors using suspension HEK293 cells and continuous harvest of vector from the culture media for GMP FIX and FLT1 clinical vector. Molecular Therapy. 24: 287-297 (2016); Blessing et al., Scalable Production of AAV Vectors in Orbitally Shaken HEK293 Cells. Molecular Therapy Methods & Clinical Development. 13: 14-26 (2019)), or by the infection of *Spodoptera frugiperda* (Sf9) insect cells using the baculovirus expression vector system (BEVS), as described (Kotin et al. Manufacturing Clinical Grade Recombinant Adeno-Associated Virus Using Invertebrate Cell Lines. Human Gene Therapy. 28: 350-360 (2017)), followed by a purification step. Purification may be based on cesium chloride (CsCl) density gradient ultracentrifugation, as described (Vanden Driessche et al., 2007), or using chromatographic techniques or columns or by immunoaffinity as known in the art.

In other embodiments, the vector is a non-viral vector, preferably a plasmid, a minicircle, an episomal vector, or a transposon-based vector, such as a Sleeping Beauty (SB)-based vector or piggyBac(PB)-based vector.

In yet other embodiments, the vector comprises viral and non-viral elements.

The person skilled in the art will understand that the maximal lengths of CREs or the Dph-CSk CRE, the promoter, the transgene, the intron and/or the polyadenylation signal depends on the cloning capacity of the type of vector being used.

In particular embodiments, the invention provides a vector comprising a nucleic acid expression cassette comprising:

(i) a diaphragm-specific nucleic acid regulatory element comprising a sequence having at least 80%, preferably at least 95%, identity to the sequence defined by SEQ ID NO: 1, or a functional fragment thereof;

(ii) a cardiac and skeletal muscle-specific nucleic acid regulatory element comprising a sequence having at least 80%, preferably at least 95%, to the sequence defined by SEQ ID NO: 2, or a functional fragment thereof;

(iii) a muscle-specific promoter, preferably an SPc5-12 promoter, more preferably the SPc5-12 promoter as defined by SEQ ID NO: 4;

(iv) a transgene, preferably a transgene encoding GAA such as defined in SEQ ID NO: 5, or a codon-optimized variant thereof such as defined in SEQ ID NO: 6;

(v) optionally an MVM intron, preferably the MVM intron as defined by SEQ ID NO: 7; and (vi) optionally a synthetic polyadenylation signal, a synthetic polyadenylation signal as defined by SEQ ID NO: 8.

In particular embodiments, the invention provides a vector comprising a nucleic acid expression cassette comprising:

(i) a Dph-CSk nucleic acid regulatory element comprising a sequence defined by SEQ ID NO: 3;

(ii) an SPc5-12 promoter, preferably the SPc5-12 promoter as defined by SEQ ID NO: 4; and (iii) a transgene, preferably a transgene encoding GAA such as defined in SEQ ID NO: 5, or a codon-optimized variant thereof such as defined in SEQ ID NO: 6;

(iv) optionally an MVM intron, preferably the MVM intron as defined by SEQ ID NO: 7; and (v) optionally a synthetic polyadenylation signal, a synthetic polyadenylation signal as defined by SEQ ID NO: 8.

In more particular embodiments, the vector comprises, consists essentially of or consists of a sequence as defined by SEQ ID NO: 9 or SEQ ID NO: 11, preferably SEQ ID NO: 9.

The nucleic acid expression cassettes and vectors as taught herein may be used, for example, to express proteins that are normally expressed and utilized in muscle (i.e. structural proteins), or to express proteins that are expressed in muscle and that are then exported to the blood stream for transport to other portions of the body (i.e. secretable proteins). For example, the expression cassettes and vectors as taught herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors as taught herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, also disclosed herein is a pharmaceutical composition comprising a nucleic acid expression cassette or a vector described herein.

The use of nucleic acid regulatory elements described herein for the manufacture of these pharmaceutical compositions is also disclosed herein.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

Furthermore, also disclosed herein is the Dph-CSk nucleic acid regulatory element, the nucleic acid expression cassette, the vector, or the pharmaceutical composition as taught herein for use in medicine.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. “Preventing” also encompasses preventing the recurrence or relapse-prevention of a disease or disorder for instance after a period of improvement.

In embodiments, the Dph-CSk nucleic acid regulatory element, preferably the Dph-CSk nucleic acid regulatory element with a sequence as defined in SEQ ID NO: 3, the nucleic acid expression cassettes, the vectors, or the pharmaceutical compositions as taught herein may be for use in gene therapy, in particular muscle-directed gene therapy, preferably diaphragm-, skeletal muscle-, smooth muscle- and heart-directed gene therapy, more preferably diaphragm-, skeletal muscle- and heart-directed gene therapy.

Also disclosed herein is the use of the Dph-CSk nucleic acid regulatory element, preferably the Dph-CSk nucleic acid regulatory element with a sequence as defined in SEQ ID NO: 3, the nucleic acid expression cassettes, the vectors, or the pharmaceutical compositions as taught herein for the manufacture of a medicament for gene therapy, in particular muscle-directed gene therapy, preferably diaphragm-, skeletal muscle-, smooth muscle- and heart-directed gene therapy, more preferably diaphragm-, skeletal muscle- and heart-directed gene therapy.

Also disclosed herein is a method for treating a subject by gene therapy, in particular muscle-directed gene therapy, preferably diaphragm-, skeletal muscle-, smooth muscle- and heart-directed gene therapy, more preferably diaphragm-, skeletal muscle- and heart-directed gene therapy, wherein said subject is in need of said gene therapy comprising:

introducing in the subject, in particular in muscle tissue or cells of the subject, preferably diaphragm, skeletal muscle, smooth muscle and heart tissue or cells of the subject, more preferably diaphragm, skeletal muscle and heart tissue or cells of the subject, the Dph-CSk nucleic acid regulatory element, preferably the Dph-CSk nucleic acid regulatory element with a sequence as defined in SEQ ID NO: 3, the nucleic acid expression cassettes, the vectors, or the pharmaceutical compositions as taught herein; and expressing a therapeutically effective amount of the transgene product in the subject, in particular in muscle tissue or cells of the subject, preferably diaphragm, skeletal muscle, smooth muscle, and heart tissue or cells of the subject, more preferably diaphragm-, skeletal muscle- and heart tissue or cells of the subject.

The transgene product may be any one of the following transgenes as described herein, preferably the transgene is a transgene encoding a lysosomal protein, more preferably the transgene is a transgene encoding a lysosomal protein selected from the group consisting of acid α-glucosidase (GAA) (e.g. GAA as a secreted or native form), α-galactosidase A and LAMP2.

In particular embodiments, the transgene is a transgene encoding GAA, preferably human GAA (hGAA) or its codon-optimised variant (hGAAco). In more particular embodiments, the transgene is a transgene encoding hGAA with a sequence as defined by SEQ ID NO: 5 or hGAAco with a sequence as defined by SEQ ID NO: 6.

Alternatively, the transgene product may be a transgene encoding RNA, such as siRNA or non-coding RNA (ncRNA).

Exemplary diseases and disorders that may benefit from gene therapy using the nucleic acid regulatory elements, the nucleic acid expression cassettes, the vectors, or the pharmaceutical compositions described herein include:

lysosomal storage diseases (e.g. Fabry disease) including glycogen storage disorders (e.g. Pompe disease glycogen storage disorder (GSD) type II, Danon disease, glycogen storage disorder (GSD) type Hb, GSD III or GSD 3 (also known as Con’s disease or Forbes’ disease), GSD IV or GSD4 (also known as Andersen disease), GSD V or GSD5 (also known as McArdle disease), GSD VII or GSD7 (also known as Tarui’s disease), GSD X or GSD10, GSD XII or GSD 12 (also known as Aldolase A deficiency), GSD XIII or GSD13, GSD XV or GSD15) and mucopolysaccharidosis disorders (e.g. Hunter syndrome, Sanfilippo syndrome, mucopolyssacharidose (MPS) I, MPS II, MPS III, MPS IIIA, MPS IIIB, MPS HIC, MPS IV, MPS VI, MPS VII, MPS IX);
mitochondrial disorders (e.g. Barth syndrome);
channelopathy (e.g. Brugada syndrome);
metabolic disorders;
myotubular myopathy (MTM);
muscular dystrophy (e.g. Duchenne muscular dystrophy (DMD), Becker muscular dystrophy (BMD));
myotonic dystrophy;
Myotonic Muscular Dystrophy (DM);
Miyoshi myopathy;
Fukuyama type congenital;
dysferlinopathies;
neuromuscular disease;
motor neuron diseases (MND) (e.g. Charcot-Marie-Tooth disease (CMT), spinal muscular atrophy (SMA) or amyotrophic lateral sclerosis (ALS));
Emery-Dreifuss muscular dystrophy;
facioscapulohumeral muscular dystrophy (FSHD);
congenital muscular dystrophies;
congenital myopathies;
limb girdle muscular dystrophy (e.g. Limb Girdle Muscular Dystrophy type 2E (LGMD2E), Limb Girdle Muscular Dystrophy type 2D (LGMD2D), Limb Girdle Muscular Dystrophy type 2C (LGMD2C), Limb Girdle Muscular Dystrophy type 2B (LGMD2B), Limb Girdle Muscular Dystrophy type 2L (LGMD2L), Limb Girdle Muscular Dystrophy type 2A (LGMD2A));
metabolic myopathies;
muscle inflammatory diseases;
myasthenia;
mitochondrial myopathies;
anomalies of ionic channels;
nuclear envelop diseases;
cardiomyopathies;
cardiac hypertrophy;
heart failure;
distal myopathies;
hemophilia (e.g. hemophilia A and B);
diabetes; and
cardiovascular diseases and/or heart diseases (e.g. atherosclerosis, arteriosclerosis, coronary heart disease, coronary artery disease, peripheral arterial disease, congenital heart disease, congestive heart failure, heart failure (also known as cardiac insufficiency), myocardial infarction (also known as heart attack), cardiac ischemia, acute coronary syndrome, unstable angina, stable angina, cardiomyopathy, hypertrophic cardiomyopathy, dilated cardiomyopathy, restrictive cardiomyopathy, primary cardiomyopathies caused by genetic mutations such as Brugada syndrome, Pompe disease, Danon disease and Fabry disease, cardiac amyloidosis (also known as stiff heart syndrome), myocarditis (also known as inflammatory cardiomyopathy), valvular heart disease, valvular stenosis, valvular insufficiency, endocarditis, rheumatic heart disease, pericarditis (i.e. a disease caused by an inflammation and/or infection of the pericardium), cardiac tamponade (also known as pericardial tamponade), cardiac arrhythmia, hypertension, hypotension, vessel stenosis, valve stenosis, or restenosis).

In addition, many neuromuscular disorders affect respiratory function due to weakening of the diaphragm and respiratory muscles (www.medscape.com/viewarticle/805299_3) Semin Respir Crit Care Med. 2002 June; 23(3): 191-200). Causes of diseases of the diaphragm vary, but they can be due to gene defects that influence diaphragm function directly. In particular, there are multiple genetic disorders that are due to mutations in genes that affect the function of the diaphragm, often in combination with abnormalities at the level of skeletal muscles and/or heart. For example, myotubular myopathy (MTM) is due to mutations in the myotubularin gene and affects the skeletal muscle and diaphragm. Patients suffering from MTM typically present with hypotonia, generalized muscle weakness and respiratory failure at birth. Survival beyond the postnatal period requires intensive support, often including gastrostomy feeding and mechanical ventilation. Because of their severe breathing problems, patients suffering from MTM typically do not live past age 2. For MTM, muscle-directed gene therapy is currently the only clinically relevant option. Alternatively, Pompe's disease (also referred to as glycogen storage disorder type II or GSD II) mainly affects skeletal muscle, diaphragm and heart. GSD II results in deficiency of the lysosomal enzyme acid α-glucosidase (GAA) that leads to a lysosomal storage defect. In GSD II patients, glycogen cannot be broken down effectively into glucose. The accumulation of glycogen in GSD II patients causes myopathy with progressive muscle weakness. Without medical intervention, patients suffering from the most severe form of GSD II die because of respiratory failure within the first year of life. Other muscle diseases such as Duchenne muscular dystrophy (DMD) afflicts approximately one in 3500 live male births. The disease leads to a progressive destruction of skeletal muscles, including the diaphragm, the most affected individuals die of ventilatory failure in the third decade of life. Many other myopathies also affect pulmonary function, including—but not limited to—polymyositis/dermatomyositis, hereditary channel disorders, mitochondrial encephalomyopathies, acid maltase deficiency, and congenital myopathy, disuse atrophy. Other diseases affecting diaphragm include Congenital Muscular Dystrophy (CMD), Becker Muscular Dystrophy (BMD), Facioscapulohumeral Muscular Dystrophy (FSHD), Limb Girdle Muscular Dystrophy (LGMD), Myotonic Muscular Dystrophy (DM), Miyoshi myopathy, Fukuyama type congenital muscular dystrophy, dysferlinopathies. Also many neuropathic disorders weaken the diaphragm and respiratory muscles. This includes amyotrophic lateral sclerosis, poliomyelitis, post-polio syndrome, Kennedy syndrome, stroke, multiple sclerosis, spinal muscular atrophy, syringomyelia, neuralgic neuropathy, and motor neuron diseases. Brachial plexitis and isolated unilateral or bilateral phrenic neuropathies can also weaken the diaphragm significantly. Peripheral neuropathies affecting respiration are primarily acute disorders such as Guillain-Barré syndrome, porphyria, and critical illness neuropathy, but chronic diseases such as chronic inflammatory demyelinating polyneuropathy (CIDP) and Charcot-Marie-Tooth disease (CMT) can also cause respiratory insufficiency. Disorders of neuromuscular transmission such as Lambert-Eaton syndrome, and myasthenia gravis often affect respiration. Alternatively, diaphragm dysfunction can be the result of congenital defects resulting in anatomical abnormalities (e.g. Arnold-Chiari malformation) or acquired defects, which occur as the result of an injury, trauma, infection (e.g. West Nile virus, botulism), exposure to, organophosphates, radiation therapy, malnutrition, tumour compression or surgery. Cold cardioplegia used in cardiac surgery is another common cause of phrenic nerve injury. In addition, radiation therapy can affect the phrenic nerve resulting in diaphragmatic dysfunction. Obstructive airway diseases that affect the lungs, such as chronic obstructive pulmonary disease (COPD) and asthma, can result in significant hyperinflation resulting in diaphragmatic disadvantage and weakness. Finally, it is known that lupus and thyroid disorders can also contribute to diaphragm dysfunction.

Further exemplary diseases and disorders that may benefit from gene therapy using the nucleic acid regulatory elements, the nucleic acid expression cassettes, the vectors, or the pharmaceutical compositions described herein are single gene disorders that affect the skeletal muscle, the heart, the diaphragm and/or the smooth muscle, as well as single gene disorders that can be corrected by a secretable protein expressed from the skeletal muscle, the heart, the diaphragm and/or the smooth muscle.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells.

Also disclosed herein is the Dph-CSk nucleic acid regulatory element, preferably the Dph-CSk nucleic acid regulatory element with a sequence as defined in SEQ ID NO: 3, the nucleic acid expression cassette, the vector, or the pharmaceutical, wherein the transgene encodes a lysosomal protein, preferably a lysosomal protein selected from the group consisting of acid α-glucosidase (GAA), α-galactosidase A and LAMP2 for use in the treatment of a lysosomal storage disease, preferably a lysosomal storage disease selected from the group consisting of Pompe disease, Danon disease and Fabry disease.

Also disclosed herein is the Dph-CSk nucleic acid regulatory element, preferably the Dph-CSk nucleic acid regulatory element with a sequence as defined in SEQ ID NO: 3, the nucleic acid expression cassette, the vector, or the pharmaceutical, wherein the transgene encodes acid α-glucosidase (GAA) as defined by SEQ ID NO: 5, more preferably the codon-optimised human acid α-glucosidase gene (hGAAco) as defined by SEQ ID NO: 6, for use in the treatment of Pompe disease.

Also disclosed herein is the Dph-CSk nucleic acid regulatory element, preferably the Dph-CSk nucleic acid regulatory element with a sequence as defined in SEQ ID NO: 3, the nucleic acid expression cassette, the vector, or the pharmaceutical, wherein the transgene encodes α-galactosidase A, for use in the treatment of Danon disease.

Also disclosed herein is the Dph-CSk nucleic acid regulatory element, preferably the Dph-CSk nucleic acid regulatory element with a sequence as defined in SEQ ID NO: 3, the nucleic acid expression cassette, the vector, or the pharmaceutical, wherein the transgene encodes LAMP2, for use in the treatment of Fabry disease.

Also disclosed herein is the use of the Dph-CSk nucleic acid regulatory element, preferably the Dph-CSk nucleic acid regulatory element with a sequence as defined in SEQ ID NO: 3, the nucleic acid expression cassettes, the vectors, or the pharmaceutical compositions as taught herein, wherein the transgene encodes a lysosomal protein, preferably a lysosomal protein selected from the group consisting of acid α-glucosidase (GAA), α-galactosidase A and LAMP2, for the manufacture of a medicament for treating a lysosomal storage disease, preferably a lysosomal storage disease selected from the group consisting of Pompe disease, Fabry disease and Danon disease.

Also disclosed herein is the use of the Dph-CSk nucleic acid regulatory element, preferably the Dph-CSk nucleic acid regulatory element with a sequence as defined in SEQ ID NO: 3, the nucleic acid expression cassettes, the vectors, or the pharmaceutical compositions as taught herein, wherein the transgene encodes acid α-glucosidase (GAA) as defined by SEQ ID NO: 5, more preferably the codon-optimised human acid α-glucosidase gene (hGAAco) as defined by SEQ ID NO: 6, for the manufacture of a medicament for treating Pompe disease.

Also disclosed herein is a method for treating a lysosomal storage disease, preferably a lysosomal storage disease selected from the group consisting of Pompe disease, Fabry disease and Danon disease in a subject comprising:

introducing in the subject, in particular in muscle tissue or cells of the subject, preferably in diaphragm, skeletal muscle, smooth muscle and heart tissue or cells of the subject, more preferably in diaphragm, skeletal muscle and heart tissue or cells of the subject, the Dph-CSk nucleic acid regulatory element, preferably the Dph-CSk nucleic acid regulatory element with a sequence as defined in SEQ ID NO: 3, the nucleic acid expression cassettes, the vectors, or the pharmaceutical compositions as taught herein, wherein the transgene encodes a lysosomal protein, preferably a lysosomal protein selected from the group consisting of acid α-glucosidase (GAA), α-galactosidase A and LAMP2; and expressing a therapeutically effective amount of the lysosomal protein, preferably the lysosomal protein selected from the group consisting of acid α-glucosidase (GAA), α-galactosidase A and LAMP2 in the subject, in particular in the muscle tissue or cells of the subject, preferably in the diaphragm, skeletal muscle, smooth muscle and heart tissue or cells of the subject, more preferably in the diaphragm, skeletal muscle and heart tissue or cells of the subject.

Also disclosed herein is a method for treating Pompe disease in a subject comprising:

introducing in the subject, in particular in muscle tissue or cells of the subject, preferably in diaphragm, skeletal muscle, smooth muscle and heart tissue or cells of the subject, more preferably in diaphragm, skeletal muscle and heart tissue or cells of the subject, the Dph-CSk nucleic acid regulatory element, preferably the Dph-CSk nucleic acid regulatory element with a sequence as defined in SEQ ID NO: 3, the nucleic acid expression cassettes, the vectors, or the pharmaceutical compositions as taught herein, wherein the transgene encodes acid α-glucosidase (GAA) as defined by SEQ ID NO: 5, more preferably the codon-optimised human acid α-glucosidase gene (hGAAco) as defined by SEQ ID NO: 6; and expressing a therapeutically effective amount of GAA, preferably hGAAco in the subject, in particular in the muscle tissue or cells of the subject, preferably in the diaphragm, skeletal muscle, smooth muscle and heart tissue or cells of the subject, more preferably in the diaphragm, skeletal muscle and heart tissue or cells of the subject.

In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of medicament or a vaccine, in particular for the manufacture of a prophylactic vaccine.

Also disclosed herein is a method of vaccination, in particular prophylactic vaccination, of a subject in need of said vaccination comprising:

introducing in the subject, in particular in the muscle cells or tissue of the subject, preferably the diaphragm, smooth muscle, skeletal muscle- and heart-tissue or cells of the subject, a nucleic acid expression cassette, a vector or a pharmaceutical composition as taught herein wherein the nucleic acid expression cassette, the vector or the pharmaceutical composition comprises a Dph-CSk nucleic acid regulatory element as taught herein, operably linked to a promoter and a transgene; and expressing an immunologically effective amount of the transgene product in the subject, in particular in the muscle cells or tissue of the subject, preferably in diaphragm, smooth muscle, skeletal muscle- and heart-cells or tissue of the subject.

As used herein, a phrase such as “a subject in need of treatment” includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms “subject” and “patient” are used interchangeably herein and refer to animals, preferably vertebrates, more preferably mammals, and specifically include human patients and non-human mammals. “Mammalian” subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A "therapeutic amount" or "therapeutically effective amount" as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one nucleic acid regulatory element) are higher than when an identical expression cassette or vector is used but without a nucleic acid regulatory element therein or only comprising (i) the diaphragm-specific nucleic acid regulatory element comprising a sequence having at least 80%, preferably at least 95%, identity to the sequence defined by SEQ ID NO: 1, or a functional fragment thereof, or (ii) the cardiac and skeletal muscle-specific nucleic acid regulatory element comprising a sequence having at least 80%, preferably at least 95%, identity to the sequence defined by SEQ ID NO: 2, or a functional fragment thereof. More particularly, the expression is at least twice as high, at least five times as high, at least ten times as high, at least 20 times as high, at least 30 times as high, at least 40 times as high, at least 50 times as high, or at least 100 times as high as when compared to the same nucleic acid expression cassette or vector without nucleic acid regulatory element or only comprising (i) the diaphragm-specific nucleic acid regulatory element comprising a sequence having at least 80%, preferably at least 95%, identity to the sequence defined by SEQ ID NO: 1, or a functional fragment thereof, or (ii) the cardiac and skeletal muscle-specific nucleic acid regulatory element comprising a sequence having at least 80%, preferably at least 95%, identity to the sequence defined by SEQ ID NO: 2, or a functional fragment thereof.

Preferably, the higher expression remains specific to muscle tissues or cells, more preferably to diaphragm, heart, smooth muscle and skeletal muscle tissues or cells, even more preferably to diaphragm, heart and skeletal muscle tissues or cells.

Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, or at least 300 days or more such as at least 1 year, at least 2 years, at least 3 years, at least 5 years, at least 6 years, at least 7 years, at least 8 years, at least 9 years, or even at least 10 years or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product. Alternatively, for example if the gene product is an enzyme, expression of the enzymatic activity may be determined by measuring the amount of the enzyme's target protein, polypeptide or peptide. For example, if the transgene is a transgene encoding GAA, the enzymatic activity could be determined by any means known in the art, such using the Lysosomal acid alpha-Glucosidase Activity Assay Kit (Fluorometric) (Kit information: Abcam, ab252887). Alternatively, to determine GAA activity, glycogen accumulation can be measured by using the Glycogen Assay Kit II (Colorimetric)(Kit information: ab169558; Abcam UK) or Periodic Acid Schiff (PAS) Stain Kit (Mucin Stain) catalog number ab150680; Abcam UK).

Also disclosed herein is the use of the Dph-CSk nucleic acid regulatory elements, the nucleic acid expression cassettes, or the vectors as taught herein, for transfecting or transducing muscle cells (e.g. diaphragm, skeletal muscle, smooth muscle and/or heart cells, preferably diaphragm, skeletal muscle and/or heart cells).

Further disclosed herein is a method for expressing a transgene product in muscle cells (e.g. diaphragm, skeletal muscle, smooth muscle and/or heart cells, preferably diaphragm, skeletal muscle and heart cells), comprising:

transfecting or transducing said cells with a nucleic acid expression cassette or a vector as taught herein; and expressing the transgene product in said cells.

Non-viral transfection or viral vector-mediated transduction of muscle cells (e.g. diaphragm, skeletal muscle, smooth muscle and/or heart cells, preferably diaphragm, heart, and/or skeletal muscle cells) may be performed by in vitro, ex vivo or in vivo procedures. The in vitro approach requires the in vitro transfection or transduction of muscle cells (e.g. diaphragm, skeletal muscle, smooth muscle and/or heart cells, preferably diaphragm, heart, and/or skeletal muscle cells), e.g. cells previously harvested from a subject, cell lines or cells differentiated from e.g. induced pluripotent stem cells or embryonic cells. The ex vivo approach requires harvesting of the muscle cells (e.g. diaphragm, skeletal muscle, smooth muscle and/or heart cells, preferably diaphragm, heart, and/or skeletal muscle cells) from a subject, in vitro transfection or transduction, and optionally reintroduction of the transfected cells into the subject. The in vivo approach requires the administration of the nucleic acid expression cassette or the vector as taught herein into a subject. In preferred embodiments, the transfection of the muscle cells (e.g. diaphragm, skeletal muscle, smooth muscle and/or heart cells, preferably diaphragm, heart, and/or skeletal muscle cells) is performed in vitro or ex vivo.

It is understood by the skilled person that the use of the Dph-CSk nucleic acid regulatory element, the nucleic acid expression cassette and vector as taught herein has implications beyond gene therapy, e.g. coaxed differentiation of stem cells into muscle cells or tissue (e.g. diaphragm, skeletal muscle, smooth muscle and/or heart cells, preferably diaphragm, skeletal muscle, and heart cells), transgenic models for over-expression of proteins in muscle cells or tissue (e.g. diaphragm, skeletal muscle, smooth muscle and/or heart cells, preferably diaphragm, skeletal muscle, and heart) etc.

The invention is further explained by the following non-limiting examples

EXAMPLES

Example 1: Increased GAA Activity and mRNA Transcription in Different Muscle Groups of Adult Mice Upon Injection of AAVss-Dph-CRE02-CSkSH1-SPc5-12-MVM-hGAAco-SynthpA

Materials and Methods 1.1) Generation of AAV vectors encoding the therapeutic gene hGAAco.

Cloning of the New AAV Vector Designated as AAVss-Dph-CRE02-CSk-SH1-SPc5-12-MVM-hGAAco-pA.

A new adeno-associated viral vector (AAV) (designated as AAVss-Dph-CRE02-CSk-SH1-SPc5-12-MVM-hGAAco-pA for AAV vector or pAAVss-Dph-CRE02-CSk-SH1-SPc5-12-MVM-hGAAco-pA for the corresponding plasmid DNA) (SEQ ID NO 9; FIGS. 1A-1G) was constructed comprising a new combination of CRE elements composed of (i) a diaphragm-specific regulatory element designated as Dph-CRE02 (SEQ ID NO: 1) and (ii) the muscle-specific regulatory element designated as CSk-SH1 (SEQ ID NO: 2) in the context of a single stranded AAV (ssAAV) backbone. This specific new combination of diaphragm and muscle-specific regulatory elements (designated as Dph-CRE02-CSk-SH1) (SEQ ID NO: 3) was cloned upstream of and are operably linked to a muscle-specific human SPc5-12 promoter (SEQ ID NO: 4). To generate the pAAVss-Dph-CRE02-CSk-SH1-SPc5-12-MVM-hGAAco-SynthpA plasmid vector, the Dph-CRE02-CSk-SH1 fragment was synthesized by GeneArt (Germany) and flanked with AgeI and Acc65I restriction sites and cloned upstream of the corresponding restriction sites of the SPc5-12 promoter. The promoter is used to drive expression of the codon-optimized human acid alpha-glucosidase gene (hGAAco). The ssAAV vector backbone also contained a minute virus of mouse (MVM) intron (SEQ ID NO: 7) downstream of the SPc5-12 promoter and a synthetic polyadenylation site (pA) (SEQ ID NO: 8). A control vector (designated as AAVss-SPc5-12-MVM-hGAAco-pA (SEQ ID NO: 10) FIGS. 1A-1G) was generated that is devoid of Dph-CRE02-CSk-SH1 (SEQ ID NO: 3).

1.2) AAV Production and Titration

Production of the AAV vector particles is achieved by transient co-transfection of AAV vector and AAV helper DNA constructs, encoding AAV serotype 9 capsids into HEK293 cells, followed by a purification step based on cesium chloride (CsCl) density gradient ultracentrifugation, as described previously (VandenDriessche et al., 2007 J Thromb Haemost 5:16-24). Briefly, two days post transfection, cells were harvested and vector particles were purified using isopycnic centrifugation methods. Harvested cells were lysed by successive freeze/thaw cycles and sonication, treated with benzonase (Novagen, Madison, WI) and deoxycholic acid (Sigma-Aldrich, St. Louis, MO) and subsequently subjected to 3 successive rounds of cesium chloride (Invitrogen Corp, Carlsbad, CA) density gradient ultracentrifugation. Fractions containing the AAV vector were collected, concentrated in 1 mM $MgCl_2$ in Dulbecco's phosphate buffered saline (PBS) (Gibco, BRL) and stored at −80° C. In addition to the in-house AAV production per protocol, AAV production was sometimes outsourced (SignaGen Laboratories, Gaithersburg US). Vector titers (in viral genomes (vg)/ml) were determined by quantitative real-time PCR (qRT-PCR) using SYBR Green mix (which included SYBR Green dye, Taqman polymerase, ROX and dNTP's all in one) and vector-specific primers on an ABI 7500 Real-Time PCR System (Applied Biosystem, Foster city, CA, USA). The forward and reverse primers used for the AAV vector titration were: 5'-AGG-GATGGTTGGTTGGTGG-3' (SEQ ID NO: 14) and 5'-GGCAGGTGCTCCAGGTAAT-3' (SEQ ID NO: 15) respectively. In addition, another set of primers for titration was also used namely: forward: 5'-CCATCCT-CACGACACCCAA-3' (SEQ ID NO: 16) and reverse: 5' GTCCACCATTCCTCCGCT-3' (SEQ ID NO: 17). Typically, for all vector titers in the range of around 10E11-10E12 vector genomes (vg)/ml were achieved from a small production batch of 30 petri dishes of producer cells. If higher number of petri dishes such as 60 dishes of producer cells were used, a higher titer typically in the range of 10E12-10E13 vg/ml of AAV particles were achieved. Known copy numbers (10E2-10E7) of the respective vector plasmids used to generate the corresponding AAV vectors, carrying the appropriate cDNAs were used to generate the standard curves.

1.3) Animal Studies: GAA Activity, % Glycogen Accumulation and Periodic Acid Schiff (PAS) Assay All animal procedures were approved by the institutional animal ethics committee of the Vrije Universiteit Brussel (VUB) (Brussels, Belgium). All mice were housed under specific pathogen-free (SPF) conditions; food and water were provided ad libitum. The purified AAV vectors were injected intravenously (i.v.) by retro-orbital injection into 36-48 hr neonatal GAAKO mice or by tail vein injection in adult mice, as indicated per protocol. Mouse were euthanized by cervical dislocation and mice were dissected immediately to collect muscle tissues (quadriceps, gastrocnemius, tibialis, biceps, triceps, diaphragm, heart) and non-muscle tissues (liver, kidneys, spleen, lungs and brain). Tissues are washed with Gibco™ DPBS buffer (Life technologies, UK) to remove the blood and immediately snap frozen in liquid nitrogen for 20 seconds and then kept on dry ice. Frozen tissues are stored at −80° C. until further analysis. The glycogen assay was performed using the Glycogen Assay Kit II (Colorimetric) (Kit information: ab169558) purchased from Abcam (UK). Similarly, the GAA activity was performed using the Lysosomal acid alpha-Glucosidase Activity Assay Kit (Fluorometric) (Kit information: ab252887) also purchased from Abcam. In addition, the Periodic Acid Schiff (PAS) assay was performed following the instructions provided by the Abcam company (UK) for the Periodic Acid Schiff (PAS) Stain Kit (Mucin Stain) catalog number ab150680.

1.4) mRNA Quantification

RNA was extracted using AllPrep DNA/RNA Mini Kit (Qiagen, Germany) following the manufacturer's directions. cDNA was synthesized from 200 ng total RNA using SuperScript™ IV First-Strand Synthesis System kit (Invitrogen, USA) following the manufacturer's directions with oligo(dT)20primer. The cDNA was PCR-amplified on StepOne Plus Real-time PCR System (Applied Biosystem, USA) with several primers:

```
                                     (SEQ ID NO: 18)
hGAAco forward primer: 5'-ACCCCTTCATGCCTCCTTAT-3'

                                     (SEQ ID NO: 19)
hGAAco reverse primer: 5'-TCCATGTAGTCCAGGTCGTT-3'

                                     (SEQ ID NO: 20)
GAPDH forward primer: 5'-TGTGTCCGTCGTGGATCTGA-3'
```

-continued

```
                                        (SEQ ID NO: 21)
GAPDH reverse primer: 5'-GCCTGCTTCACCACCTTCTTGA-3'
```

| Components for 1 reaction in qPCR | |
|---|---|
| SYBR ™ Green PCR Master Mix (Applied Biosystem, USA) | 12.5 μL |
| Forward Primer (10 uM) | 0.85 μL |
| Reverse Primer (10 uM) | 0.85 μL |
| $H_2O$ | 8.3 μL |
| cDNA Template | 2.5 μL |
| Total | 25 μL |

Cycling condition in qPCR used is 95° C. in 10 min, followed by 40 cycles of 95° C. in 15 sec and 60° C. in 1 min. Each sample was done in triplicate. ΔCt was calculated by subtracting the Ct of the control gene GAPDH from the Ct of the gene of interest hGAAco for each tissue. The ΔCt of the control tissue sample (PBS) was subtracted from the ΔCt of the corresponding experimental tissue sample, resulting in ΔΔCt for each tissue of different treated groups. The relative expression was calculated as $2^{-\Delta\Delta Ct}$ and plotted in the graph.

1.5) Experimental Design:

The experiment design consisted of three groups of mice namely:

Group 1) injected with (AAVss-Dph-CRE02-CSkSH1-SPc5-12-MVM-hGAAco-pA) (SEQ ID NO: 9)

Group 2) injected with (AAVss-SPc5-12-MVM-hGAAco-pA) (SEQ ID NO: 10)

Group 3) injected with PBS (negative control mice)

1.3 months old adult B6; 129-GAAtm1Rabn/J mice were injected with AAV9 vectors or PBS as indicated above (Group 1-3) by tail vein intravenous injection with a standardised vector dose of 1×10E12 vector genome per mouse. The titration of the AAV vectors were performed by qPCR using the following primers: forward: 5'-CCATCCTCACGACACCCAA-3'(SEQ ID NO: 16) and reverse: 5'-GTCCACCATTCCTCCGCT-3'(SEQ ID NO: 17). 1.8 months post AAV vector injection, the three groups of mice were killed and individual organs were isolated and frozen for subsequent analysis. GAA activity, % glycogen and mRNA quantification were determined on different tissues and two mice were analysed per cohort.

Figure 3:
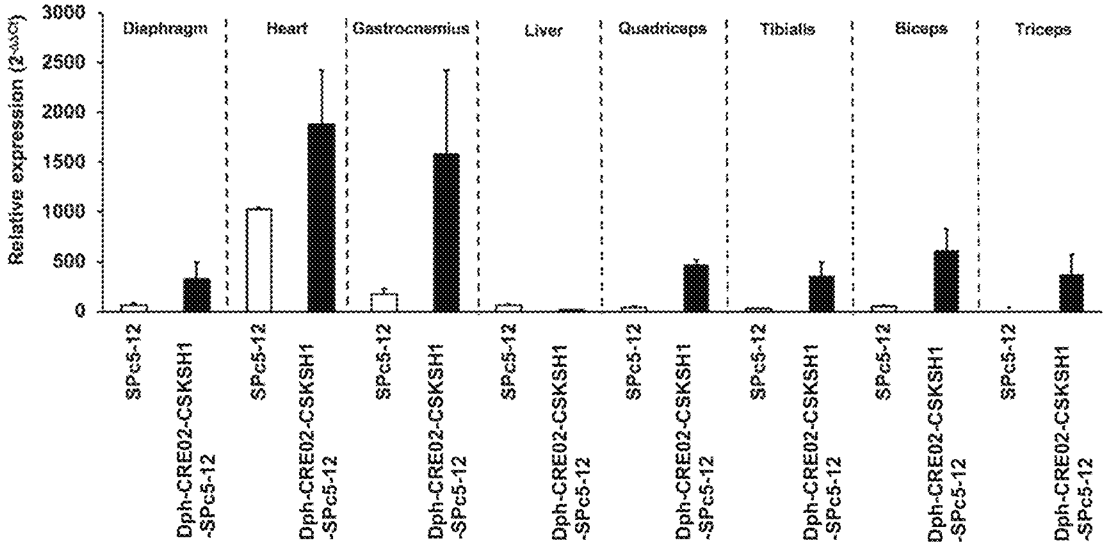
FIG. 3: mRNA expression in GAA KO-mice injected with AAVss-Dph-CRE02-CSkSH1-SPc5-12-MVM-hGAAco-pA (SEQ ID NO: 9) ("Dph-CRE02-CSKSH1-SPc5-12") or AAVss-SPc5-12-MVM-hGAAco-pA (SEQ ID NO: 10) ("SPc5-12").
Figure 4:
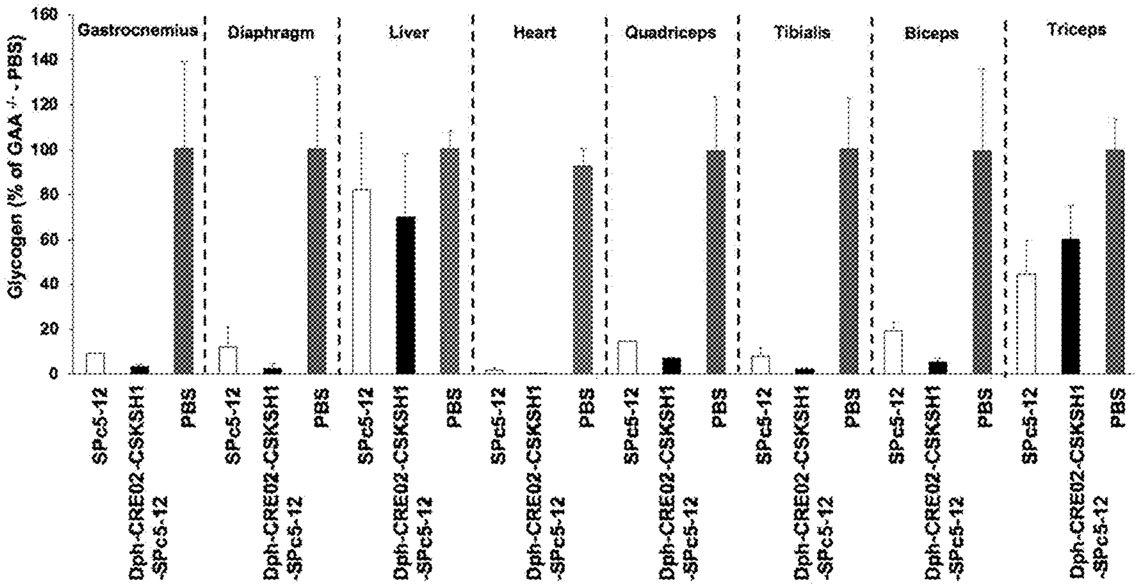
FIG. 4: Percentage glycogen accumulation relative to PBS-injected GAA KO-mice injected with AAVss-Dph-CRE02-CSkSH1-SPc5-12-MVM-hGAAco-pA (SEQ ID NO: 9) ("Dph-CRE02-CSKSH1-SPc5-12"), AAVss-SPc5-12-MVM-hGAAco-pA (SEQ ID NO: 10) ("SPc5-12") or PBS.

1.6) Results and Conclusions:

The results (FIGS. 2 and 3) demonstrate that the incorporation of the CRE combination (i.e. Dph-CRE02-CSk-SH1) into the AAV-hGAAco vector (i.e. AAVss-SPc5-12-MVM-hGAAco-pA) boosts vector performance resulting in increased GAA activity and mRNA expression, notably in the different muscle groups, including diaphragm, heart, gastrocnemius, quadriceps, tibialis, biceps and triceps. Moreover, GAA activity correlates with a reduction of glycogen accumulation in the transduced tissues (FIG. 4).

Example 2: Increased GAA Activity in Different Muscle Groups of Neonatal Mice Upon Injection of AAVss-Dph-CRE02-CSkSH1-SPc5-12-MVM-hGAAco-SynthpA 2.1)-2.4) Generation of AAV vectors encoding the therapeutic gene hGAAco, AAV production and titration, animal studies (GAA activity, % glycogen accumulation and Periodic Acid Schiff (PAS) assay), and mRNA quantification were performed as indicated in Example 1.

2.5) Experimental Design:

The experiment design consisted of three groups of mice namely:

Group 1) injected with AAVss-Dph-CRE02-CSkSH1-SPc5-12-MVM-hGAAco-SynthpA (SEQ ID NO: 9)

Group 2) injected with PBS (negative control mice)

Group 3) non-injected WT (positive control mice, GAA+/+)

Neonatal B6; 129-GAAtm1Rabn/J mice (36-48 hrs after birth) were injected with AAV9 vectors (group 1) or PBS (group 2) by retro orbital injection with standardised 2×10E11 vector genome (AAV vector produced by SignaGen Laboratories, Gaithersburg US) per neonatal mouse. The titration of the AAV vectors by qPCR were performed using the following primers: forward: 5'-CCATCCTCACGACACCCAA-3' (SEQ ID NO: 16) and reverse: 5' GTCCACCATTCCTCCGCT-3' (SEQ ID NO: 17). 22 days post injection, the 3 groups of mice were killed and individual organs were isolated and frozen for subsequent analysis. GAA activity and % glycogen were determined on different tissues and one mouse was analysed per cohort.

Figure 5:
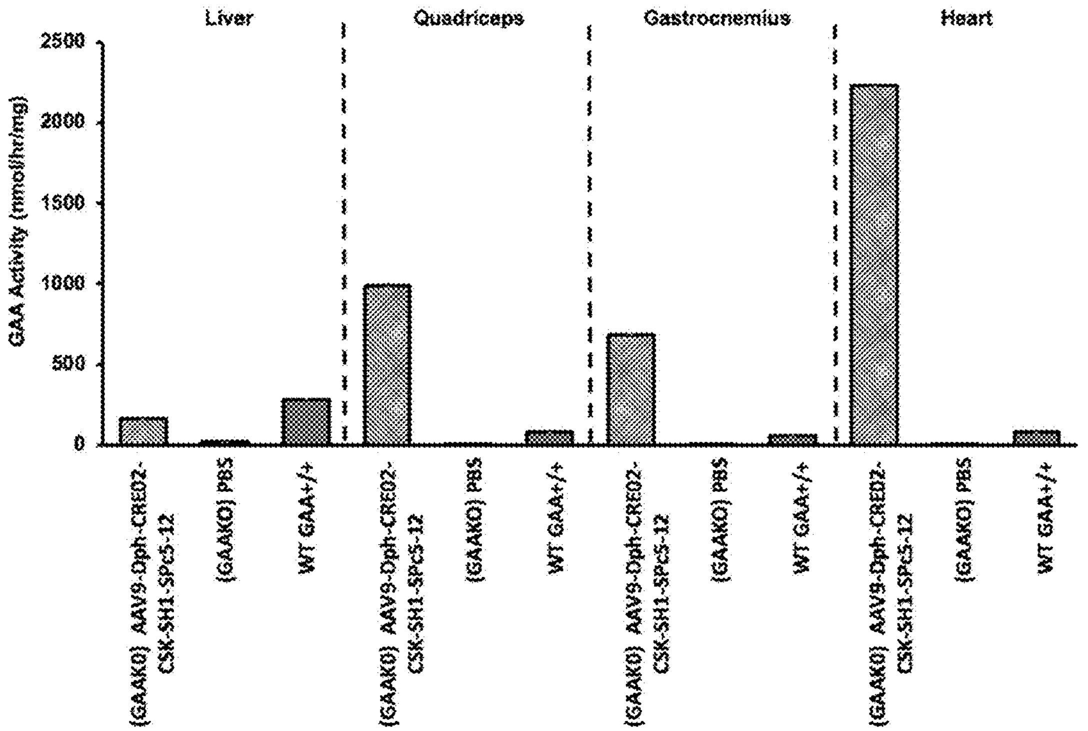
FIG. 5: GAA activity in GAA KO-mice injected with AAVss-Dph-CRE02-CSkSH1-SPc5 MVM-hGAAco-pA (SEQ ID NO: 9) ("AAV9-Dph-CRE02-CSK-SH1-SPc5-12") or PBS. Non-injected WT GAA+/+ mice served as control mice.
Figure 6:
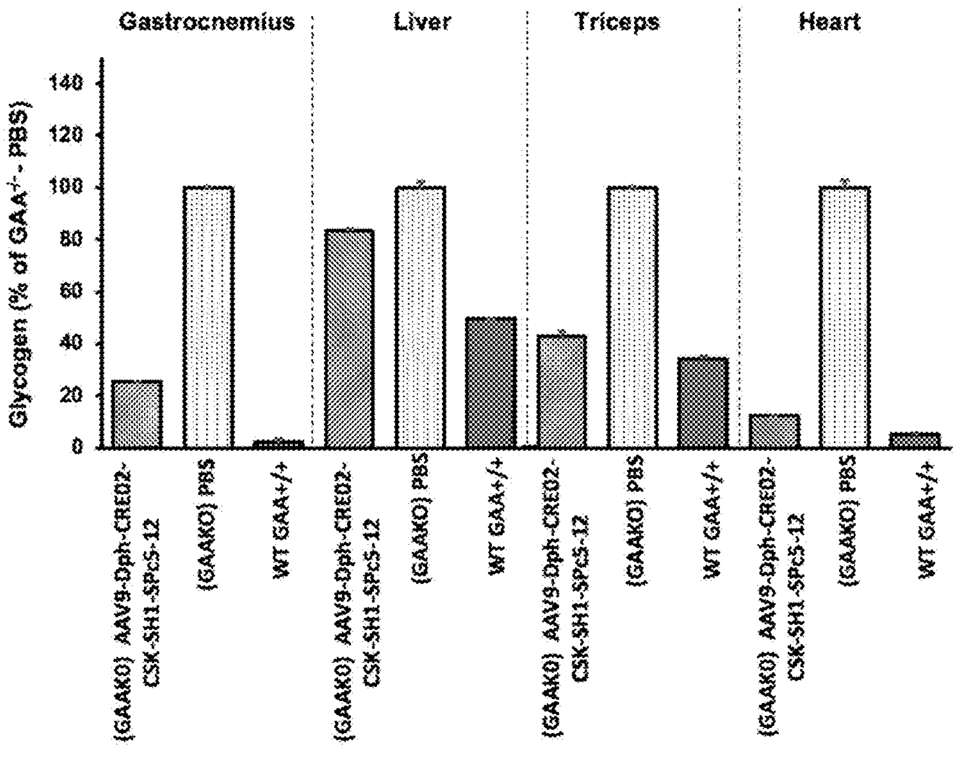
FIG. 6: Percentage glycogen accumulation relative to PBS-injected GAA KO-mice injected with AAVss-Dph-CRE02-CSkSH1-SPc5-12-MVM-hGAAco-pA (SEQ ID NO: 9) ("AAV9-Dph-CRE02-CSK-SH1-SPc5-12"), PBS or WT GAA+/+ mice.

2.6) Results and Conclusions:

The results in (FIG. 5) demonstrate that the incorporation of the CRE combination (i.e. Dph-CRE02-CSk-SH1) into the AAV-hGAAco vector (i.e. AAVss-SPc5-12-MVM-hGAAco-pA) boosts vector performance resulting in increased GAA activity (in the supra-physiologic range, i.e. >wild-type), notably in the different muscle groups, including diaphragm, heart, gastrocnemius, quadriceps, tibialis, biceps and triceps. Moreover, GAA activity correlates with a reduction of glycogen accumulation (FIG. 6) in the transduced tissues.

Example 3: Increased GAA Activity and mRNA Expression in Different Muscle Groups of Neonatal Mice Upon Injection with AAVss-Dph-CRE02-CSkSH1-SPc5-12-MVM-hGAAco-SynthpA 3.1-3.4) Generation of AAV vectors encoding the therapeutic gene hGAAco, AAV production and titration, animal studies (GAA activity, % glycogen accumulation and Periodic Acid Schiff (PAS) assay), and mRNA quantification were performed as indicated in Example 1.

3.5) The Experiment Design Consisted of Four Groups of Mice Namely:

Group 1) injected with AAVss-Dph-CRE02-CSkSH1-SPc5-12-MVM-hGAAco-SynthpA (SEQ ID NO: 9)

Group 2) injected with AAVss-SPc5-12-MVM-hGAAco-SynthpA (SEQ ID NO: 10)

Group 3) injected with PBS (negative control mice)

Group 4) non injected WT (positive control mice, GAA+/+)

Neonatal B6; 129-GAAtm1Rabn/J mice (36-48 hrs after birth) were injected with AAV9 vectors (group 1, 2) or PBS (group 3) by retro orbital injection with standardised 1.5×10E11 vector genome (vg) copies (AAV vectors produced in-house) per neonatal mouse. The titration of the AAV vectors by qPCR was performed using the following primers: Forward primer 5'-AGGGATGGTTGGTTGGTGG-3' (SEQ ID NO: 14) and Reverse primer 5'-GGCAGGTGCTCCAGGTAAT-3' (SEQ ID NO: 15). 1.5 months post injection, the 4 groups of mice were sacrificed and individual organs were isolated and frozen for subsequent analysis. GAA activity, mRNA expression, % glycogen and the Periodic Acid Schiff (PAS) assay were determined on different tissues and one mouse was analysed per cohort.

Figure 8:
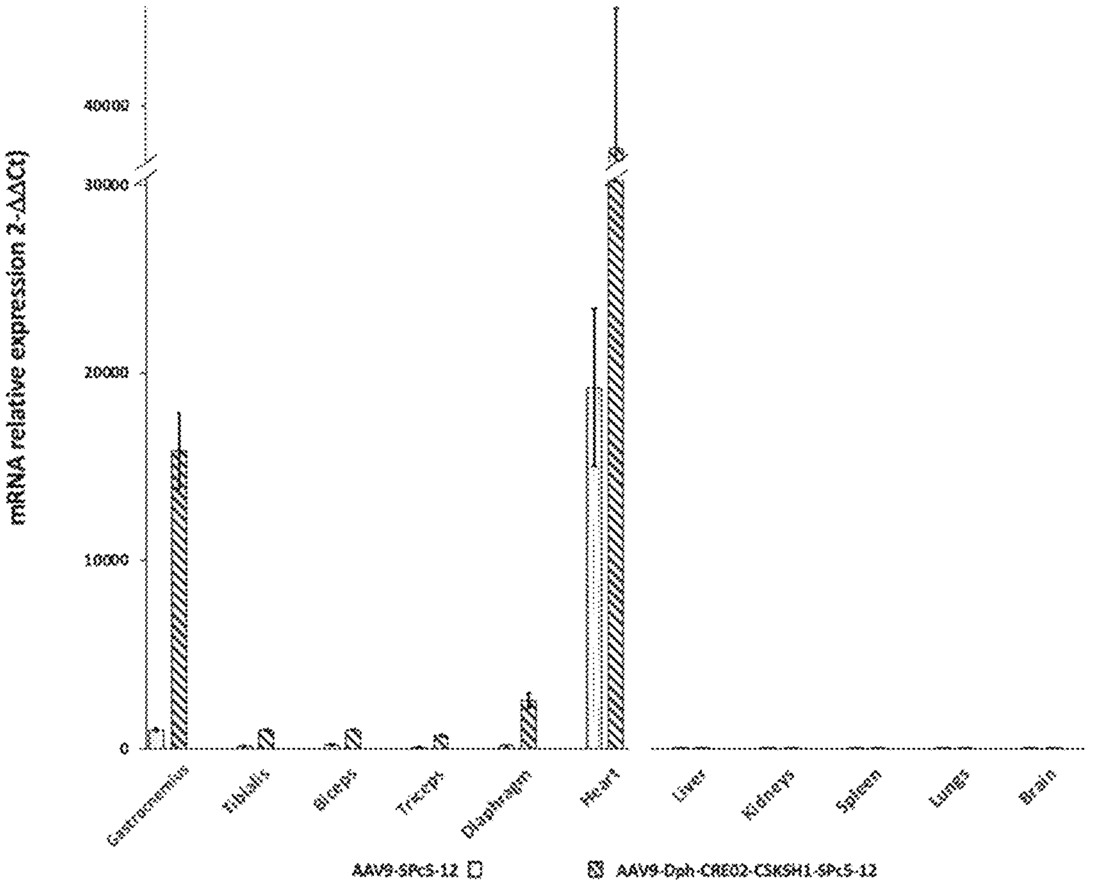
FIG. 8: mRNA expression in GAA KO-mice injected with AAVss-Dph-CRE02-CSkSH1-SPc5-12-MVM-hGAAco-pA (SEQ ID NO: 9) ("AAV9-Dph-CRE02-CSKSH1-SPc5-12"), AAVss-SPc5-12-MVM-hGAAco-pA (SEQ ID NO: 10) ("AAV9-SPc5-12").
Figure 9A:
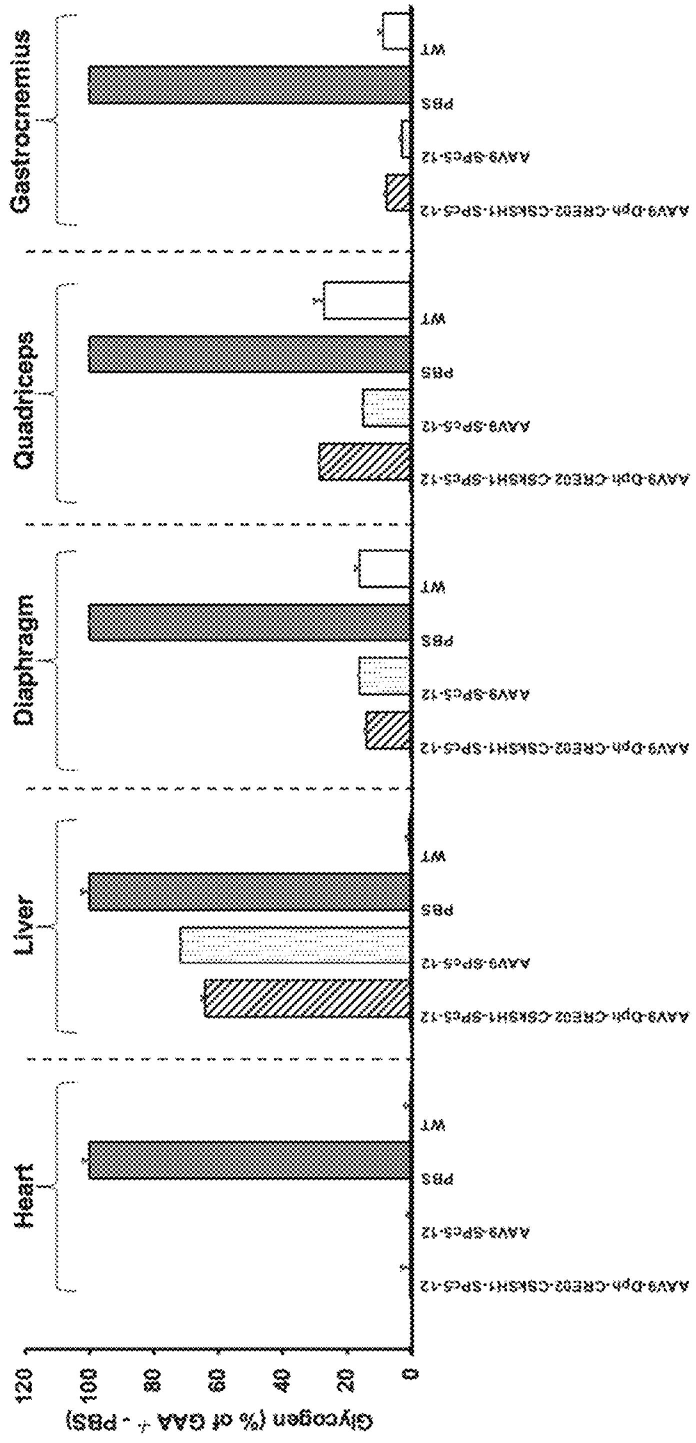
FIGS. 9A-9B: Collectively illustrate percentage glycogen accumulation relative to PBS-injected GAA KO-mice injected with AAVss-Dph-CRE02-CSkSH1-SPc5-12-MVM-hGAAco-pA (SEQ ID NO: 9) ("AAV9-Dph-CRE02-CSKSH1-SPc5-12"), AAVss-SPc5-12-MVM-hGAAco-pA (SEQ ID NO: 10) ("AAV9-SPc5-12"), PBS and non injected WT GAA+/+ mice ("WT").
Figure 9B:
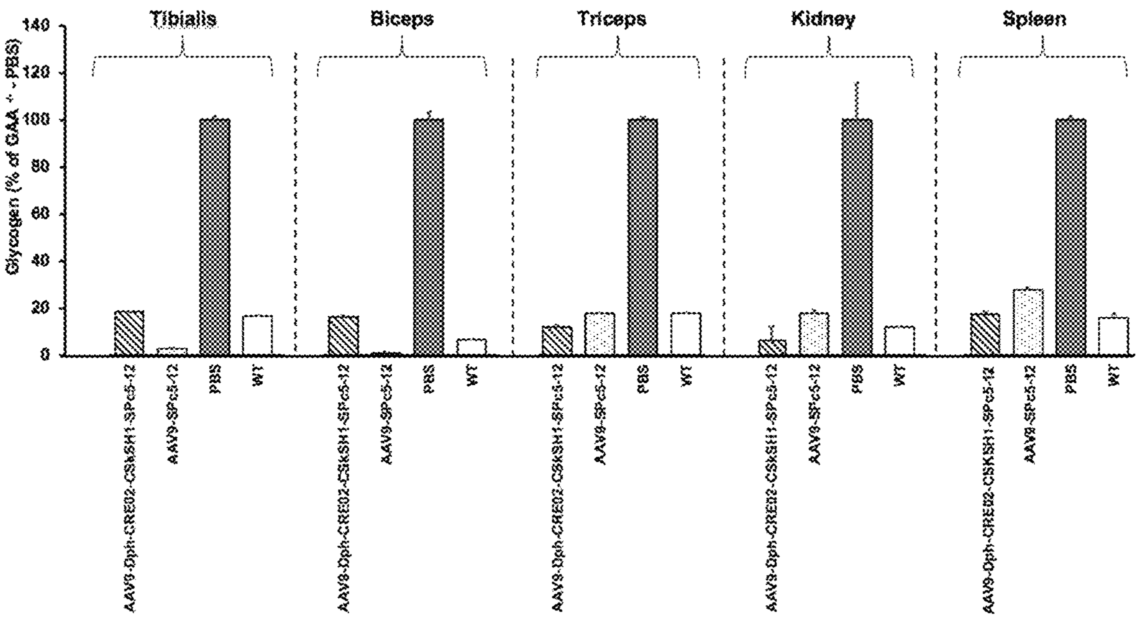
Figure 10:
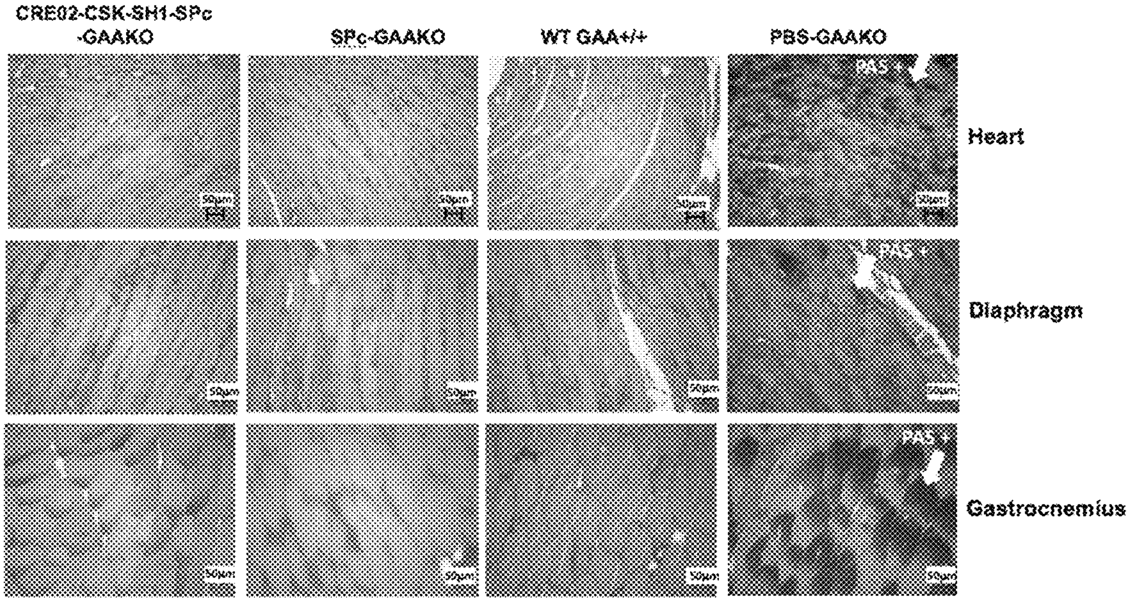
FIG. 10: Periodic Acid Schiff (PAS) assay performed in heart, diaphragm and gastrocnemius of GAA KO-mice injected with AAVss-Dph-CRE02-CSkSH1-SPc5-12-MVM-hGAAco-pA (SEQ ID NO: 9) ("CRE02-CSK-SH1-SPc5-GAAKO"), AAVss-SPc5-12-MVM-hGAAco-pA (SEQ ID NO: 10) ("SPc-GAAKO"), PBS ("PBS-GAAKO") and non injected WT GAA+/+ mice ("WT GAA+/+"). Dark grey/black coloring (see arrowheads) indicates PAS positive as seen in all three organs (heart, diaphragm, gastrocnemius) of GAAKO mice injected with PBS. In contrast, AAV vector (CRE02-CSKSH1-SPc5-12 or SPc) injected organs showed no PAS positivity or magenta color, showing similar observation as WT GAA+/+ mice.

3.6) Results and Conclusions:

The results in (FIGS. 7 and 8) demonstrate that the incorporation of the CRE combination (i.e. Dph-CRE02-CSk-SH1) into the AAV-hGAAco vector (i.e. AAVss-SPc5-12-MVM-hGAAco-pA) boosts vector performance resulting in increased GAA activity and mRNA expression, notably in the different muscle groups, including diaphragm, heart, gastrocnemius, quadriceps, tibialis, biceps and triceps. Moreover, GAA activity correlates with a reduction of glycogen accumulation (FIGS. 9A-B) in the transduced tissues. The reduction of glycogen by this gene therapy approach was further confirmed by a substantial reduction in PAS+ staining (FIG. 10).

Example 4: Increased GAA Activity and mRNA Expression in Different Muscle Groups of Adult and/or Neonatal Mice Upon Injection with AAVss-Dph-CRE02-CSkSH1-SPc5-12-MVM-hGAAwt-SynthpA 4.1-4.4) Generation of AAV vectors encoding the therapeutic gene hGAAwt, AAV production and titration, animal studies (GAA activity, % glycogen accumulation and Periodic Acid Schiff (PAS) assay), and mRNA quantification were performed as indicated in Example 1. In particular, hGAAco from AAVss-Dph-CRE02-CSkSH1-SPc5-12-MVM-hGAAco-SynthpA was restricted with enzymes BsiWI and AvrII, then ligated with hGAAwt fragment which was obtained by restriction digestion of plasmid AAVss-SPc5-12-MVM-hGAAwt-SynthpA with enzymes BsiWI and AvrII.

4.5) The Experiment Design Consisted of Four Groups of Mice Namely:

Group 1) injected with AAVss-Dph-CRE02-CSkSH1-SPc5-12-MVM-hGAAwt-SynthpA (SEQ ID NO: 11)

Group 2) injected with AAVss-SPc5-12-MVM-hGAAwt-SynthpA (SEQ ID NO: 12)

Group 3) injected with PBS (negative control mice)

Group 4) non injected WT (positive control mice, GAA+/+)

1.3 month old adult B6; 129-GAAtm1Rabn/J and/or neonatal B6; 129-GAAtm1Rabn/J mice (36-48 hrs after birth) are injected with AAV9 vectors (group 1, 2) or PBS (group 3) by retro orbital injection with standardised 1×10E12 vector genome per adult mouse or 1.5×10E11 vector genome (vg) copies (AAV vectors produced in-house) per neonatal mouse. At least 1.5 months post injection, the 4 groups of mice are sacrificed and individual organs are isolated and frozen for subsequent analysis. GAA activity, mRNA expression, % glycogen and the Periodic Acid Schiff (PAS) assay are determined on different tissues and one mouse was analysed per cohort.

The invention claimed is:

1. A nucleic acid regulatory element for enhancing muscle-specific gene expression comprising:

(i) a diaphragm-specific nucleic acid regulatory element comprising a sequence defined by SEQ ID NO: 1; and (ii) a cardiac and skeletal muscle-specific nucleic acid regulatory element comprising a sequence defined by SEQ ID NO: 2.

2. The nucleic acid regulatory element according to claim 1, comprising the nucleotide sequence set forth in SEQ ID NO: 3.

3. A nucleic acid expression cassette comprising the nucleic acid regulatory element according to claim 1 operably linked to a promoter.

4. The nucleic acid expression cassette according to claim 3, wherein the promoter is the SPc5-12 promoter.

5. The nucleic acid expression cassette according to claim 3, wherein the nucleic acid regulatory element is operably linked to a transgene.

6. The nucleic acid expression cassette according to claim 5, wherein the transgene encodes a lysosomal protein selected from the group consisting of acid α-glucosidase (GAA), α-galactosidase A and lysosome-associated membrane protein 2 (LAMP2).

7. The nucleic acid expression cassette according to claim 3, further comprising an intron.

8. The nucleic acid expression cassette according to claim 3, further comprising a polyadenylation signal.

9. A vector comprising the nucleic acid expression cassette according to claim 3.

10. The vector according to claim 9, comprising (i) a diaphragm-specific nucleic acid regulatory element comprising a sequence defined by SEQ ID NO: 1; (ii) a cardiac and skeletal muscle-specific nucleic acid regulatory element comprising a sequence defined by SEQ ID NO: 2; (iii) the MVM intron as defined by SEQ ID NO: 7; (iv) the SPc5-12 promoter as defined by SEQ ID NO: 4; (v) the human GAA transgene as defined by SEQ ID NO: 5 or the codon optimized variant thereof as defined by SEQ ID NO: 6; and (vi) the synthetic poly A site as defined by SEQ ID NO: 8.

11. A pharmaceutical composition comprising the nucleic acid expression cassette according to claim 3.

12. The nucleic acid expression cassette according to claim 3, wherein the promoter is a nucleic acid-specific promoter selected from the group consisting of the desmin (DES) promoter; the synthetic SPc5-12 promoter (SPc5-12); the alpha-actin1 promoter (ACTA1); the Creatine kinase, muscle (CKM) promoter; the Four and a half LIM domains protein 1 (FHL1) promoter; the alpha 2 actinin (ACTN2) promoter; the filamin-C (FLNC) promoter; the sarcoplasmic/endoplasmic reticulum calcium ATPase 1 (ATP2A1) promoter; the Troponin I Type 1 (TNNI1) promoter; the Troponin I Type 2 (TNNI2) promoter; the Troponin T Type 3 (TNNT3) promoter; the myosin-1 (MYH1) promoter; the phosphorylatable, fast skeletal muscle myosin light chain (MYLPF) promoter; the Tropomyosin 1 (TPM1) promoter; the Tropomyosin 2 (TPM2) promoter; the alpha-3 chain tropomyosin (TPM3) promoter; the ankyrin repeat domain-containing protein 2 (ANKRD2) promoter; the myosin heavy-chain (MHC) promoter; the myosin light-chain (MLC) promoter; the muscle creatine kinase (MCK) promoter; the Myosin, Light Chain 1 (MYL1) promoter; the Myosin, Light Chain 2 (MYL2) promoter; the Myoglobin (MB) promoter; the Troponin T type 2, cardiac type (TNNT2) promoter, the Troponin C Type 2 (fast) (TNNC2) promoter, the Troponin C Type 1 (TNNC1) promoter; the Titin-Cap (TCAP) promoter; the Myosin, Heavy Chain 7 (MYH7) promoter; the Aldolase A (ALDOA) promoter; the dMCK promoter, the tMCK promoter, the MHCK7 promoter, the Troponin T Type 1 (TNNT1) promoter, the myosin-2 (MYH2) promoter, the sarcolipin (SLN) promoter, the myosin binding protein C1 (MYBPC1) promoter, the enolase (EN03) promoter, the alpha myosin heavy chain promoter (αMHC) promoter, the carbonic anhydrase 3

(CA3) promoter, the myosin heavy chain 11 (Myh11) promoter, the transgelin (Tagln) and the actin alpha 2 smooth muscle (Acta2) promoter.

13. A method for expressing a transgene product in muscle cells comprising:

i. introducing the nucleic acid expression cassette according to claim 3 into said muscle cells; and ii. expressing the transgene product in the muscle cells.

* * * * *

SEQUENCE LISTING

```
<160> NUMBER OF SEQ ID NOS: 23

<210> SEQ ID NO 1
<211> LENGTH: 452
<212> TYPE: DNA
<213> ORGANISM: Artificial Sequence
<220> FEATURE:
<223> OTHER INFORMATION: Dph-CRE02

<400> SEQUENCE: 1

gacaggtgcg gttcccggag cgcaggcgca cacatgcacc caccggcgaa cgcggtgacc     60

ctcgccccac cccatcccct ccggcgggca actgggtcgg gtcaggaggg gcaaacccgc    120

tagggagaca ctccatatac ggcccggccc gcgttacctg ggaccgggcc aacccgctcc    180

ttctttggtc aacgcagggg acccgggcgg gggcccaggc cgcgaaccgg ccgagggagg    240

gggctctagt gcccaacacc caaatatggc tcgagaaggg cagcgacatt cctgcggggt    300

ggcgcggagg gaatgcccgc gggctatata aaacctgagc agagggacaa gcggccaccg    360

cagcggacag cgccaagtga agcctcgctt cccctccgcg gcgaccaggg cccgagccga    420

gagtagcagt tgtagctacc cgcccaggta gg                                   452


<210> SEQ ID NO 2
<211> LENGTH: 381
<212> TYPE: DNA
<213> ORGANISM: Artificial Sequence
<220> FEATURE:
<223> OTHER INFORMATION: CSKSH1

<400> SEQUENCE: 2

gttctcctct ataaataccc gctctggtat ttggggttgg cagctgttgc tgccagggag     60

atggttgggt tgacatgcgg ctcctgacaa aacacaaacc cctggtgtgt gtgggcgtgg    120

gtggtgtgag tagggggatg aatcagggag ggggcggggg acccaggggg caggagccac    180

acaaagtctg tgcgggggtg ggagcgcaca tagcaattgg aaactgaaag cttatcagac    240
```

cctttctgga aatcagccca ctgtttataa acttgaggcc ccaccctcga cagtaccggg 300
gaggaagagg gcctgcacta gtccagaggg aaactgaggc tcagggctag ctcgcccata 360
gacatacatg gcaggcaggc t 381

<210> SEQ ID NO 3
<211> LENGTH: 847
<212> TYPE: DNA
<213> ORGANISM: Artificial Sequence
<220> FEATURE:
<223> OTHER INFORMATION: Dph-CRE02-CSKSH1

<400> SEQUENCE: 3
gacaggtgcg gttcccggag cgcaggcgca cacatgcacc caccggcgaa cgcggtgacc 60
ctcgccccac cccatcccct ccggcgggca actgggtcgg gtcaggaggg gcaaacccgc 120
tagggagaca ctccatatac ggcccggccc gcgttacctg ggaccgggcc aacccgctcc 180
ttctttggtc aacgcagggg acccgggcgg gggcccaggc cgcgaaccgg ccgagggagg 240
gggctctagt gcccaacacc caaatatggc tcgagaaggg cagcgacatt cctgcggggt 300
ggcgcggagg gaatgcccgc gggctatata aaacctgagc agagggacaa gcggccaccg 360
cagcggacag cgccaagtga agcctcgctt cccctccgcg gcgaccaggg cccgagccga 420
gagtagcagt tgtagctacc cgcccaggta ggggcgcgcc acgcgtgttc tcctctataa 480
atacccgctc tggtatttgg ggttggcagc tgttgctgcc agggagatgg ttgggttgac 540
atgcggctcc tgacaaaaca caaacccctg gtgtgtgtgg gcgtgggtgg tgtgagtagg 600
gggatgaatc agggaggggg cgggggaccc agggggcagg agccacacaa agtctgtgcg 660
ggggtgggag cgcacatagc aattggaaac tgaaagctta tcagaccctt tctggaaatc 720
agcccactgt ttataaactt gaggccccac cctcgacagt accggggagg aagagggcct 780
gcactagtcc agagggaaac tgaggctcag ggctagctcg cccatagaca tacatggcag 840
gcaggct 847

<210> SEQ ID NO 4
<211> LENGTH: 334
<212> TYPE: DNA
<213> ORGANISM: Artificial Sequence
<220> FEATURE:
<223> OTHER INFORMATION: SPc5-12

<400> SEQUENCE: 4
tggccaccgc cttcggcacc atcctcacga cacccaaata tggcgacggg tgaggaatgg 60
tggggagtta tttttagagc ggtgaggaag gtgggcaggc agcaggtgtt ggcgctctaa 120
aaataactcc cgggagttat ttttagagcg gaggaatggt ggacacccaa atatggcgac 180
ggttcctcac ccgtcgccat atttgggtgt ccgccctcgg ccggggccgc attcctgggg 240
gccgggcggt gctcccgccc gcctcgataa aaggctccgg ggccggcggc ggcccacgag 300
ctacccggag gagcgggagg cgccaagctc taga 334

<210> SEQ ID NO 5
<211> LENGTH: 2859
<212> TYPE: DNA
<213> ORGANISM: Homo sapiens

<400> SEQUENCE: 5
atgggagtga ggcacccgcc ctgctcccac cggctcctgg ccgtctgcgc cctcgtgtcc 60
ttggcaaccg ctgcactcct ggggcacatc ctactccatg atttcctgct ggttccccga 120

```
gagctgagtg gctcctcccc agtcctggag gagactcacc cagctcacca gcagggagcc    180
agcagaccag ggccccggga tgcccaggca caccccggcc gtcccagagc agtgcccaca    240
cagtgcgacg tccccccaa cagccgcttc gattgcgccc ctgacaaggc catcacccag    300
gaacagtgcg aggcccgcgg ctgttgctac atccctgcaa agcaggggct gcagggagcc    360
cagatggggc agccctggtg cttcttccca cccagctacc ccagctacaa gctggagaac    420
ctgagctcct ctgaaatggg ctacacggcc accctgaccc gtaccacccc caccttcttc    480
cccaaggaca tcctgaccct gcggctggac gtgatgatgg agactgagaa ccgcctccac    540
ttcacgatca aagatccagc taacaggcgc tacgaggtgc ccttggagac cccgcatgtc    600
cacagccggg caccgtcccc actctacagc gtggagttct ccgaggagcc cttcggggtg    660
atcgtgcgcc ggcagctgga cggccgcgtg ctgctgaaca cgacggtggc gcccctgttc    720
tttgcggacc agttccttca gctgtccacc tcgctgccct cgcagtatat cacaggcctc    780
gccgagcacc tcagtcccct gatgctcagc accagctgga ccaggatcac cctgtggaac    840
cgggaccttg cgcccacgcc cggtgcgaac ctctacgggt ctcacccttt ctacctggcg    900
ctggaggacg gcgggtcggc acacggggtg ttcctgctaa acagcaatgc catggatgtg    960
gtcctgcagc cgagccctgc ccttagctgg aggtcgacag gtgggatcct ggatgtctac   1020
atcttcctgg gcccagagcc caagagcgtg gtgcagcagt acctggacgt tgtgggatac   1080
ccgttcatgc cgccatactg gggcctgggc ttccacctgt gccgctgggg ctactcctcc   1140
accgctatca cccgccaggt ggtggagaac atgaccaggg cccacttccc cctggacgtc   1200
cagtggaacg acctggacta catggactcc cggagggact tcacgttcaa caaggatggc   1260
ttccgggact tcccggccat ggtgcaggag ctgcaccagg gcggccggcg ctacatgatg   1320
atcgtggatc ctgccatcag cagctcgggc cctgccggga gctacaggcc ctacgacgag   1380
ggtctgcgga gggggtttt catcaccaac gagaccggcc agccgctgat tgggaaggta   1440
tggcccgggt ccactgcctt ccccgacttc accaacccca cagccctggc ctggtgggag   1500
gacatggtgg ctgagttcca tgaccaggtg cccttcgacg gcatgtggat tgacatgaac   1560
gagccttcca acttcatcag ggctctgag gacggctgcc ccaacaatga gctggagaac   1620
ccaccctacg tgcctggggt ggttgggggg accctccagg cggccaccat ctgtgcctcc   1680
agccaccagt ttctctccac acactacaac ctgcacaacc tctacggcct gaccgaagcc   1740
atcgcctccc acagggcgct ggtgaaggct cgggggacac gcccatttgt gatctcccgc   1800
tcgacctttg ctggccacgg ccgatacgcc ggccactgga cgggggacgt gtggagctcc   1860
tgggagcagc tcgcctcctc cgtgccagaa atcctgcagt ttaacctgct gggggtgcct   1920
ctggtcgggg ccgacgtctg cggcttcctg ggcaacacct cagaggagct gtgtgtgcgc   1980
tggacccagc tgggggcctt ctaccccttc atgcggaacc acaacagcct gctcagtctg   2040
ccccaggagc cgtacagctt cagcgagccg gcccagcagg ccatgaggaa ggccctcacc   2100
ctgcgctacg cactcctccc ccacctctac acactgttcc accaggccca cgtcgcgggg   2160
gagaccgtgg cccggcccct cttcctggag ttccccaagg actctagcac ctggactgtg   2220
gaccaccagc tcctgtgggg ggaggccctg ctcatcaccc cagtgctcca ggccgggaag   2280
gccgaagtga ctggctactt cccttgggc acatggtacg acctgcagac ggtgccagta   2340
gaggcccttg gcagcctccc acccccacct gcagctcccc gtgagccagc catccacagc   2400
gaggggcagt gggtgacgct gccggccccc ctggacacca tcaacgtcca cctccgggct   2460
```

```
gggtacatca tccccctgca gggccctggc ctcacaacca cagagtcccg ccagcagccc   2520

atggccctgg ctgtggccct gaccaagggt ggggaggccc gaggggagct gttctgggac   2580

gatggagaga gcctggaagt gctggagcga ggggcctaca cacaggtcat cttcctggcc   2640

aggaataaca cgatcgtgaa tgagctggta cgtgtgacca gtgagggagc tggcctgcag   2700

ctgcagaagg tgactgtcct gggcgtggcc acggcgcccc agcaggtcct ctccaacggt   2760

gtccctgtct ccaacttcac ctacagcccc gacaccaagg tcctggacat ctgtgtctcg   2820

ctgttgatgg gagagcagtt tctcgtcagc tggtgttag                          2859


<210> SEQ ID NO 6
<211> LENGTH: 2859
<212> TYPE: DNA
<213> ORGANISM: Artificial Sequence
<220> FEATURE:
<223> OTHER INFORMATION: Codon optimized human acid alpha-glucosidase
      (hGAAco)

<400> SEQUENCE: 6

atgggcgtca gacatcctcc atgttctcac agactgctgg ccgtgtgtgc tctggtgtct     60

cttgctacag ctgccctgct gggacatatc ctgctgcacg attttctgct ggtgcccaga    120

gagctgtctg gcagctctcc tgtgctggaa gaaacacacc ctgcacatca gcagggcgcc    180

tctagacctg gacctagaga tgctcaagcc catcctggca gacctagagc cgtgcctaca    240

cagtgtgacg tgccacctaa cagcagattc gactgcgccc ctgacaaggc catcacacaa    300

gagcagtgtg aagccagagg ctgctgctac attcctgcca aacaaggact gcagggcgct    360

cagatgggac agccttggtg cttcttccca ccatcttacc ccagctacaa gctggaaaac    420

ctgagcagca gcgagatggg ctacaccgcc acactgacca gaaccacacc tacattcttc    480

ccaaaggaca tcctgacact gcggctggac gtgatgatgg aaaccgagaa ccggctgcac    540

ttcaccatca aggaccccgc caatagaaga tacgaggtgc ccctggaaac ccctcacgtg    600

cactctagag ccccatctcc actgtacagc gtggaattca gcgaggaacc ctttggcgtg    660

atcgtgcgga gacagctgga tggcagagtg ctgctgaata ccacagtggc ccctctgttc    720

ttcgccgacc agtttctgca gctgagcaca agcctgccta gccagtatat cacaggcctg    780

gccgaacacc tgtctccact gatgctgagc accagctgga ccagaatcac cctgtggaac    840

agagatctgg cccctacacc tggcgccaat ctgtacggct ctcacccttt ttatctggcc    900

ctggaagatg gcggaagcgc ccacggtgtc tttctgctga acagcaacgc catggacgtg    960

gtgctgcaac catctcctgc tctgtcttgg agaagcaccg gcggcatcct ggacgtgtac   1020

atctttctgg gacccgagcc taagagcgtg gtgcagcagt atctggatgt cgtgggctac   1080

cccttcatgc ctccttattg ggcctgggc ttccacctgt gtagatgggg atacagctcc   1140

accgccatca ccagacaggt ggtggaaaac atgacccggg ctcacttccc actggatgtg   1200

cagtggaacg acctggacta catggactcc agacgggact tcacctttaa caaggacggc   1260

ttcagagact tccccgccat ggtgcaagaa ctgcatcaag gcggcagacg gtacatgatg   1320

atcgtggatc ctgccatctc ttctagcggc cctgccggaa gctacagacc ttatgatgag   1380

ggcctgagaa gaggcgtgtt catcaccaat gagacaggcc agcctctgat cggcaaagtg   1440

tggcctggaa gcaccgcctt tccagacttc accaatccaa ccgctctggc ttggtgggaa   1500

gatatggtgg ccgagttcca cgatcaggtg cccttcgatg gcatgtggat cgacatgaac   1560

gagcccagca acttcatcag ggcagcgag gatggctgcc ccaacaacga actggaaaat    1620
```

```
cctccttacg tgccaggcgt tgtcggagga acactgcagg ccgccacaat ttgtgccagc   1680
agccatcagt ttctgagcac ccactacaac ctgcacaacc tgtacggcct gaccgaggcc   1740
attgcctctc atagagccct ggttaaggcc agaggcaccc ggccttttgt gatcagcaga   1800
agcacatttg ccggccacgg cagatatgcc ggacattgga caggggacgt ttggtctagt   1860
tgggagcagc tggcctctag cgtgcccgag atcctgcagt ttaatctgct gggagtgccc   1920
ctcgtgggag ccgatgtttg tggatttctg ggcaacacct ccgaggaact gtgcgtcaga   1980
tggacacagc tgggcgcctt ctatcccttc atgagaaacc acaacagcct gctgagcctg   2040
cctcaagagc cttacagctt tagcgaaccc gcacagcagg ccatgagaaa ggccctgact   2100
ctgagatacg ctctgctgcc ccacctgtac accctgtttc atcaagctca tgtggccggc   2160
gagacagtgg ccagaccact gtttctggaa ttccccaagg acagcagcac ctggacagtg   2220
gatcatcagc tgctctgggg agaagccctg ctcattacac ctgtgctgca ggctggcaag   2280
gccgaagtga caggatactt tcccctcggc acttggtacg acctgcagac agttcctgtg   2340
gaagctctgg gatctctgcc tccacctcct gctgctccta gagagcctgc cattcactct   2400
gaaggccagt gggttacact gcccgctcca ctggacacca tcaatgtgca cctgagagcc   2460
ggctacatca tccctctgca aggccctgga ctgaccacaa ccgaaagcag acagcagcca   2520
atggctctgg ccgtggctct gacaaaaggc ggagaagcta gaggcgaact gttctgggat   2580
gacggcgaga gcctggaagt gctggaacgg ggagcctaca cacaagtgat ctttctcgcc   2640
cggaacaaca ccatcgtgaa cgaactcgtc agagtgacca gtgaaggtgc cggactgcag   2700
ctccagaaag tgacagtgct tggagtggcc acagcacccc agcaggtttt gtctaatggc   2760
gtgcccgtgt ccaacttcac atacagccct gacaccaagg tgctggacat ctgtgtgtct   2820
ctgctgatgg gcgagcagtt cctggtgtcc tggtgttga                          2859
```

<210> SEQ ID NO 7
<211> LENGTH: 92
<212> TYPE: DNA
<213> ORGANISM: Artificial Sequence
<220> FEATURE:
<223> OTHER INFORMATION: MVM intron

<400> SEQUENCE: 7

```
aagaggtaag ggtttaaggg atggttggtt ggtggggtat taatgtttaa ttacctggag     60
cacctgcctg aaatcacttt ttttcaggtt gg                                    92
```

<210> SEQ ID NO 8
<211> LENGTH: 49
<212> TYPE: DNA
<213> ORGANISM: Artificial Sequence
<220> FEATURE:
<223> OTHER INFORMATION: synthetic Polyadenylation signal

<400> SEQUENCE: 8

```
aataaaagat ctttattttc attagatctg tgtgttggtt ttttgtgtg                  49
```

<210> SEQ ID NO 9
<211> LENGTH: 7173
<212> TYPE: DNA
<213> ORGANISM: Artificial Sequence
<220> FEATURE:
<223> OTHER INFORMATION: plasmid AAVss-Dph-CRE02-CSkSH1-SPc5-12-MVM-
hGAAco-SynthpA

<400> SEQUENCE: 9

-continued

```
acatgtcctg caggcagctg cgcgctcgct cgctcactga ggccgcccgg gcaaagcccg     60
ggcgtcgggc gacctttggt cgcccggcct cagtgagcga gcgagcgcgc agagagggag    120
tggccaactc catcactagg ggttcctgcg gccgcacgcg taccggtgac aggtgcggtt    180
cccggagcgc aggcgcacac atgcacccac cggcgaacgc ggtgaccctc gccccacccc    240
atcccctccg gcgggcaact gggtcgggtc aggaggggca aacccgctag ggagacactc    300
catatacggc ccggcccgcg ttacctggga ccgggccaac ccgctccttc tttggtcaac    360
gcaggggacc cgggcggggg cccaggccgc gaaccggccg agggaggggg ctctagtgcc    420
caacacccaa atatggctcg agaagggcag cgacattcct gcggggtggc gcggagggaa    480
tgcccgcggg ctatataaaa cctgagcaga gggacaagcg gccaccgcag cggacagcgc    540
caagtgaagc ctcgcttccc ctccgcggcg accagggccc gagccgagag tagcagttgt    600
agctacccgc ccaggtaggg gcgcgccacg cgtgttctcc tctataaata cccgctctgg    660
tatttggggt tggcagctgt tgctgccagg gagatggttg ggttgacatg cggctcctga    720
caaaacacaa accccctggtg tgtgtgggcg tgggtggtgt gagtaggggg atgaatcagg    780
gagggggcgg gggacccagg gggcaggagc cacacaaagt ctgtgcgggg gtgggagcgc    840
acatagcaat tggaaactga aagcttatca gaccctttct ggaaatcagc ccactgttta    900
taaacttgag gccccaccct cgacagtacc ggggaggaag agggcctgca ctagtccaga    960
gggaaactga ggctcagggc tagctcgccc atagacatac atggcaggca ggctggtacc   1020
caacccgtta cgtggccacc gccttcggca ccatcctcac gacacccaaa tatggcgacg   1080
ggtgaggaat ggtggggagt tatttttaga gcggtgagga aggtgggcag gcagcaggtg   1140
ttggcgctct aaaaataact cccgggagtt atttttagag cggaggaatg gtggacaccc   1200
aaatatggcg acggttcctc acccgtcgcc atatttgggt gtccgccctc ggccggggcc   1260
gcattcctgg gggccgggcg gtgctcccgc ccgcctcgat aaaaggctcc ggggccggcg   1320
gcggcccacg agctacccgg aggagcggga ggcgccaagc tctagatcta gaactagtaa   1380
gaggtaaggg tttaagggat ggttggttgg tggggtatta atgtttaatt acctggagca   1440
cctgcctgaa atcacttttt ttcaggttgg cgtacggcca ccatgggcgt cagacatcct   1500
ccatgttctc acagactgct ggccgtgtgt gctctggtgt ctcttgctac agctgccctg   1560
ctgggacata tcctgctgca cgattttctg ctggtgccca gagagctgtc tggcagctct   1620
cctgtgctgg aagaaacaca ccctgcacat cagcagggcg cctctagacc tggacctaga   1680
gatgctcaag cccatcctgg cagacctaga gccgtgccta cacagtgtga cgtgccacct   1740
aacagcagat tcgactgcgc ccctgacaag gccatcacac aagagcagtg tgaagccaga   1800
ggctgctgct acattcctgc caaacaagga ctgcagggcg ctcagatggg acagccttgg   1860
tgcttcttcc caccatctta ccccagctac aagctggaaa acctgagcag cagcgagatg   1920
ggctacaccg ccacactgac cagaaccaca cctacattct tcccaaagga catcctgaca   1980
ctgcggctgg acgtgatgat ggaaaccgag aaccggctgc acttcaccat caaggacccc   2040
gccaatagaa gatacgaggt gcccctggaa acccctcacg tgcactctag agccccatct   2100
ccactgtaca gcgtggaatt cagcgaggaa cccctttggcg tgatcgtgcg gagacagctg   2160
gatggcagag tgctgctgaa taccacagtg gcccctctgt tcttcgccga ccagtttctg   2220
cagctgagca caagcctgcc tagccagtat atcacaggcc tggccgaaca cctgtctcca   2280
ctgatgctga gcaccagctg gaccagaatc accctgtgga acagagatct ggcccctaca   2340
cctggcgcca atctgtacgg ctctcaccct ttttatctgg ccctggaaga tggcggaagc   2400
```

```
gcccacggtg tctttctgct gaacagcaac gccatggacg tggtgctgca accatctcct   2460
gctctgtctt ggagaagcac cggcggcatc ctggacgtgt acatctttct gggacccgag   2520
cctaagagcg tggtgcagca gtatctggat gtcgtgggct acccccttcat gcctccttat   2580
tggggcctgg gcttccacct gtgtagatgg ggatacagct ccaccgccat caccagacag   2640
gtggtggaaa acatgacccg ggctcacttc ccactggatg tgcagtggaa cgacctggac   2700
tacatggact ccagacggga cttcaccttt aacaaggacg gcttcagaga cttccccgcc   2760
atggtgcaag aactgcatca aggcggcaga cggtacatga tgatcgtgga tcctgccatc   2820
tcttctagcg gccctgccgg aagctacaga ccttatgatg agggcctgag aagaggcgtg   2880
ttcatcacca atgagacagg ccagcctctg atcggcaaag tgtggcctgg aagcaccgcc   2940
tttccagact tcaccaatcc aaccgctctg gcttggtggg aagatatggt ggccgagttc   3000
cacgatcagg tgcccttcga tggcatgtgg atcgacatga acgagcccag caacttcatc   3060
aggggcagcg aggatggctg ccccaacaac gaactggaaa atcctcctta cgtgccaggc   3120
gttgtcggag gaacactgca ggccgccaca atttgtgcca gcagccatca gtttctgagc   3180
acccactaca acctgcacaa cctgtacggc ctgaccgagg ccattgcctc tcatagagcc   3240
ctggttaagg ccagaggcac ccggcctttt gtgatcagca gaagcacatt tgccggccac   3300
ggcagatatg ccggacattg gacaggggac gtttggtcta gttgggagca gctggcctct   3360
agcgtgcccg agatcctgca gtttaatctg ctgggagtgc ccctcgtggg agccgatgtt   3420
tgtggatttc tgggcaacac ctccgaggaa ctgtgcgtca gatggacaca gctgggcgcc   3480
ttctatccct tcatgagaaa ccacaacagc ctgctgagcc tgcctcaaga gccttacagc   3540
tttagcgaac ccgcacagca ggccatgaga aaggccctga ctctgagata cgctctgctg   3600
ccccacctgt acaccctgtt tcatcaagct catgtggccg gcgagacagt ggccagacca   3660
ctgtttctgg aattccccaa ggacagcagc acctggacag tggatcatca gctgctctgg   3720
ggagaagccc tgctcattac acctgtgctg caggctggca aggccgaagt gacaggatac   3780
tttcccctcg gcacttggta cgacctgcag acagttcctg tggaagctct gggatctctg   3840
cctccacctc ctgctgctcc tagagagcct gccattcact ctgaaggcca gtgggttaca   3900
ctgcccgctc cactggacac catcaatgtg cacctgagag ccggctacat catccctctg   3960
caaggccctg gactgaccac aaccgaaagc agacagcagc caatggctct ggccgtggct   4020
ctgacaaaag gcggagaagc tagaggcgaa ctgttctggg atgacggcga gagcctggaa   4080
gtgctggaac ggggagccta cacacaagtg atctttctcg cccggaacaa caccatcgtg   4140
aacgaactcg tcagagtgac cagtgaaggt gccggactgc agctccagaa agtgacagtg   4200
cttggagtgg ccacagcacc ccagcaggtt ttgtctaatg gcgtgcccgt gtccaacttc   4260
acatacagcc ctgacaccaa ggtgctggac atctgtgtgt ctctgctgat gggcgagcag   4320
ttcctggtgt cctggtgttg acctaggaat aaaagatctt tattttcatt agatctgtgt   4380
gttggttttt tgtgtgaccc gtctgatttt gtaggtaacc acgtgcggac cgagcggccg   4440
caggaacccc tagtgatgga gttggccact ccctctctgc gcgctcgctc gctcactgag   4500
gccgggcgac caaaggtcgc ccgacgcccg ggctttgccc gggcggcctc agtgagcgag   4560
cgagcgcgca gctgcctgca ggggcgcctg atgcggtatt ttctccttac gcatctgtgc   4620
ggtatttcac accgcatacg tcaaagcaac catagtacgc gccctgtagc ggcgcattaa   4680
gcgcggcggg tgtggtggtt acgcgcagcg tgaccgctac acttgccagc gccctagcgc   4740
```

-continued

```
ccgctccttt cgctttcttc ccttcctttc tcgccacgtt cgccggcttt ccccgtcaag   4800
ctctaaatcg ggggctccct ttagggttcc gatttagtgc tttacggcac ctcgacccca   4860
aaaaacttga tttgggtgat ggttcacgta gtgggccatc gccctgatag acggtttttc   4920
gccctttgac gttggagtcc acgttcttta atagtggact cttgttccaa actggaacaa   4980
cactcaaccc tatctcgggc tattcttttg atttataagg gattttgccg atttcggcct   5040
attggttaaa aaatgagctg atttaacaaa aatttaacgc gaattttaac aaaatattaa   5100
cgtttacaat tttatggtgc actctcagta caatctgctc tgatgccgca tagttaagcc   5160
agccccgaca cccgccaaca cccgctgacg cgccctgacg ggcttgtctg ctcccggcat   5220
ccgcttacag acaagctgtg accgtctccg ggagctgcat gtgtcagagg ttttcaccgt   5280
catcaccgaa acgcgcgaga cgaaagggcc tcgtgatacg cctattttta taggttaatg   5340
tcatgataat aatggtttct tagacgtcag gtggcacttt tcggggaaat gtgcgcggaa   5400
cccctatttg tttatttttc taaatacatt caaatatgta tccgctcatg agacaataac   5460
cctgataaat gcttcaataa tattgaaaaa ggaagagtat gagtattcaa catttccgtg   5520
tcgcccttat tccctttttt gcggcatttt gccttcctgt ttttgctcac ccagaaacgc   5580
tggtgaaagt aaaagatgct gaagatcagt tgggtgcacg agtgggttac atcgaactgg   5640
atctcaacag cggtaagatc cttgagagtt ttcgccccga agaacgtttt ccaatgatga   5700
gcacttttaa agttctgcta tgtggcgcgg tattatcccg tattgacgcc gggcaagagc   5760
aactcggtcg ccgcatacac tattctcaga atgacttggt tgagtactca ccagtcacag   5820
aaaagcatct tacggatggc atgacagtaa gagaattatg cagtgctgcc ataaccatga   5880
gtgataacac tgcggccaac ttacttctga caacgatcgg aggaccgaag gagctaaccg   5940
cttttttgca caacatgggg gatcatgtaa ctcgccttga tcgttgggaa ccggagctga   6000
atgaagccat accaaacgac gagcgtgaca ccacgatgcc tgtagcaatg gcaacaacgt   6060
tgcgcaaact attaactggc gaactactta ctctagcttc ccggcaacaa ttaatagact   6120
ggatggaggc ggataaagtt gcaggaccac ttctgcgctc ggcccttccg gctggctggt   6180
ttattgctga taaatctgga gccggtgagc gtgggtctcg cggtatcatt gcagcactgg   6240
ggccagatgg taagccctcc cgtatcgtag ttatctacac gacggggagt caggcaacta   6300
tggatgaacg aaatagacag atcgctgaga taggtgcctc actgattaag cattggtaac   6360
tgtcagacca agtttactca tatatacttt agattgattt aaaacttcat ttttaattta   6420
aaaggatcta ggtgaagatc ctttttgata atctcatgac caaaatccct taacgtgagt   6480
tttcgttcca ctgagcgtca gaccccgtag aaaagatcaa aggatcttct tgagatcctt   6540
tttttctgcg cgtaatctgc tgcttgcaaa caaaaaaacc accgctacca gcggtggttt   6600
gtttgccgga tcaagagcta ccaactcttt ttccgaaggt aactggcttc agcagagcgc   6660
agataccaaa tactgtcctt ctagtgtagc cgtagttagg ccaccacttc aagaactctg   6720
tagcaccgcc tacatacctc gctctgctaa tcctgttacc agtggctgct gccagtggcg   6780
ataagtcgtg tcttaccggg ttggactcaa gacgatagtt accggataag gcgcagcggt   6840
cgggctgaac ggggggttcg tgcacacagc ccagcttgga gcgaacgacc tacaccgaac   6900
tgagatacct acagcgtgag ctatgagaaa gcgccacgct tcccgaaggg agaaaggcgg   6960
acaggtatcc ggtaagcggc agggtcggaa caggagagcg cacgagggag cttccagggg   7020
gaaacgcctg gtatctttat agtcctgtcg ggtttcgcca cctctgactt gagcgtcgat   7080
ttttgtgatg ctcgtcaggg gggcggagcc tatggaaaaa cgccagcaac gcggcctttt   7140
```

tacggttcct ggccttttgc tggccttttg ctc 7173

<210> SEQ ID NO 10
<211> LENGTH: 6324
<212> TYPE: DNA
<213> ORGANISM: Artificial Sequence
<220> FEATURE:
<223> OTHER INFORMATION: plasmid AAVss-SPc5-12-MVM-hGAAco-SynthpA

<400> SEQUENCE: 10
acatgtcctg caggcagctg cgcgctcgct cgctcactga ggccgcccgg gcaaagcccg 60
ggcgtcgggc gacctttggt cgcccggcct cagtgagcga gcgagcgcgc agagagggag 120
tggccaactc catcactagg ggttcctgcg gccgcacgcg taccgggtac ccaacccgtt 180
acgtggccac cgccttcggc accatcctca cgacacccaa atatggcgac gggtgaggaa 240
tggtggggag ttatttttag agcggtgagg aaggtgggca ggcagcaggt gttggcgctc 300
taaaaataac tcccgggagt tatttttaga gcggaggaat ggtggacacc caaatatggc 360
gacggttcct cacccgtcgc catatttggg tgtccgccct cggccggggc cgcattcctg 420
ggggccgggc ggtgctcccg cccgcctcga taaaaggctc cggggccggc ggcggcccac 480
gagctacccg gaggagcggg aggcgccaag ctctagatct agaactagta agaggtaagg 540
gtttaaggga tggttggttg gtggggtatt aatgtttaat tacctggagc acctgcctga 600
aatcactttt tttcaggttg gcgtacggcc accatgggcg tcagacatcc tccatgttct 660
cacagactgc tggccgtgtg tgctctggtg tctcttgcta cagctgccct gctgggacat 720
atcctgctgc acgatttttct gctggtgccc agagagctgt ctggcagctc tcctgtgctg 780
gaagaaacac accctgcaca tcagcagggc gcctctagac ctggacctag agatgctcaa 840
gcccatcctg gcagacctag agccgtgcct acacagtgtg acgtgccacc taacagcaga 900
ttcgactgcg cccctgacaa ggccatcaca caagagcagt gtgaagccag aggctgctgc 960
tacattcctg ccaaacaagg actgcagggc gctcagatgg gacagccttg gtgcttcttc 1020
ccaccatctt accccagcta caagctggaa aacctgagca gcagcgagat gggctacacc 1080
gccacactga ccagaaccac acctacattc ttcccaaagg acatcctgac actgcggctg 1140
gacgtgatga tggaaaccga gaaccggctg cacttcacca tcaaggaccc cgccaataga 1200
agatacgagg tgcccctgga aacccctcac gtgcactcta gagccccatc tccactgtac 1260
agcgtggaat tcagcgagga accctttggc gtgatcgtgc ggagacagct ggatggcaga 1320
gtgctgctga ataccacagt ggcccctctg ttcttcgccg accagtttct gcagctgagc 1380
acaagcctgc ctagccagta tatcacaggc ctggccgaac acctgtctcc actgatgctg 1440
agcaccagct ggaccagaat caccctgtgg aacagagatc tggcccctac acctggcgcc 1500
aatctgtacg gctctcaccc tttttatctg gccctggaag atggcggaag cgcccacggt 1560
gtctttctgc tgaacagcaa cgccatggac gtggtgctgc aaccatctcc tgctctgtct 1620
tggagaagca ccggcggcat cctggacgtg tacatctttc tgggacccga gcctaagagc 1680
gtggtgcagc agtatctgga tgtcgtgggc taccccttca tgcctcctta ttggggcctg 1740
ggcttccacc tgtgtagatg gggatacagc tccaccgcca tcaccagaca ggtggtggaa 1800
aacatgaccc gggctcactt cccactggat gtgcagtgga acgacctgga ctacatggac 1860
tccagacggg acttcacctt taacaaggac ggcttcagag acttccccgc catggtgcaa 1920
gaactgcatc aaggcggcag acggtacatg atgatcgtgg atcctgccat ctcttctagc 1980

-continued

```
ggccctgccg gaagctacag accttatgat gagggcctga gaagaggcgt gttcatcacc   2040
aatgagacag gccagcctct gatcggcaaa gtgtggcctg gaagcaccgc ctttccagac   2100
ttcaccaatc caaccgctct ggcttggtgg gaagatatgg tggccgagtt ccacgatcag   2160
gtgcccttcg atggcatgtg gatcgacatg aacgagccca gcaacttcat caggggcagc   2220
gaggatggct gccccaacaa cgaactggaa aatcctcctt acgtgccagg cgttgtcgga   2280
ggaacactgc aggccgccac aatttgtgcc agcagccatc agtttctgag cacccactac   2340
aacctgcaca acctgtacgg cctgaccgag gccattgcct ctcatagagc cctggttaag   2400
gccagaggca cccggccttt tgtgatcagc agaagcacat ttgccggcca cggcagatat   2460
gccggacatt ggacagggga cgtttggtct agttgggagc agctggcctc tagcgtgccc   2520
gagatcctgc agtttaatct gctgggagtg cccctcgtgg gagccgatgt ttgtggattt   2580
ctgggcaaca cctccgagga actgtgcgtc agatggacac agctgggcgc cttctatccc   2640
ttcatgagaa accacaacag cctgctgagc ctgcctcaag agccttacag ctttagcgaa   2700
cccgcacagc aggccatgag aaaggccctg actctgagat acgctctgct gccccacctg   2760
tacaccctgt ttcatcaagc tcatgtggcc ggcgagacag tggccagacc actgtttctg   2820
gaattcccca aggacagcag cacctggaca gtggatcatc agctgctctg ggagaagcc   2880
ctgctcatta cacctgtgct gcaggctggc aaggccgaag tgacaggata ctttcccctc   2940
ggcacttggt acgacctgca gacagttcct gtggaagctc tgggatctct gcctccacct   3000
cctgctgctc ctagagagcc tgccattcac tctgaaggcc agtgggttac actgcccgct   3060
ccactggaca ccatcaatgt gcacctgaga gccggctaca tcatccctct gcaaggccct   3120
ggactgacca caaccgaaag cagacagcag ccaatggctc tggccgtggc tctgacaaaa   3180
ggcggagaag ctagaggcga actgttctgg gatgacggcg agagcctgga agtgctggaa   3240
cggggagcct acacacaagt gatctttctc gcccggaaca acaccatcgt gaacgaactc   3300
gtcagagtga ccagtgaagg tgccggactg cagctccaga aagtgacagt gcttggagtg   3360
gccacagcac cccagcaggt tttgtctaat ggcgtgcccg tgtccaactt cacatacagc   3420
cctgacacca aggtgctgga catctgtgtg tctctgctga tgggcgagca gttcctggtg   3480
tcctggtgtt gacctaggaa taaaagatct ttattttcat tagatctgtg tgttggtttt   3540
ttgtgtgacc cgtctgattt tgtaggtaac cacgtgcgga ccgagcggcc gcaggaaccc   3600
ctagtgatgg agttggccac tccctctctg cgcgctcgct cgctcactga ggccgggcga   3660
ccaaaggtcg cccgacgccc gggctttgcc cgggcggcct cagtgagcga gcgagcgcgc   3720
agctgcctgc aggggcgcct gatgcggtat tttctcctta cgcatctgtg cggtatttca   3780
caccgcatac gtcaaagcaa ccatagtacg cgccctgtag cggcgcatta agcgcggcgg   3840
gtgtggtggt tacgcgcagc gtgaccgcta cacttgccag cgccctagcg cccgctcctt   3900
tcgctttctt cccttccttt ctcgccacgt tcgccggctt tccccgtcaa gctctaaatc   3960
gggggctccc tttagggttc cgatttagtg ctttacggca cctcgacccc aaaaaacttg   4020
atttgggtga tggttcacgt agtgggccat cgccctgata gacggttttt cgccctttga   4080
cgttggagtc cacgttcttt aatagtggac tcttgttcca aactggaaca acactcaacc   4140
ctatctcggg ctattctttt gatttataag ggattttgcc gatttcggcc tattggttaa   4200
aaaatgagct gatttaacaa aaatttaacg cgaattttaa caaaatatta acgtttacaa   4260
ttttatggtg cactctcagt acaatctgct ctgatgccgc atagttaagc cagccccgac   4320
acccgccaac acccgctgac gcgccctgac gggcttgtct gctcccggca tccgcttaca   4380
```

```
gacaagctgt gaccgtctcc gggagctgca tgtgtcagag gttttcaccg tcatcaccga   4440

aacgcgcgag acgaaagggc ctcgtgatac gcctattttt ataggttaat gtcatgataa   4500

taatggtttc ttagacgtca ggtggcactt ttcggggaaa tgtgcgcgga acccctattt   4560

gtttattttt ctaaatacat tcaaatatgt atccgctcat gagacaataa ccctgataaa   4620

tgcttcaata atattgaaaa aggaagagta tgagtattca acatttccgt gtcgccctta   4680

ttcccttttt tgcggcattt tgccttcctg tttttgctca cccagaaacg ctggtgaaag   4740

taaaagatgc tgaagatcag ttgggtgcac gagtgggtta catcgaactg gatctcaaca   4800

gcggtaagat ccttgagagt tttcgccccg aagaacgttt tccaatgatg agcactttta   4860

aagttctgct atgtggcgcg gtattatccc gtattgacgc cgggcaagag caactcggtc   4920

gccgcataca ctattctcag aatgacttgg ttgagtactc accagtcaca gaaaagcatc   4980

ttacggatgg catgacagta agagaattat gcagtgctgc cataaccatg agtgataaca   5040

ctgcggccaa cttacttctg acaacgatcg gaggaccgaa ggagctaacc gcttttttgc   5100

acaacatggg ggatcatgta actcgccttg atcgttggga accggagctg aatgaagcca   5160

taccaaacga cgagcgtgac accacgatgc ctgtagcaat ggcaacaacg ttgcgcaaac   5220

tattaactgg cgaactactt actctagctt cccggcaaca attaatagac tggatggagg   5280

cggataaagt tgcaggacca cttctgcgct cggcccttcc ggctggctgg tttattgctg   5340

ataaatctgg agccggtgag cgtgggtctc gcggtatcat tgcagcactg gggccagatg   5400

gtaagccctc ccgtatcgta gttatctaca cgacggggag tcaggcaact atggatgaac   5460

gaaatagaca gatcgctgag ataggtgcct cactgattaa gcattggtaa ctgtcagacc   5520

aagtttactc atatatactt tagattgatt taaaacttca tttttaattt aaaaggatct   5580

aggtgaagat cctttttgat aatctcatga ccaaaatccc ttaacgtgag ttttcgttcc   5640

actgagcgtc agaccccgta gaaaagatca aaggatcttc ttgagatcct ttttttctgc   5700

gcgtaatctg ctgcttgcaa acaaaaaaac caccgctacc agcggtggtt tgtttgccgg   5760

atcaagagct accaactctt tttccgaagg taactggctt cagcagagcg cagataccaa   5820

atactgtcct tctagtgtag ccgtagttag gccaccactt caagaactct gtagcaccgc   5880

ctacatacct cgctctgcta atcctgttac cagtggctgc tgccagtggc gataagtcgt   5940

gtcttaccgg gttggactca agacgatagt taccggataa ggcgcagcgg tcgggctgaa   6000

cggggggttc gtgcacacag cccagcttgg agcgaacgac ctacaccgaa ctgagatacc   6060

tacagcgtga gctatgagaa agcgccacgc ttcccgaagg gagaaaggcg gacaggtatc   6120

cggtaagcgg cagggtcgga acaggagagc gcacgaggga gcttccaggg ggaaacgcct   6180

ggtatcttta tagtcctgtc gggtttcgcc acctctgact tgagcgtcga tttttgtgat   6240

gctcgtcagg ggggcggagc ctatggaaaa acgccagcaa cgcggccttt ttacggttcc   6300

tggccttttg ctggcctttt gctc                                          6324
```

```
<210> SEQ ID NO 11
<211> LENGTH: 7173
<212> TYPE: DNA
<213> ORGANISM: Artificial Sequence
<220> FEATURE:
<223> OTHER INFORMATION: plasmid AAVss-Dph-CRE02-CSkSH1-SPc5-12-MVM-
      hGAAwt-SynthpA

<400> SEQUENCE: 11

acatgtcctg caggcagctg cgcgctcgct cgctcactga ggccgcccgg gcaaagcccg     60
```

```
ggcgtcgggc gacctttggt cgcccggcct cagtgagcga gcgagcgcgc agagagggag    120
tggccaactc catcactagg ggttcctgcg gccgcacgcg taccggtgac aggtgcggtt    180
cccggagcgc aggcgcacac atgcacccac cggcgaacgc ggtgaccctc gccccacccc    240
atcccctccg gcgggcaact gggtcgggtc aggaggggca aacccgctag ggagacactc    300
catatacggc ccggcccgcg ttacctggga ccgggccaac ccgctccttc tttggtcaac    360
gcaggggacc cgggcggggg cccaggccgc gaaccggccg agggaggggg ctctagtgcc    420
caacacccaa atatggctcg agaagggcag cgacattcct gcggggtggc gcggagggaa    480
tgcccgcggg ctatataaaa cctgagcaga gggacaagcg gccaccgcag cggacagcgc    540
caagtgaagc ctcgcttccc ctccgcggcg accagggccc gagccgagag tagcagttgt    600
agctacccgc ccaggtaggg gcgcgccacg cgtgttctcc tctataaata cccgctctgg    660
tatttggggt tggcagctgt tgctgccagg gagatggttg ggttgacatg cggctcctga    720
caaaacacaa acccctggtg tgtgtgggcg tgggtggtgt gagtaggggg atgaatcagg    780
gagggggcgg gggacccagg gggcaggagc cacacaaagt ctgtgcgggg gtgggagcgc    840
acatagcaat tggaaactga aagcttatca gaccctttct ggaaatcagc ccactgttta    900
taaacttgag gccccaccct cgacagtacc ggggaggaag agggcctgca ctagtccaga    960
gggaaactga ggctcagggc tagctcgccc atagacatac atggcaggca ggctggtacc   1020
caacccgtta cgtggccacc gccttcggca ccatcctcac gacacccaaa tatggcgacg   1080
ggtgaggaat ggtggggagt tatttttaga gcggtgagga aggtgggcag gcagcaggtg   1140
ttggcgctct aaaaataact cccgggagtt atttttagag cggaggaatg gtggacaccc   1200
aaatatggcg acggttcctc acccgtcgcc atatttgggt gtccgccctc ggccggggcc   1260
gcattcctgg gggccgggcg gtgctcccgc ccgcctcgat aaaaggctcc ggggccggcg   1320
gcggcccacg agctacccgg aggagcggga ggcgccaagc tctagatcta gaactagtaa   1380
gaggtaaggg tttaagggat ggttggttgg tggggtatta atgtttaatt acctggagca   1440
cctgcctgaa atcacttttt ttcaggttgg cgtacggcca ccatgggagt gaggcacccg   1500
ccctgctccc accggctcct ggccgtctgc gccctcgtgt ccttggcaac cgctgcactc   1560
ctggggcaca tcctactcca tgatttcctg ctggttcccc gagagctgag tggctcctcc   1620
ccagtcctgg aggagactca cccagctcac cagcagggag ccagcagacc agggccccgg   1680
gatgcccagg cacaccccgg ccgtcccaga gcagtgccca cacagtgcga cgtccccccc   1740
aacagccgct tcgattgcgc ccctgacaag gccatcaccc aggaacagtg cgaggcccgc   1800
ggctgttgct acatccctgc aaagcagggg ctgcagggag cccagatggg gcagccctgg   1860
tgcttcttcc cacccagcta ccccagctac aagctggaga acctgagctc ctctgaaatg   1920
ggctacacgg ccaccctgac ccgtaccacc cccaccttct tccccaagga catcctgacc   1980
ctgcggctgg acgtgatgat ggagactgag aaccgcctcc acttcacgat caaagatcca   2040
gctaacaggc gctacgaggt gcccttggag accccgcatg tccacagccg ggcaccgtcc   2100
ccactctaca gcgtggagtt ctccgaggag cccttcgggg tgatcgtgcg ccggcagctg   2160
gacggccgcg tgctgctgaa cacgacggtg gcgcccctgt tctttgcgga ccagttcctt   2220
cagctgtcca cctcgctgcc ctcgcagtat atcacaggcc tcgccgagca cctcagtccc   2280
ctgatgctca gcaccagctg gaccaggatc accctgtgga accgggacct tgcgcccacg   2340
cccggtgcga acctctacgg gtctcaccct ttctacctgg cgctggagga cggcgggtcg   2400
```

-continued

```
gcacacgggg tgttcctgct aaacagcaat gccatggatg tggtcctgca gccgagccct   2460
gcccttagct ggaggtcgac aggtgggatc ctggatgtct acatcttcct gggcccagag   2520
cccaagagcg tggtgcagca gtacctggac gttgtgggat acccgttcat gccgccatac   2580
tggggcctgg gcttccacct gtgccgctgg ggctactcct ccaccgctat cacccgccag   2640
gtggtggaga acatgaccag ggcccacttc cccctggacg tccagtggaa cgacctggac   2700
tacatggact cccggaggga cttcacgttc aacaaggatg gcttccggga cttcccggcc   2760
atggtgcagg agctgcacca gggcggccgg cgctacatga tgatcgtgga tcctgccatc   2820
agcagctcgg gccctgccgg gagctacagg ccctacgacg agggtctgcg gagggggtt    2880
ttcatcacca acgagaccgg ccagccgctg attgggaagg tatggcccgg gtccactgcc   2940
ttccccgact tcaccaaccc cacagccctg gcctggtggg aggacatggt ggctgagttc   3000
catgaccagg tgcccttcga cggcatgtgg attgacatga acgagccttc caacttcatc   3060
aggggctctg aggacggctg ccccaacaat gagctggaga acccacccta cgtgcctggg   3120
gtggttgggg ggaccctcca ggcggccacc atctgtgcct ccagccacca gtttctctcc   3180
acacactaca acctgcacaa cctctacggc ctgaccgaag ccatcgcctc ccacagggcg   3240
ctggtgaagg ctcgggggac acgcccattt gtgatctccc gctcgacctt tgctggccac   3300
ggccgatacg ccggccactg gacgggggac gtgtggagct cctgggagca gctcgcctcc   3360
tccgtgccag aaatcctgca gtttaacctg ctgggggtgc ctctggtcgg ggccgacgtc   3420
tgcggcttcc tgggcaacac ctcagaggag ctgtgtgtgc gctggaccca gctgggggcc   3480
ttctacccct tcatgcggaa ccacaacagc ctgctcagtc tgccccagga gccgtacagc   3540
ttcagcgagc cggcccagca ggccatgagg aaggccctca ccctgcgcta cgcactcctc   3600
ccccacctct acacactgtt ccaccaggcc cacgtcgcgg gggagaccgt ggcccggccc   3660
ctcttcctgg agttccccaa ggactctagc acctggactg tggaccacca gctcctgtgg   3720
ggggaggccc tgctcatcac cccagtgctc caggccggga aggccgaagt gactggctac   3780
ttccccttgg gcacatggta cgacctgcag acggtgccag tagaggccct tggcagcctc   3840
ccaccccac ctgcagctcc ccgtgagcca gccatccaca gcgaggggca gtgggtgacg    3900
ctgccggccc ccctggacac catcaacgtc cacctccggg ctgggtacat catcccctg    3960
cagggccctg gcctcacaac cacagagtcc cgccagcagc ccatggccct ggctgtggcc   4020
ctgaccaagg gtggggaggc ccgaggggag ctgttctggg acgatggaga gagcctggaa   4080
gtgctggagc gaggggccta cacacaggtc atcttcctgg ccaggaataa cacgatcgtg   4140
aatgagctgg tacgtgtgac cagtgaggga gctggcctgc agctgcagaa ggtgactgtc   4200
ctgggcgtgg ccacggcgcc ccagcaggtc ctctccaacg gtgtccctgt ctccaacttc   4260
acctacagcc ccgacaccaa ggtcctggac atctgtgtct cgctgttgat gggagagcag   4320
tttctcgtca gctggtgtta gcctaggaat aaaagatctt tattttcatt agatctgtgt   4380
gttggttttt tgtgtgaccc gtctgatttt gtaggtaacc acgtgcggac cgagcggccg   4440
caggaacccc tagtgatgga gttggccact ccctctctgc gcgctcgctc gctcactgag   4500
gccgggcgac caaaggtcgc ccgacgcccg ggctttgccc gggcggcctc agtgagcgag   4560
cgagcgcgca gctgcctgca ggggcgcctg atgcggtatt ttctccttac gcatctgtgc   4620
ggtatttcac accgcatacg tcaaagcaac catagtacgc gccctgtagc ggcgcattaa   4680
gcgcggcggg tgtggtggtt acgcgcagcg tgaccgctac acttgccagc gccctagcgc   4740
ccgctccttt cgctttcttc ccttcctttc tcgccacgtt cgccggcttt ccccgtcaag   4800
```

```
ctctaaatcg ggggctccct ttagggttcc gatttagtgc tttacggcac ctcgacccca   4860
aaaaacttga tttgggtgat ggttcacgta gtgggccatc gccctgatag acggtttttc   4920
gccctttgac gttggagtcc acgttcttta atagtggact cttgttccaa actggaacaa   4980
cactcaaccc tatctcgggc tattcttttg atttataagg gattttgccg atttcggcct   5040
attggttaaa aaatgagctg atttaacaaa aatttaacgc gaattttaac aaaatattaa   5100
cgtttacaat tttatggtgc actctcagta caatctgctc tgatgccgca tagttaagcc   5160
agccccgaca cccgccaaca cccgctgacg cgccctgacg ggcttgtctg ctcccggcat   5220
ccgcttacag acaagctgtg accgtctccg ggagctgcat gtgtcagagg ttttcaccgt   5280
catcaccgaa acgcgcgaga cgaaagggcc tcgtgatacg cctattttta taggttaatg   5340
tcatgataat aatggtttct tagacgtcag gtggcacttt tcggggaaat gtgcgcggaa   5400
cccctatttg tttatttttc taaatacatt caaatatgta tccgctcatg agacaataac   5460
cctgataaat gcttcaataa tattgaaaaa ggaagagtat gagtattcaa catttccgtg   5520
tcgcccttat tccctttttt gcggcatttt gccttcctgt ttttgctcac ccagaaacgc   5580
tggtgaaagt aaaagatgct gaagatcagt tgggtgcacg agtgggttac atcgaactgg   5640
atctcaacag cggtaagatc cttgagagtt ttcgccccga agaacgtttt ccaatgatga   5700
gcacttttaa agttctgcta tgtggcgcgg tattatcccg tattgacgcc gggcaagagc   5760
aactcggtcg ccgcatacac tattctcaga atgacttggt tgagtactca ccagtcacag   5820
aaaagcatct tacggatggc atgacagtaa gagaattatg cagtgctgcc ataaccatga   5880
gtgataacac tgcggccaac ttacttctga caacgatcgg aggaccgaag gagctaaccg   5940
cttttttgca caacatgggg gatcatgtaa ctcgccttga tcgttgggaa ccggagctga   6000
atgaagccat accaaacgac gagcgtgaca ccacgatgcc tgtagcaatg gcaacaacgt   6060
tgcgcaaact attaactggc gaactactta ctctagcttc ccggcaacaa ttaatagact   6120
ggatggaggc ggataaagtt gcaggaccac ttctgcgctc ggcccttccg gctggctggt   6180
ttattgctga taaatctgga gccggtgagc gtgggtctcg cggtatcatt gcagcactgg   6240
ggccagatgg taagccctcc cgtatcgtag ttatctacac gacggggagt caggcaacta   6300
tggatgaacg aaatagacag atcgctgaga taggtgcctc actgattaag cattggtaac   6360
tgtcagacca agtttactca tatatacttt agattgattt aaaacttcat ttttaattta   6420
aaaggatcta ggtgaagatc ctttttgata atctcatgac caaaatccct taacgtgagt   6480
tttcgttcca ctgagcgtca gaccccgtag aaaagatcaa aggatcttct tgagatcctt   6540
tttttctgcg cgtaatctgc tgcttgcaaa caaaaaaacc accgctacca gcggtggttt   6600
gtttgccgga tcaagagcta ccaactcttt ttccgaaggt aactggcttc agcagagcgc   6660
agataccaaa tactgtcctt ctagtgtagc cgtagttagg ccaccacttc aagaactctg   6720
tagcaccgcc tacatacctc gctctgctaa tcctgttacc agtggctgct gccagtggcg   6780
ataagtcgtg tcttaccggg ttggactcaa gacgatagtt accggataag gcgcagcggt   6840
cgggctgaac ggggggttcg tgcacacagc ccagcttgga gcgaacgacc tacaccgaac   6900
tgagatacct acagcgtgag ctatgagaaa gcgccacgct tcccgaaggg agaaaggcgg   6960
acaggtatcc ggtaagcggc agggtcggaa caggagagcg cacgagggag cttccagggg   7020
gaaacgcctg gtatctttat agtcctgtcg ggtttcgcca cctctgactt gagcgtcgat   7080
ttttgtgatg ctcgtcaggg gggcggagcc tatggaaaaa cgccagcaac gcggcctttt   7140
```

tacggttcct ggccttttgc tggccttttg ctc 7173

<210> SEQ ID NO 12
<211> LENGTH: 6308
<212> TYPE: DNA
<213> ORGANISM: Artificial Sequence
<220> FEATURE:
<223> OTHER INFORMATION: plasmid AAVss-SPc5-12-MVM-hGAAwt-SynthpA

<400> SEQUENCE: 12
acatgtcctg caggcagctg cgcgctcgct cgctcactga ggccgcccgg gcaaagcccg 60
ggcgtcgggc gacctttggt cgcccggcct cagtgagcga gcgagcgcgc agagagggag 120
tggccaactc catcactagg ggttcctgcg gccgcacgcg taccggttgg ccaccgcctt 180
cggcaccatc ctcacgacac ccaaatatgg cgacgggtga ggaatggtgg ggagttattt 240
ttagagcggt gaggaaggtg ggcaggcagc aggtgttggc gctctaaaaa taactcccgg 300
gagttatttt tagagcggag gaatggtgga cacccaaata tggcgacggt tcctcacccg 360
tcgccatatt tgggtgtccg ccctcggccg gggccgcatt cctgggggcc gggcggtgct 420
cccgcccgcc tcgataaaag gctccggggc cggcggcggc ccacgagcta cccggaggag 480
cgggaggcgc caagctctag atctagaact agtaagaggt aagggtttaa gggatggttg 540
gttggtgggg tattaatgtt taattacctg gagcacctgc ctgaaatcac ttttttttcag 600 gttggcgtac ggccaccatg ggagtgaggc acccgccctg ctcccaccgg ctcctggccg 660
tctgcgccct cgtgtccttg gcaaccgctg cactcctggg gcacatccta ctccatgatt 720
tcctgctggt tccccgagag ctgagtggct cctccccagt cctggaggag actcacccag 780
ctcaccagca gggagccagc agaccagggc cccgggatgc ccaggcacac cccggccgtc 840
ccagagcagt gcccacacag tgcgacgtcc cccccaacag ccgcttcgat tgcgcccctg 900
acaaggccat cacccaggaa cagtgcgagg cccgcggctg ttgctacatc cctgcaaagc 960
aggggctgca gggagcccag atggggcagc cctggtgctt cttcccaccc agctacccca 1020
gctacaagct ggagaacctg agctcctctg aaatgggcta cacggccacc ctgacccgta 1080
ccacccccac cttcttcccc aaggacatcc tgaccctgcg gctggacgtg atgatggaga 1140
ctgagaaccg cctccacttc acgatcaaag atccagctaa caggcgctac gaggtgccct 1200
tggagacccc gcatgtccac agccgggcac cgtccccact ctacagcgtg gagttctccg 1260
aggagccctt cggggtgatc gtgcgccggc agctggacgg ccgcgtgctg ctgaacacga 1320
cggtggcgcc cctgttcttt gcggaccagt tccttcagct gtccacctcg ctgccctcgc 1380
agtatatcac aggcctcgcc gagcacctca gtcccctgat gctcagcacc agctggacca 1440
ggatcaccct gtggaaccgg gaccttgcgc ccacgcccgg tgcgaacctc tacgggtctc 1500
accctttcta cctggcgctg gaggacggcg ggtcggcaca cggggtgttc ctgctaaaca 1560
gcaatgccat ggatgtggtc ctgcagccga gccctgccct tagctggagg tcgacaggtg 1620
ggatcctgga tgtctacatc ttcctgggcc cagagcccaa gagcgtggtg cagcagtacc 1680
tggacgttgt gggataccg ttcatgccgc catactgggg cctgggcttc cacctgtgcc 1740
gctggggcta ctcctccacc gctatcaccc gccaggtggt ggagaacatg accagggccc 1800
acttccccct ggacgtccag tggaacgacc tggactacat ggactcccgg agggacttca 1860
cgttcaacaa ggatggcttc cgggacttcc cggccatggt gcaggagctg caccagggcg 1920
gccggcgcta catgatgatc gtggatcctg ccatcagcag ctcgggccct gccgggagct 1980
acaggcccta cgacgagggt ctgcggaggg gggttttcat caccaacgag accggccagc 2040

```
cgctgattgg gaaggtatgg cccgggtcca ctgccttccc cgacttcacc aaccccacag   2100
ccctggcctg gtgggaggac atggtggctg agttccatga ccaggtgccc ttcgacggca   2160
tgtggattga catgaacgag ccttccaact tcatcagggg ctctgaggac ggctgcccca   2220
acaatgagct ggagaaccca ccctacgtgc ctggggtggt tggggggacc ctccaggcgg   2280
ccaccatctg tgcctccagc caccagtttc tctccacaca ctacaacctg cacaacctct   2340
acggcctgac cgaagccatc gcctcccaca gggcgctggt gaaggctcgg gggacacgcc   2400
catttgtgat ctcccgctcg acctttgctg gccacggccg atacgccggc cactggacgg   2460
gggacgtgtg gagctcctgg gagcagctcg cctcctccgt gccagaaatc ctgcagttta   2520
acctgctggg ggtgcctctg gtcggggccg acgtctgcgg cttcctgggc aacacctcag   2580
aggagctgtg tgtgcgctgg acccagctgg gggccttcta ccccttcatg cggaaccaca   2640
acagcctgct cagtctgccc caggagccgt acagcttcag cgagccggcc cagcaggcca   2700
tgaggaaggc cctcaccctg cgctacgcac tcctccccca cctctacaca ctgttccacc   2760
aggcccacgt cgcgggggag accgtggccc ggcccctctt cctggagttc cccaaggact   2820
ctagcacctg gactgtggac caccagctcc tgtgggggga ggccctgctc atcaccccag   2880
tgctccaggc cgggaaggcc gaagtgactg gctacttccc cttgggcaca tggtacgacc   2940
tgcagacggt gccagtagag gcccttggca gcctcccacc cccacctgca gctccccgtg   3000
agccagccat ccacagcgag gggcagtggg tgacgctgcc ggcccccctg gacaccatca   3060
acgtccacct ccgggctggg tacatcatcc ccctgcaggg ccctggcctc acaaccacag   3120
agtcccgcca gcagcccatg gccctggctg tggccctgac caagggtggg gaggcccgag   3180
gggagctgtt ctgggacgat ggagagagcc tggaagtgct ggagcgaggg gcctacacac   3240
aggtcatctt cctggccagg aataacacga tcgtgaatga gctggtacgt gtgaccagtg   3300
agggagctgg cctgcagctg cagaaggtga ctgtcctggg cgtggccacg gcgccccagc   3360
aggtcctctc caacggtgtc cctgtctcca acttcaccta cagccccgac accaaggtcc   3420
tggacatctg tgtctcgctg ttgatgggag agcagtttct cgtcagctgg tgttagccta   3480
ggaataaaag atctttattt tcattagatc tgtgtgttgg ttttttgtgt gacccgtctg   3540
attttgtagg taaccacgtg cggaccgagc ggccgcagga acccctagtg atggagttgg   3600
ccactccctc tctgcgcgct cgctcgctca ctgaggccgg gcgaccaaag gtcgcccgac   3660
gcccgggctt tgcccgggcg gcctcagtga gcgagcgagc gcgcagctgc ctgcaggggc   3720
gcctgatgcg gtattttctc cttacgcatc tgtgcggtat ttcacaccgc atacgtcaaa   3780
gcaaccatag tacgcgccct gtagcggcgc attaagcgcg gcgggtgtgg tggttacgcg   3840
cagcgtgacc gctacacttg ccagcgccct agcgcccgct cctttcgctt tcttcccttc   3900
ctttctcgcc acgttcgccg gctttccccg tcaagctcta aatcgggggc tccctttagg   3960
gttccgattt agtgctttac ggcacctcga ccccaaaaaa cttgatttgg gtgatggttc   4020
acgtagtggg ccatcgccct gatagacggt ttttcgccct ttgacgttgg agtccacgtt   4080
ctttaatagt ggactcttgt tccaaactgg aacaacactc aaccctatct cgggctattc   4140
ttttgattta taagggattt tgccgatttc ggcctattgg ttaaaaaatg agctgattta   4200
acaaaaattt aacgcgaatt ttaacaaaat attaacgttt acaattttat ggtgcactct   4260
cagtacaatc tgctctgatg ccgcatagtt aagccagccc cgacacccgc caacacccgc   4320
tgacgcgccc tgacgggctt gtctgctccc ggcatccgct tacagacaag ctgtgaccgt   4380
```

ctccgggagc tgcatgtgtc agaggttttc accgtcatca ccgaaacgcg cgagacgaaa 4440
gggcctcgtg atacgcctat ttttataggt taatgtcatg ataataatgg tttcttagac 4500
gtcaggtggc acttttcggg gaaatgtgcg cggaacccct atttgtttat ttttctaaat 4560
acattcaaat atgtatccgc tcatgagaca ataaccctga taaatgcttc aataatattg 4620
aaaaaggaag agtatgagta ttcaacattt ccgtgtcgcc cttattccct tttttgcggc 4680
attttgcctt cctgtttttg ctcacccaga aacgctggtg aaagtaaaag atgctgaaga 4740
tcagttgggt gcacgagtgg gttacatcga actggatctc aacagcggta agatccttga 4800
gagttttcgc cccgaagaac gttttccaat gatgagcact tttaaagttc tgctatgtgg 4860
cgcggtatta tcccgtattg acgccgggca agagcaactc ggtcgccgca tacactattc 4920
tcagaatgac ttggttgagt actcaccagt cacagaaaag catcttacgg atggcatgac 4980
agtaagagaa ttatgcagtg ctgccataac catgagtgat aacactgcgg ccaacttact 5040
tctgacaacg atcggaggac cgaaggagct aaccgctttt ttgcacaaca tgggggatca 5100
tgtaactcgc cttgatcgtt gggaaccgga gctgaatgaa gccataccaa acgacgagcg 5160
tgacaccacg atgcctgtag caatggcaac aacgttgcgc aaactattaa ctggcgaact 5220
acttactcta gcttcccggc aacaattaat agactggatg gaggcggata aagttgcagg 5280
accacttctg cgctcggccc ttccggctgg ctggtttatt gctgataaat ctggagccgg 5340
tgagcgtggg tctcgcggta tcattgcagc actggggcca gatggtaagc cctcccgtat 5400
cgtagttatc tacacgacgg ggagtcaggc aactatggat gaacgaaata gacagatcgc 5460
tgagataggt gcctcactga ttaagcattg gtaactgtca gaccaagttt actcatatat 5520
actttagatt gatttaaaac ttcattttta atttaaaagg atctaggtga agatcctttt 5580
tgataatctc atgaccaaaa tcccttaacg tgagttttcg ttccactgag cgtcagaccc 5640
cgtagaaaag atcaaaggat cttcttgaga tccttttttt ctgcgcgtaa tctgctgctt 5700
gcaaacaaaa aaaccaccgc taccagcggt ggtttgtttg ccggatcaag agctaccaac 5760
tctttttccg aaggtaactg gcttcagcag agcgcagata ccaaatactg tccttctagt 5820
gtagccgtag ttaggccacc acttcaagaa ctctgtagca ccgcctacat acctcgctct 5880
gctaatcctg ttaccagtgg ctgctgccag tggcgataag tcgtgtctta ccgggttgga 5940
ctcaagacga tagttaccgg ataaggcgca gcggtcgggc tgaacggggg gttcgtgcac 6000
acagcccagc ttggagcgaa cgacctacac cgaactgaga tacctacagc gtgagctatg 6060
agaaagcgcc acgcttcccg aagggagaaa ggcggacagg tatccggtaa gcggcagggt 6120
cggaacagga gagcgcacga gggagcttcc agggggaaac gcctggtatc tttatagtcc 6180
tgtcgggttt cgccacctct gacttgagcg tcgatttttg tgatgctcgt caggggggcg 6240
gagcctatgg aaaaacgcca gcaacgcggc ctttttacgg ttcctggcct tttgctggcc 6300
ttttgctc 6308

<210> SEQ ID NO 13
<211> LENGTH: 14
<212> TYPE: DNA
<213> ORGANISM: Artificial Sequence
<220> FEATURE:
<223> OTHER INFORMATION: linker

<400> SEQUENCE: 13
ggcgcgccac gcgt 14

<210> SEQ ID NO 14
<211> LENGTH: 19
<212> TYPE: DNA
<213> ORGANISM: Artificial Sequence
<220> FEATURE:
<223> OTHER INFORMATION: forward primer 1 for AAV vector titration

<400> SEQUENCE: 14
agggatggtt ggttggtgg 19

<210> SEQ ID NO 15
<211> LENGTH: 19
<212> TYPE: DNA
<213> ORGANISM: Artificial Sequence
<220> FEATURE:
<223> OTHER INFORMATION: reverse primer 1 for AAV vector titration

<400> SEQUENCE: 15
ggcaggtgct ccaggtaat 19

<210> SEQ ID NO 16
<211> LENGTH: 19
<212> TYPE: DNA
<213> ORGANISM: Artificial Sequence
<220> FEATURE:
<223> OTHER INFORMATION: forward primer 2 for AAV vector titration

<400> SEQUENCE: 16
ccatcctcac gacacccaa 19

<210> SEQ ID NO 17
<211> LENGTH: 18
<212> TYPE: DNA
<213> ORGANISM: Artificial Sequence
<220> FEATURE:
<223> OTHER INFORMATION: reverse primer 2 for AAV vector titration

<400> SEQUENCE: 17
gtccaccatt cctccgct 18

<210> SEQ ID NO 18
<211> LENGTH: 20
<212> TYPE: DNA
<213> ORGANISM: Artificial Sequence
<220> FEATURE:
<223> OTHER INFORMATION: hGAAco forward primer

<400> SEQUENCE: 18
accccttcat gcctccttat 20

<210> SEQ ID NO 19
<211> LENGTH: 20
<212> TYPE: DNA
<213> ORGANISM: Artificial Sequence
<220> FEATURE:
<223> OTHER INFORMATION: hGAAco reverse primer

<400> SEQUENCE: 19
tccatgtagt ccaggtcgtt 20

<210> SEQ ID NO 20
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 20
tgtgtccgtc gtggatctga 20

<210> SEQ ID NO 21
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 21
gcctgcttca ccaccttctt ga 22

<210> SEQ ID NO 22
<211> LENGTH: 1426
<212> TYPE: DNA
<213> ORGANISM: Artificial Sequence
<220> FEATURE:
<223> OTHER INFORMATION: Desmin promoter

<400> SEQUENCE: 22
acacacctac tagtaacccc tccagctggt gatggcaggt ctagggtagg accagtgact 60
ggctcctaat cgagcactct attttcaggg tttgcattcc aaaagggtca ggtccaagag 120
ggacctggag tgccaagtgg aggtgtagag gcacggccag tacccatgga gaatggtgga 180
tgtccttagg ggttagcaag tgccgtgtgc taaggagggg gctttggagg ttgggcaggc 240
cctctgtggg gctccatttt tgtggggggtg ggggctggag cattataggg ggtgggaagt 300
gattggggct gtcaccctag ccttccttat ctgacgccca cccatgcctc ctcaggtacc 360
ccctgccccc cacagctcct ctcctgtgcc ttgtttccca gccatgcgtt ctcctctata 420
aatacccgct ctggtatttg gggttggcag ctgttgctgc cagggagatg gttgggttga 480
catgcggctc ctgacaaaac acaaaccccct ggtgtgtgtg ggcgtgggtg gtgtgagtag 540
ggggatgaat cagggagggg gcgggggacc cagggggcag gagccacaca aagtctgtgc 600
gggggtggga gcgcacatag caattggaaa ctgaaagctt atcagaccct ttctggaaat 660
cagcccactg tttataaact tgaggcccca ccctcgacag taccggggag gaagagggcc 720
tgcactagtc cagagggaaa ctgaggctca gggctagctc gcccatagac atacatggca 780
ggcaggcttt ggccaggatc cctccgcctg ccaggcgtct ccctgccctc ccttcctgcc 840
tagagacccc caccctcaag cctggctggt ctttgcctga gacccaaacc tcttcgactt 900
caagagaata tttaggaaca aggtggttta gggcctttcc tgggaacagg ccttgaccct 960
ttaagaaatg acccaaagtc tctccttgac caaaaagggg accctcaaac taaagggaag 1020
cctctcttct gctgtctccc ctgaccccac tccccccac cccaggacga ggagataacc 1080
agggctgaaa gaggcccgcc tgggggctgc agacatgctt gctgcctgcc ctggcgaagg 1140
attggcaggc ttgcccgtca caggaccccc gctggctgac tcaggggcgc aggcctcttg 1200
cgggggagct ggcctccccg cccccacggc cacgggccgc cctttcctgg caggacagcg 1260
ggatcttgca gctgtcaggg gaggggaggc gggggctgat gtcaggaggg atacaaatag 1320
tgccgacggc tgggggccct gtctcccctc gccgcatcca ctctccggcc ggccgcctgc 1380
ccgccgcctc ctccgtgcgc ccgccagcct cgcccgcgcc gtcacc 1426

<210> SEQ ID NO 23
<211> LENGTH: 798
<212> TYPE: DNA
<213> ORGANISM: Artificial Sequence -continued
<220> FEATURE:
<223> OTHER INFORMATION: MHCK7 promoter

<400> SEQUENCE: 23
tagttcatag cccatatatg gagttccgct agaagctgca tgtctaagct agacccttca 60
gattaaaaat aactgaggta agggcctggg taggggaggt ggtgtgagac gctcctgtct 120
ctcctctatc tgcccatcgg ccctttgggg aggaggaatg tgcccaagga ctaaaaaaag 180
gccatggagc cagaggggcg agggcaacag acctttcatg ggcaaacctt ggggccctgc 240
tgtctagcat gccccactac gggtctaggc tgcccatgta aggaggcaag gcctggggac 300
acccgagatg cctggttata attaacccag acatgtggct gccccccccc ccccaacacc 360
tgctgcctct aaaaataacc ctgtccctgg tggatcccct gcatgcgaag atcttcgaac 420
aaggctgtgg gggactgagg gcaggctgta acaggcttgg gggccagggc ttatacgtgc 480
ctgggactcc caaagtatta ctgttccatg ttcccggcga agggccagct gtcccccgcc 540
agctagactc agcacttagt ttaggaacca gtgagcaagt cagcccttgg ggcagcccat 600
acaaggccat ggggctgggc aagctgcacg cctgggtccg gggtgggcac ggtgcccggg 660
caacgagctg aaagctcatc tgctctcagg ggcccctccc tggggacagc ccctcctggc 720
tagtcacacc ctgtaggctc ctctatataa cccaggggca caggggctgc cctcattcta 780
ccaccacctc cacagcac 798